US010004786B2

(12) United States Patent
Riber et al.

(10) Patent No.: US 10,004,786 B2
(45) Date of Patent: Jun. 26, 2018

(54) ACYLATED GLUCAGON ANALOGUES

(71) Applicant: Zealand Pharma A/S, Glostrup (DK)

(72) Inventors: Ditte Riber, Brønshøj (DK); Eddi Meier, Vaerløse (DK); Jens Rosengren Daugaard, Virum (DK); Marie Skovgaard, Copenhagen Ø (DK); Jakob Lind Tolborg, Herlev (DK); Gita Kampen, Nærum (DK); Camilla Ærteberg Bæk, Allerød (DK)

(73) Assignee: Zealand Pharma A/S, Glostrup (DK)

( * ) Notice: Subject to any disclaimer, the term of this patent is extended or adjusted under 35 U.S.C. 154(b) by 0 days. days.

(21) Appl. No.: 14/843,047

(22) Filed: Sep. 2, 2015

(65) Prior Publication Data

US 2016/0120951 A1 May 5, 2016

Related U.S. Application Data

(63) Continuation of application No. 13/383,783, filed as application No. PCT/DK2010/000099 on Jun. 24, 2010, now Pat. No. 9,156,901.

(60) Provisional application No. 61/225,080, filed on Jul. 13, 2009.

(30) Foreign Application Priority Data

Jul. 13, 2009 (EP) ..................................... 09251780
Mar. 22, 2010 (EP) ..................................... 10157240
May 10, 2010 (DK) ................................ 2010 00412

(51) Int. Cl.
*A61K 38/00* (2006.01)
*A61K 38/26* (2006.01)
*C07K 14/605* (2006.01)
*A61K 47/48* (2006.01)

(52) U.S. Cl.
CPC ........ *A61K 38/26* (2013.01); *A61K 47/48023* (2013.01); *C07K 14/605* (2013.01)

(58) Field of Classification Search
None
See application file for complete search history.

(56) References Cited

U.S. PATENT DOCUMENTS

| | | |
|---|---|---|
| 7,994,122 B2 | 8/2011 | Riber et al. |
| 8,642,540 B2 | 2/2014 | Meier et al. |
| 8,642,541 B2 | 2/2014 | Meier et al. |
| 8,680,049 B2 | 3/2014 | Meier et al. |
| 8,685,919 B2 * | 4/2014 | Meier .................. C07K 14/605 514/4.8 |
| 9,156,901 B2 | 10/2015 | Riber et al. |
| 9,169,310 B2 | 10/2015 | Riber et al. |
| 9,180,169 B2 | 11/2015 | Tolborg et al. |
| 9,403,894 B2 | 8/2016 | Meier et al. |
| 9,896,495 B2 | 2/2018 | Riber et al. |
| 2005/0070469 A1 | 3/2005 | Bloom et al. |
| 2010/0099601 A1 | 4/2010 | Weiss |
| 2010/0190701 A1 | 7/2010 | Day et al. |
| 2010/0240883 A1 | 9/2010 | Wu et al. |
| 2011/0230397 A1 | 9/2011 | Carriero et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2012/0178670 A1 | 7/2012 | Riber et al. |
| 2013/0053304 A1 | 2/2013 | Wang et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0210744 A1 | 7/2015 | Riber et al. |
| 2015/0299281 A1 | 10/2015 | Just et al. |
| 2015/0322130 A1 | 11/2015 | DiMarchi et al. |
| 2015/0376257 A1 | 12/2015 | Riber et al. |
| 2016/0000883 A1 | 1/2016 | Fosgerau et al. |
| 2016/0009777 A1 | 1/2016 | Tolborg et al. |
| 2016/0304576 A1 | 10/2016 | Meier et al. |
| 2016/0347813 A1 | 12/2016 | Hamprecht et al. |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |

(Continued)

OTHER PUBLICATIONS

U.S. Appl. No. 14/857,067, Zealand Pharma A/S.
Abbrecht et al., "Erythrocyte life-span in mice acclimatized to different degrees of hypoxia," J Appl Physiol. 32(4):443-445 (1972).
Adelhorst et al., "Structure-activity studies of glucagon-like peptide-1," J Biol Chem 269(9): 6275-6278 (1994).
Ali et al., "Cardiomyocyte glucagon receptor signaling modulates outcomes in mice with experimental myocardial infarction," Mol Metab. 4(2):132-143 (2015).
Altschul et al., "Local alignment statistics," Methods Enzymol. 266:460-480 (1996).
Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).
Authier et al., "Endosomal proteolysis of glucagon at neutral pH generates the bioactive degradation product miniglucagon-(19-29)," Endocrinology. 144(12):5353-5364 (2003).
Blache et al., "Endopeptidase from rat liver membranes, which generates miniglucagon from glucagon," J Biol Chem. 268(29):21748-21753 (1993).

(Continued)

*Primary Examiner* — Thomas S Heard
(74) *Attorney, Agent, or Firm* — Clark & Elbing LLP

(57) ABSTRACT

The invention provides materials and methods for promoting weight loss or preventing weight gain, and in the treatment of diabetes and associated metabolic disorders. In particular, the invention provides novel acylated glucagon analog peptides effective in such methods. The peptides may mediate their effect by having increased selectivity for the GLP-1 receptor as compared to human glucagon.

2 Claims, 13 Drawing Sheets

(56) References Cited

FOREIGN PATENT DOCUMENTS

| | | |
|---|---|---|
| EP | 0082731 A1 | 6/1983 |
| EP | 2025684 A1 | 2/2009 |
| JP | 2011-524418 A | 9/2011 |
| JP | 2012-511900 A | 5/2012 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |
| WO | WO-2004/096854 A2 | 11/2004 |
| WO | WO-2006/051110 A2 | 5/2006 |
| WO | WO-2006/097537 A2 | 9/2006 |
| WO | WO-2006/121860 A2 | 11/2006 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/100535 A2 | 9/2007 |
| WO | WO-2008/010101 A2 | 1/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/067636 A2 | 5/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/011439 A2 | 1/2010 |
| WO | WO-2010/014946 A2 | 2/2010 |
| WO | WO-2010/016940 A2 | 2/2010 |
| WO | WO-2010/029159 A1 | 3/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2010/096052 A1 | 8/2010 |
| WO | WO-2010/148089 A1 | 12/2010 |
| WO | WO-2011/006497 A1 | 1/2011 |
| WO | WO-2011/080103 A1 | 7/2011 |
| WO | WO-2011/088837 A1 | 7/2011 |
| WO | WO-2011/094337 A1 | 8/2011 |
| WO | WO-2011/117417 A1 | 9/2011 |
| WO | WO-2011/119657 A1 | 9/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO-2012/153196 A2 | 11/2012 |
| WO | WO-2012/167744 A1 | 12/2012 |
| WO | WO-2013/041678 A1 | 3/2013 |
| WO | WO-2013/092703 A2 | 6/2013 |
| WO | WO-2013/164483 A1 | 11/2013 |
| WO | WO-2014/016300 A1 | 1/2014 |
| WO | WO-2014/041195 A1 | 3/2014 |
| WO | WO-2015/067715 A2 | 5/2015 |
| WO | WO-2015/124612 A1 | 8/2015 |
| WO | WO-2016/166289 A1 | 10/2016 |

OTHER PUBLICATIONS

Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Chan et al., "Suppression of weight gain by glucagon in obese Zucker rats," Exp Mol Path. 40(3):320-327 (1984).
Cohen et al., "Oxyntomodulin suppresses appetite and reduces food intake in humans," J Clin Endocrinol Metab. 88(10):4696-4701 (2003).
Communication from the European Patent Office for European Patent Application No. 08875673.9, dated Jul. 4, 2012 (6 pages).
Dakin et al., "Oxyntomodulin inhibits food intake in the rat," Endocrinology. 142(10):4244-4250 (2001).
Dakin et al., "Peripheral oxyntomodulin reduces food intake and body weight gain in rats," Endocrinology. 145(6):2687-2695 (2004).
Day et al., "A new glucagon and GLP-1 co-agonist eliminates obesity in rodents," Nat Chem Biol. 5(10):749-757 (2009).
Delgado et al., "The uses and properties of PEG-linked proteins," Crit Rev Ther Drug Carrier Syst. 9(3,4):249-304 (1992).
Druce et al., "Investigation of structure-activity relationships of Oxyntomodulin (Oxm) using Oxm analogs," Endocrinology. 150(4):1712-1721 (2009).
England et al., "Glucagon carboxyl-terminal derivatives: Preparation, purification and characterization," Biochemistry. 21(5):940-950 (1982).
European Search Report from European Patent Application No. 07016032.0, completed Jan. 28, 2008 (8 pages).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gelfanov et al., Discovery and structural optimization of high affinity co-agonists at the glucagon and GLP-1 receptors. Understanding Biology Using Peptides. Sylvie E. Blondelle, 763-764 (2005).
Goldstein et al., "Effects of chronic heart failure on the capacity of glucagon to enhance contractility and adenyl cyclase activity of human papillary muscles," Circulation. 44(4):638-648 (1971).
Gombotz et al. "Biodegradable polymers for protein and peptide drug delivery," Bioconjug Chem. 6(4):332-351 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Hjorth et al., "Glucagon and glucagon-like peptide 1: Selective receptor recognition via distinct peptide epitopes," J Biol Chem. 269(48):30121-30124 (1994).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
International Preliminary Report on Patentability for PCT/EP2013/069286, completed Jan. 19, 2015 (40 pages).
International Preliminary Report on Patentability for PCT/GB2008/002041, dated Dec. 17, 2009 (7 pages).
International Search Report and Written Opinion for PCT/EP2013/069286, dated Dec. 18, 2013 (16 pages).

(56) References Cited

OTHER PUBLICATIONS

International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK2010/000099, dated Dec. 2, 2010 (2 pages).
International Search Report for International Application No. PCT/DK2011/000067, dated Dec. 9, 2011 (4 pages).
International Search Report for International Application No. PCT/IB2012/000134, dated Jun. 25, 2012 (3 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Jaya et al., "Mechanism of hypocholesterolemic action of glucagon," J Biosci. 12(2):111-4 (1987).
Joshi et al., "The estimation of glutaminyl deamidation and aspartyl cleavage rates in glucagon," Int J Pharm. 273(1-2):213-219 (2004).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Knudsen et al., "Potent derivatives of glucagon-like peptide-1 with pharmacokinetic properties suitable for once daily administration," J Med Chem. 43(9):1664-1669 (2000).
Madsen et al., "Structure-activity and protraction relationship of long-acting glucagon-like peptide-1 derivatives: importance of fatty acid length, polarity, and bulkiness," J Med Chem. 50(54):6126-6132 (2007).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Intl J Pharm Sci Res. 3(10):3565-3576 (2012).
NCBI Blast for Accession No. 721913A, retrieved on Dec. 15, 2009 (1 page).
Pan et al., "Design of a long acting peptide functioning as both a glucagon-like peptide-1 receptor agonist and a glucagon receptor antagonist," J Biol Chem. 281(18):12506-12515 (2006).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Pocai, "Glucagon signaling in the heart: activation or inhibition?," Mol Metab. 4(2):81-2 (2015).
Pratesi et al., "Poly-L-aspartic acid as a carrier for doxorubicin: a comparative in vivo study of free and polymer-bound drug," Br J Cancer. 52(6):841-848 (1985).
Protest of U.S. Appl. No. 12/664,534 Pursuant 37 CFR 1.291, dated Jan. 13, 2010 (14 pages).
Rose et al., "Insulin proteinase liberates from glucagon a fragment known to have enhanced activity against Ca2++ Mg2+-dependent ATPase," Biochem J. 256(3):847-51 (1988).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Written Opinion for PCT/DK2011/000072, dated Dec. 6, 2011 (6 pages).
Written Opinion for Singapore Application No. 201209089-0, dated Nov. 8, 2013 (10 pages).
Written Opinion of the International Searching Authority for PCT/GB2008/002041, dated Sep. 9, 2008 (6 pages).
Zalipsky, "Functionalized poly(ethylene glycol) for preparation of biologically relevant conjugates," Bioconjug Chem. 6(2):150-165 (1995).
Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).
Bell, "Heart failure: the frequent, forgotten, and often fatal complication of diabetes," Diabetes Care. 26(8):2433-41 (2003).
Lefèbvre, "The intriguing diversity of the glucagon gene products," Curr Diab Rep. 2(3):201-2 (2002).
Lvoff et al., "Glucagon in heart failure and in cardiogenic shock. Experience in 50 patients," Circulation. 45(3):534-42 (1972).
U.S. Appl. No. 60/132,018, Prickett et al.
Hansson, "Inflammation, atherosclerosis, and coronary artery disease," N Engl J Med. 352(16):1685-95 (2005).
International Search Report and Written Opinion for International Application No. PCT/IB2012/001090, dated Jan. 25, 2013 (15 pages).
Pocai et al., "Glucagon-like peptide 1/glucagon receptor dual agonism reverses obesity in mice," Diabetes. 58(10):2258-66 (2009).
Chabenne et al., "Optimization of the native glucagon sequence for medicinal purposes," J Diabetes Sci Technol. 4(6):1322-31 (2010).
"Molecular basis of diastolic dysfunction," Available in PMC Jul. 6, 2009, published in final edited form as: Heart Fail Clin. 4(1):13-21 (13 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Office Action for Colombian Application No. 16089238, dated Sep. 13, 2017 (18 pages).
Bowie et al., "Deciphering the message in protein sequences: tolerance to amino acid substitutions," Science. 247(4948):1306-10 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.
Bork, "Powers and pitfalls in sequence analysis: the 70% hurdle," Genome Research 10, 398-400, 2000.
Lazar et al., "Transforming growth factor alpha: mutation of aspartic acid 47 and leucine 48 results in different biological activities," Mol. Cell. Biol. 8, 1247-52, 1988.
U.S. Appl. No. 15/852,458, filed Dec. 22, 2017 (57 pages).
Diamant et al., "Diabetic cardiomyopathy in uncomplicated type 2 diabetes is associated with the metabolic syndrome and systemic inflammation," Diabetologia 48(8):1669-70 (2005).
Ebert et al., "Gastric inhibitory polypeptide," Clin Gastroenterol. 9(3):679-98 (1980).
Finan et al., "Reappraisal of GIP Pharmacology for Metabolic Diseases," Trends Mol Med. 22(5):359-76 (2016).
First Examination Report for New Zealand Patent Application No. 702333, dated Jun. 2, 2016 (4 pages).
Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).

(56) References Cited

OTHER PUBLICATIONS

Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).

International Search Report and Written Opinion for PCT/EP2013/059319, dated Sep. 12, 2013 (12 pages).

International Search Report and Written Opinion for PCT/EP2013/065519, dated Dec. 6, 2013 (11 pages).

Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 386(7):679-87 (2005).

Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).

Malde et al., "Understanding interactions of gastric inhibitory polypeptide (GIP) with its G-protein coupled receptor through NMR and molecular modeling," J Pept Sci. 13(5):287-300 (2007).

Manhart et al., "Structure-function analysis of a series of novel GIP analogues containing different helical length linkers," Biochemistry. 42(10):3081-8 (2003).

Matsumoto et al., "Plasma Incretin Levels and Dipeptidyl Peptidase-4 Activity in Patients with Obstructive Sleep Apnea," Ann Am Thorac Soc. 13(8):1378-87 (2016).

Runge et al., "Differential structural properties of GLP-1 and exendin-4 determine their relative affinity for the GLP-1 receptor N-terminal extracellular domain," Biochemistry. 46(19):5830-40 (2007).

Unson et al., "Positively charged residues at positions 12, 17, and 18 of glucagon ensure maximum biological potency," J Biol Chem. 273(17):10308-12 (1998).

\* cited by examiner

SEQUENCE LISTING

```
<160> NUMBER OF SEQ ID NOS: 131

<210> SEQ ID NO 1
<211> LENGTH: 29
<212> TYPE: PRT
<213> ORGANISM: Artificial
<220> FEATURE:
<223> OTHER INFORMATION: Synthetic Construct

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Lys Arg Asn Arg Asn Asn Ile Ala
1               5

<210> SEQ ID NO 3
<211> LENGTH: 37
<212> TYPE: PRT
<213> ORGANISM: Artificial Sequence
<220> FEATURE:
<223> OTHER INFORMATION: Synthetic Construct

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
```

```
                20                  25                  30

Arg Asn Asn Ile Ala
        35

<210> SEQ ID NO 4
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is selected from Aib or Ser
<220> FEATURE:
<221> NAME/KEY: MISC_FEATURE
<222> LOCATION: (12)..(12)
<223> OTHER INFORMATION: X12 is selected from Lys, Arg and Leu
<220> FEATURE:
<221> NAME/KEY: MISC_FEATURE
<222> LOCATION: (16)..(16)
<223> OTHER INFORMATION: X16 is selected from Arg, Glu, Lys, Ser, Cys,
      Dbu, Dpr, Orn, optionally covalently attached to a lipophilic
      substituent
<220> FEATURE:
<221> NAME/KEY: MISC_FEATURE
<222> LOCATION: (17)..(17)
<223> OTHER INFORMATION: X17 is selected from Arg or Glu, Lys, Ser, Cys,
      Dbu, Dpr, Orn, covalently attached to a lipophilic substituent
<220> FEATURE:
<221> NAME/KEY: MISC_FEATURE
<222> LOCATION: (20)..(20)
<223> OTHER INFORMATION: X20 is selected from Arg, His or Glu, Lys, Ser,
      Cys, Dbu, Dpr, Orn, optionally covalently attached to a lipophilic
      substituent
<220> FEATURE:
<221> NAME/KEY: MISC_FEATURE
<222> LOCATION: (21)..(21)
<223> OTHER INFORMATION: X21 is selected from Asp or Glu
<220> FEATURE:
<221> NAME/KEY: MISC_FEATURE
<222> LOCATION: (24)..(24)
<223> OTHER INFORMATION: X24 is selected from Ala or Glu, Lys, Ser, Cys,
      Dbu, Dpr, Orn, optionally covalently attached to a lipophilic
      substituent
<220> FEATURE:
<221> NAME/KEY: MISC_FEATURE
<222> LOCATION: (27)..(27)
<223> OTHER INFORMATION: X27 is selected from Leu or Glu, Lys, Ser, Cys,
      Dbu, Dpr, Orn, optionally covalently attached to a lipophilic
      substituent
<220> FEATURE:
<221> NAME/KEY: MISC_FEATURE
<222> LOCATION: (28)..(28)
<223> OTHER INFORMATION: X28 is selected from Arg or Glu, Lys, Ser, Cys,
      Dbu, Dpr, Orn, optionally covalently attached to a lipophilic
      substituent
<220> FEATURE:
<221> NAME/KEY: MISC_FEATURE
<222> LOCATION: (30)..(30)
<223> OTHER INFORMATION: X30 is absent or Glu, Lys, Ser, Cys, Dbu, Dpr,
      Orn, optionally covalently attached to a lipophilic substituent

<400> SEQUENCE: 4

His Xaa Gln Gly Thr Phe Thr Ser Asp Tyr Ser Xaa Tyr Leu Asp Xaa
1               5                   10                  15

Xaa Ala Ala Xaa Xaa Phe Val Xaa Trp Leu Xaa Xaa Ala Xaa
            20                  25                  30

<210> SEQ ID NO 5
<211> LENGTH: 29
<212> TYPE: PRT
<213> ORGANISM: Artificial
<220> FEATURE:
```

```
<223> OTHER INFORMATION: Synthetic Construct
<220> FEATURE:
<221> NAME/KEY: MISC_FEATURE
<222> LOCATION: (17)..(17)
<223> OTHER INFORMATION: K(Hexadecanoyl-gamma-Glu)

<400> SEQUENCE: 5

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 6
<211> LENGTH: 29
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (12)..(12)
<223> OTHER INFORMATION: X12 is selected from Lys, Arg and Leu
<220> FEATURE:
<221> NAME/KEY: MISC_FEATURE
<222> LOCATION: (16)..(16)
<223> OTHER INFORMATION: X16 is selected from Ser and Glu, Lys or Cys,
      optionally covalently attached to a lipophilic substituent
<220> FEATURE:
<221> NAME/KEY: MISC_FEATURE
<222> LOCATION: (17)..(17)
<223> OTHER INFORMATION: X17 is Glu, Lys or Cys, covalently attached to
      a lipophilic substituent
<220> FEATURE:
<221> NAME/KEY: MISC_FEATURE
<222> LOCATION: (20)..(20)
<223> OTHER INFORMATION: X20 is selected from His and Glu, Lys or Cys,
      optionally covalently attached to a lipophilic substituent
<220> FEATURE:
<221> NAME/KEY: MISC_FEATURE
<222> LOCATION: (21)..(21)
<223> OTHER INFORMATION: X21 is selected from Asp and Glu
<220> FEATURE:
<221> NAME/KEY: MISC_FEATURE
<222> LOCATION: (24)..(24)
<223> OTHER INFORMATION: X24 is selected from Ala and Glu
<220> FEATURE:
<221> NAME/KEY: MISC_FEATURE
<222> LOCATION: (28)..(28)
<223> OTHER INFORMATION: X28 is selected from Ser, Lys and Arg

<400> SEQUENCE: 6

His Xaa Gln Gly Thr Phe Thr Ser Asp Tyr Ser Xaa Tyr Leu Asp Xaa
1               5                   10                  15

Xaa Ala Ala Xaa Xaa Phe Val Xaa Trp Leu Leu Xaa Ala
            20                  25

<210> SEQ ID NO 7
<211> LENGTH: 29
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: X12 is selected from Lys, Arg and Leu
<220> FEATURE:
<221> NAME/KEY: MISC_FEATURE
<222> LOCATION: (16)..(16)
```

```
<223> OTHER INFORMATION: X16 is selected from Ser and Glu, Lys or Cys,
      optionally covalently attached to a lipophilic substituent
<220> FEATURE:
<221> NAME/KEY: MISC_FEATURE
<222> LOCATION: (17)..(17)
<223> OTHER INFORMATION: X17 is Glu, Lys or Cys, covalently attached to
      a lipophilic substituent
<220> FEATURE:
<221> NAME/KEY: MISC_FEATURE
<222> LOCATION: (20)..(20)
<223> OTHER INFORMATION: X20 is selected from His and Glu, Lys or Cys,
      optionally covalently attached to a lipophilic substituent
<220> FEATURE:
<221> NAME/KEY: MISC_FEATURE
<222> LOCATION: (21)..(21)
<223> OTHER INFORMATION: X21 is selected from Asp and Glu
<220> FEATURE:
<221> NAME/KEY: MISC_FEATURE
<222> LOCATION: (24)..(24)
<223> OTHER INFORMATION: X24 is selected from Ala and Glu
<220> FEATURE:
<221> NAME/KEY: MISC_FEATURE
<222> LOCATION: (28)..(28)
<223> OTHER INFORMATION: X28 is selected from Ser, Lys and Arg

<400> SEQUENCE: 7

His Ser Gln Gly Thr Phe Thr Ser Asp Tyr Ser Xaa Tyr Leu Asp Xaa
1               5                   10                  15

Xaa Ala Ala Xaa Xaa Phe Val Xaa Trp Leu Leu Xaa Ala
            20                  25

<210> SEQ ID NO 8
<211> LENGTH: 29
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (12)..(12)
<223> OTHER INFORMATION: X12 is selected from Lys and Arg
<220> FEATURE:
<221> NAME/KEY: MISC_FEATURE
<222> LOCATION: (17)..(17)
<223> OTHER INFORMATION: X17 is Glu, Lys or Cys, covalently attached to
      a lipophilic substituent
<220> FEATURE:
<221> NAME/KEY: MISC_FEATURE
<222> LOCATION: (20)..(20)
<223> OTHER INFORMATION: X20 is selected from His and Glu, Lys or Cys,
      optionally covalently attached to a lipophilic substituent
<220> FEATURE:
<221> NAME/KEY: MISC_FEATURE
<222> LOCATION: (21)..(21)
<223> OTHER INFORMATION: X21 is selected from Asp and Glu
<220> FEATURE:
<221> NAME/KEY: MISC_FEATURE
<222> LOCATION: (24)..(24)
<223> OTHER INFORMATION: X24 is selected from Ala and Glu
<220> FEATURE:
<221> NAME/KEY: MISC_FEATURE
<222> LOCATION: (28)..(28)
<223> OTHER INFORMATION: X28 is selected from Ser, Lys and Arg

<400> SEQUENCE: 8

His Xaa Gln Gly Thr Phe Thr Ser Asp Tyr Ser Xaa Tyr Leu Asp Ser
1               5                   10                  15

Xaa Ala Ala Xaa Xaa Phe Val Xaa Trp Leu Leu Xaa Ala
            20                  25
```

```
<210> SEQ ID NO 9
<211> LENGTH: 29
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: X12 is selected from Lys or Arg
<220> FEATURE:
<221> NAME/KEY: MISC_FEATURE
<222> LOCATION: (17)..(17)
<223> OTHER INFORMATION: X17 is Glu, Lys or Cys, covalently attached to
      a lipophilic substituent
<220> FEATURE:
<221> NAME/KEY: MISC_FEATURE
<222> LOCATION: (20)..(20)
<223> OTHER INFORMATION: X20 is selected from His and Glu, Lys or Cys,
      optionally covalently attached to a lipophilic substituent
<220> FEATURE:
<221> NAME/KEY: MISC_FEATURE
<222> LOCATION: (21)..(21)
<223> OTHER INFORMATION: X21 is selected from Asp and Glu
<220> FEATURE:
<221> NAME/KEY: MISC_FEATURE
<222> LOCATION: (24)..(24)
<223> OTHER INFORMATION: X24 is selected from Ala and Glu
<220> FEATURE:
<221> NAME/KEY: MISC_FEATURE
<222> LOCATION: (28)..(28)
<223> OTHER INFORMATION: X28 is selected from Ser, Lys and Arg

<400> SEQUENCE: 9

His Ser Gln Gly Thr Phe Thr Ser Asp Tyr Ser Xaa Tyr Leu Asp Ser
1               5                   10                  15

Xaa Ala Ala Xaa Xaa Phe Val Xaa Trp Leu Leu Xaa Ala
            20                  25

<210> SEQ ID NO 10
<211> LENGTH: 29
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (12)..(12)
<223> OTHER INFORMATION: X12 is selected from Lys and Arg
<220> FEATURE:
<221> NAME/KEY: MISC_FEATURE
<222> LOCATION: (17)..(17)
<223> OTHER INFORMATION: X17 is Glu, Lys or Cys, covalently attached to
      a lipophilic substituent
<220> FEATURE:
<221> NAME/KEY: MISC_FEATURE
<222> LOCATION: (21)..(21)
<223> OTHER INFORMATION: X21 is selected from Asp and Glu
<220> FEATURE:
<221> NAME/KEY: MISC_FEATURE
<222> LOCATION: (24)..(24)
<223> OTHER INFORMATION: X24 is selected from Ala and Glu
<220> FEATURE:
<221> NAME/KEY: MISC_FEATURE
<222> LOCATION: (28)..(28)
<223> OTHER INFORMATION: X28 is selected from Ser, Lys and Arg

<400> SEQUENCE: 10

His Xaa Gln Gly Thr Phe Thr Ser Asp Tyr Ser Xaa Tyr Leu Asp Ser
1               5                   10                  15
```

```
Xaa Ala Ala His Xaa Phe Val Xaa Trp Leu Leu Xaa Ala
            20                  25

<210> SEQ ID NO 11
<211> LENGTH: 29
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: X12 is selected from Lys and Arg
<220> FEATURE:
<221> NAME/KEY: MISC_FEATURE
<222> LOCATION: (17)..(17)
<223> OTHER INFORMATION: X17 is Glu, Lys or Cys, covalently attached to
      a lipophilic substituent
<220> FEATURE:
<221> NAME/KEY: MISC_FEATURE
<222> LOCATION: (21)..(21)
<223> OTHER INFORMATION: X21 is selected from Asp and Glu
<220> FEATURE:
<221> NAME/KEY: MISC_FEATURE
<222> LOCATION: (24)..(24)
<223> OTHER INFORMATION: X24 is selected from Ala and Glu
<220> FEATURE:
<221> NAME/KEY: MISC_FEATURE
<222> LOCATION: (28)..(28)
<223> OTHER INFORMATION: X28 is selected from Ser, Lys and Arg

<400> SEQUENCE: 11

His Ser Gln Gly Thr Phe Thr Ser Asp Tyr Ser Xaa Tyr Leu Asp Ser
1               5                   10                  15

Xaa Ala Ala His Xaa Phe Val Xaa Trp Leu Leu Xaa Ala
            20                  25

<210> SEQ ID NO 12
<211> LENGTH: 28
<212> TYPE: PRT
<213> ORGANISM: artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is conjugated to a lipophilic substituent
<220> FEATURE:
<221> NAME/KEY: MISC_FEATURE
<222> LOCATION: (28)..(28)
<223> OTHER INFORMATION: X28 is Ser or absent

<400> SEQUENCE: 12

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Xaa
            20                  25

<210> SEQ ID NO 13
<211> LENGTH: 29
<212> TYPE: PRT
<213> ORGANISM: Artificial
<220> FEATURE:
<223> OTHER INFORMATION: Synthetic Construct

<400> SEQUENCE: 13
```

-continued

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 14
<211> LENGTH: 29
<212> TYPE: PRT
<213> ORGANISM: Artificial
<220> FEATURE:
<223> OTHER INFORMATION: Synthetic Construct

<400> SEQUENCE: 14

His Ser Gln Gly Thr Phe Thr Ser Asp Tyr Ser Lys Tyr Leu Asp Lys
1               5                   10                  15

Lys Ala Ala His Asp Phe Val Glu Trp Leu Leu Arg Ala
            20                  25

<210> SEQ ID NO 15
<211> LENGTH: 29
<212> TYPE: PRT
<213> ORGANISM: Artificial
<220> FEATURE:
<223> OTHER INFORMATION: Synthetic Construct

<400> SEQUENCE: 15

His Ser Gln Gly Thr Phe Thr Ser Asp Tyr Ser Lys Tyr Leu Asp Ser
1               5                   10                  15

Lys Ala Ala Lys Asp Phe Val Glu Trp Leu Leu Arg Ala
            20                  25

<210> SEQ ID NO 16
<211> LENGTH: 29
<212> TYPE: PRT
<213> ORGANISM: Artificial
<220> FEATURE:
<223> OTHER INFORMATION: Synthetic Construct

<400> SEQUENCE: 16

His Ser Gln Gly Thr Phe Thr Ser Asp Tyr Ser Lys Tyr Leu Asp Ser
1               5                   10                  15

Lys Ala Ala His Asp Phe Val Glu Trp Leu Lys Arg Ala
            20                  25

<210> SEQ ID NO 17
<211> LENGTH: 29
<212> TYPE: PRT
<213> ORGANISM: Artificial
<220> FEATURE:
<223> OTHER INFORMATION: Synthetic Construct

<400> SEQUENCE: 17

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 18
<211> LENGTH: 29
<212> TYPE: PRT
<213> ORGANISM: Artificial
<220> FEATURE:
<223> OTHER INFORMATION: Synthetic Construct

<400> SEQUENCE: 18

His Ser Gln Gly Thr Phe Thr Ser Asp Tyr Ser Arg Tyr Leu Asp Ser
1               5                   10                  15

Lys Ala Ala His Asp Phe Val Glu Trp Leu Leu Arg Ala
            20                  25

<210> SEQ ID NO 19
<211> LENGTH: 29
<212> TYPE: PRT
<213> ORGANISM: Artificial
<220> FEATURE:
<223> OTHER INFORMATION: Synthetic Construct

<400> SEQUENCE: 19

His Ser Gln Gly Thr Phe Thr Ser Asp Tyr Ser Leu Tyr Leu Asp Ser
1               5                   10                  15

Lys Ala Ala His Asp Phe Val Glu Trp Leu Leu Arg Ala
            20                  25

<210> SEQ ID NO 20
<211> LENGTH: 30
<212> TYPE: PRT
<213> ORGANISM: Artificial
<220> FEATURE:
<223> OTHER INFORMATION: Synthetic Construct

<400> SEQUENCE: 20

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala Lys
            20                  25                  30

<210> SEQ ID NO 21
<211> LENGTH: 30
<212> TYPE: PRT
<213> ORGANISM: Artificial
<220> FEATURE:
<223> OTHER INFORMATION: Synthetic Construct

<400> SEQUENCE: 21

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala Lys
            20                  25                  30

<210> SEQ ID NO 22
<211> LENGTH: 29
<212> TYPE: PRT
<213> ORGANISM: Artificial
<220> FEATURE:
<223> OTHER INFORMATION: Synthetic Construct

<400> SEQUENCE: 22

His Ser Gln Gly Thr Phe Thr Ser Asp Tyr Ser Lys Tyr Leu Asp Ser
1               5                   10                  15

Lys Ala Ala His Asp Phe Val Glu Trp Leu Lys Ser Ala
            20                  25

<210> SEQ ID NO 23
<211> LENGTH: 29
<212> TYPE: PRT
<213> ORGANISM: Artificial
<220> FEATURE:
<223> OTHER INFORMATION: Synthetic Construct

```
<400> SEQUENCE: 23

His Ser Gln Gly Thr Phe Thr Ser Asp Tyr Ser Lys Tyr Leu Asp Ser
1               5                   10                  15

Lys Ala Ala His Asp Phe Val Lys Trp Leu Leu Arg Ala
            20                  25

<210> SEQ ID NO 24
<211> LENGTH: 29
<212> TYPE: PRT
<213> ORGANISM: Artificial
<220> FEATURE:
<223> OTHER INFORMATION: Synthetic Construct

<400> SEQUENCE: 24

His Ser Gln Gly Thr Phe Thr Ser Asp Tyr Ser Lys Tyr Leu Asp Ser
1               5                   10                  15

Cys Ala Ala His Asp Phe Val Glu Trp Leu Leu Arg Ala
            20                  25

<210> SEQ ID NO 25
<211> LENGTH: 29
<212> TYPE: PRT
<213> ORGANISM: Artificial
<220> FEATURE:
<223> OTHER INFORMATION: Synthetic Construct

<400> SEQUENCE: 25

His Ser Gln Gly Thr Phe Thr Ser Asp Tyr Ser Lys Tyr Leu Asp Ser
1               5                   10                  15

Cys Ala Ala His Asp Phe Val Glu Trp Leu Leu Ser Ala
            20                  25

<210> SEQ ID NO 26
<211> LENGTH: 29
<212> TYPE: PRT
<213> ORGANISM: Artificial
<220> FEATURE:
<223> OTHER INFORMATION: Synthetic Construct

<400> SEQUENCE: 26

His Ser Gln Gly Thr Phe Thr Ser Asp Tyr Ser Lys Tyr Leu Asp Ser
1               5                   10                  15

Lys Ala Ala Cys Asp Phe Val Glu Trp Leu Leu Arg Ala
            20                  25

<210> SEQ ID NO 27
<211> LENGTH: 29
<212> TYPE: PRT
<213> ORGANISM: Artificial
<220> FEATURE:
<223> OTHER INFORMATION: Synthetic Construct

<400> SEQUENCE: 27

His Ser Gln Gly Thr Phe Thr Ser Asp Tyr Ser Lys Tyr Leu Asp Lys
1               5                   10                  15

Ser Ala Ala His Asp Phe Val Glu Trp Leu Leu Arg Ala
            20                  25

<210> SEQ ID NO 28
<211> LENGTH: 29
<212> TYPE: PRT
<213> ORGANISM: Artificial
<220> FEATURE:
<223> OTHER INFORMATION: Synthetic Construct
```

```
<220> FEATURE:
<221> NAME/KEY: MISC_FEATURE
<222> LOCATION: (2)..(2)
<223> OTHER INFORMATION: X2 is Aib

<400> SEQUENCE: 28

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 29
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 29

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala Lys
            20                  25                  30

<210> SEQ ID NO 30
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 30

His Xaa Gln Gly Thr Phe Thr Ser Asp Tyr Ser Lys Tyr Leu Asp Ser
1               5                   10                  15

Lys Ala Ala Arg Asp Phe Val Ala Trp Leu Leu Arg Ala
            20                  25

<210> SEQ ID NO 31
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 31

His Xaa Gln Gly Thr Phe Thr Ser Asp Tyr Ser Lys Tyr Leu Asp Ser
1               5                   10                  15

Lys Ala Ala Lys Asp Phe Val Ala Trp Leu Leu Arg Ala
            20                  25

<210> SEQ ID NO 32
<211> LENGTH: 29
<212> TYPE: PRT
<213> ORGANISM: Artificial
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 32

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 33
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 33

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 34
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 34

His Xaa Gln Gly Thr Phe Thr Ser Asp Tyr Ser Lys Tyr Leu Asp Ser
1               5                   10                  15

Lys Ala Ala Lys Asp Phe Val Ala Trp Leu Leu Ser Ala
            20                  25

<210> SEQ ID NO 35
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 35

His Xaa Gln Gly Thr Phe Thr Ser Asp Tyr Ser Lys Tyr Leu Asp Ser
1               5                   10                  15

Lys Ala Ala His Asp Phe Val Ala Trp Leu Leu Lys Ala
            20                  25

<210> SEQ ID NO 36
<211> LENGTH: 29
<212> TYPE: PRT
<213> ORGANISM: Artificial
```

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 36

His Xaa Gln Gly Thr Phe Thr Ser Asp Tyr Ser Lys Tyr Leu Asp Lys
1               5                   10                  15

Lys Ala Ala His Asp Phe Val Ala Trp Leu Leu Arg Ala
            20                  25

<210> SEQ ID NO 37
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 37

His Xaa Gln Gly Thr Phe Thr Ser Asp Tyr Ser Arg Tyr Leu Asp Ser
1               5                   10                  15

Lys Ala Ala His Asp Phe Val Glu Trp Leu Leu Ser Ala
            20                  25

<210> SEQ ID NO 38
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 38

His Xaa Gln Gly Thr Phe Thr Ser Asp Tyr Ser Lys Tyr Leu Asp Ser
1               5                   10                  15

Lys Ala Ala His Asp Phe Val Lys Trp Leu Leu Ser Ala
            20                  25

<210> SEQ ID NO 39
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 39

His Xaa Gln Gly Thr Phe Thr Ser Asp Tyr Ser Leu Tyr Leu Asp Ser
1               5                   10                  15

Lys Ala Ala His Asp Phe Val Glu Trp Leu Leu Ser Ala
            20                  25

<210> SEQ ID NO 40
<211> LENGTH: 29
<212> TYPE: PRT
```

```
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 40

His Xaa Gln Gly Thr Phe Thr Ser Asp Tyr Ser Lys Tyr Leu Asp Ser
1               5                   10                  15

Cys Ala Ala His Asp Phe Val Glu Trp Leu Leu Ser Ala
            20                  25

<210> SEQ ID NO 41
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 41

His Xaa Gln Gly Thr Phe Thr Ser Asp Tyr Ser Lys Tyr Leu Asp Ser
1               5                   10                  15

Lys Ala Ala Cys Asp Phe Val Glu Trp Leu Leu Arg Ala
            20                  25

<210> SEQ ID NO 42
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 42

His Xaa Gln Gly Thr Phe Thr Ser Asp Tyr Ser Lys Tyr Leu Asp Lys
1               5                   10                  15

Lys Ala Ala Glu Asp Phe Val Glu Trp Leu Leu Arg Ala
            20                  25

<210> SEQ ID NO 43
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 43

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 44
<211> LENGTH: 29
```

```
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 44

His Xaa Gln Gly Thr Phe Thr Ser Asp Tyr Ser Lys Tyr Leu Asp Ser
1               5                   10                  15

Lys Ala Ala Lys Asp Phe Val Glu Trp Leu Leu Arg Ala
            20                  25

<210> SEQ ID NO 45
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 45

His Xaa Gln Gly Thr Phe Thr Ser Asp Tyr Ser Lys Tyr Leu Asp Ser
1               5                   10                  15

Lys Ala Ala His Glu Phe Val Glu Trp Leu Leu Lys Ala
            20                  25

<210> SEQ ID NO 46
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib

<400> SEQUENCE: 46

His Xaa Gln Gly Thr Phe Thr Ser Asp Tyr Ser Lys Tyr Leu Asp Ser
1               5                   10                  15

Lys Ala Ala Lys Glu Phe Val Glu Trp Leu Leu Arg Ala
            20                  25

<210> SEQ ID NO 47
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 47

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25
```

```
<210> SEQ ID NO 48
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Lys is covalently attached to a lipophilic
      substituent

<400> SEQUENCE: 48

His Ser Gln Gly Thr Phe Thr Ser Asp Tyr Ser Lys Tyr Leu Asp Lys
1               5                   10                  15

Ala Ala His Asp Phe Val Glu Trp Leu Leu Arg Ala
            20                  25

<210> SEQ ID NO 49
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Lys is covalently attached to a lipophilic
      substituent

<400> SEQUENCE: 49

His Ser Gln Gly Thr Phe Thr Ser Asp Tyr Ser Lys Tyr Leu Asp Ser
1               5                   10                  15

Lys Ala Ala Lys Asp Phe Val Glu Trp Leu Leu Arg Ala
            20                  25

<210> SEQ ID NO 50
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (27)..(27)
<223> OTHER INFORMATION: Lys is covalently attached to a lipophilic
      substituent

<400> SEQUENCE: 50

His Ser Gln Gly Thr Phe Thr Ser Asp Tyr Ser Lys Tyr Leu Asp Ser
1               5                   10                  15

Lys Ala Ala His Asp Phe Val Glu Trp Leu Lys Arg Ala
            20                  25

<210> SEQ ID NO 51
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (28)..(28)
<223> OTHER INFORMATION: Lys is covalently attached to a lipophilic
      substituent

<400> SEQUENCE: 51

His Ser Gln Gly Thr Phe Thr Ser Asp Tyr Ser Lys Tyr Leu Asp Ser
1               5                   10                  15
```

```
Lys Ala Ala His Asp Phe Val Glu Trp Leu Leu Lys Ala
            20                  25

<210> SEQ ID NO 52
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 52

His Ser Gln Gly Thr Phe Thr Ser Asp Tyr Ser Arg Tyr Leu Asp Ser
1               5                   10                  15

Lys Ala Ala His Asp Phe Val Glu Trp Leu Leu Arg Ala
            20                  25

<210> SEQ ID NO 53
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 53

His Ser Gln Gly Thr Phe Thr Ser Asp Tyr Ser Leu Tyr Leu Asp Ser
1               5                   10                  15

Lys Ala Ala His Asp Phe Val Glu Trp Leu Leu Arg Ala
            20                  25

<210> SEQ ID NO 54
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (30)..(30)
<223> OTHER INFORMATION: Lys is covalently attached to a lipophilic
      substituent

<400> SEQUENCE: 54

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala Lys
            20                  25                  30

<210> SEQ ID NO 55
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (30)..(30)
<223> OTHER INFORMATION: Lys is covalently attached to a lipophilic
      substituent
```

<400> SEQUENCE: 55

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala Lys
            20                  25                  30

<210> SEQ ID NO 56
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (27)..(27)
<223> OTHER INFORMATION: Lys is covalently attached to a lipophilic
      substituent

<400> SEQUENCE: 56

His Ser Gln Gly Thr Phe Thr Ser Asp Tyr Ser Lys Tyr Leu Asp Ser
1               5                   10                  15

Lys Ala Ala His Asp Phe Val Glu Trp Leu Lys Ser Ala
            20                  25

<210> SEQ ID NO 57
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (24)..(24)
<223> OTHER INFORMATION: Lys is covalently attached to a lipophilic
      substituent

<400> SEQUENCE: 57

His Ser Gln Gly Thr Phe Thr Ser Asp Tyr Ser Lys Tyr Leu Asp Ser
1               5                   10                  15

Lys Ala Ala His Asp Phe Val Lys Trp Leu Leu Arg Ala
            20                  25

<210> SEQ ID NO 58
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: Cys is covalently attached to a lipophilic
      substituent

<400> SEQUENCE: 58

His Ser Gln Gly Thr Phe Thr Ser Asp Tyr Ser Lys Tyr Leu Asp Ser
1               5                   10                  15

Cys Ala Ala His Asp Phe Val Glu Trp Leu Leu Arg Ala
            20                  25

<210> SEQ ID NO 59
<211> LENGTH: 29
<212> TYPE: PRT
<213> ORGANISM: Artificial
<220> FEATURE:
<223> OTHER INFORMATION: Synthetic Construct

```
<220> FEATURE:
<221> NAME/KEY: MISC_FEATURE
<222> LOCATION: (17)..(17)
<223> OTHER INFORMATION: Cys is covalently attached to a lipophilic
      substituent

<400> SEQUENCE: 59

His Ser Gln Gly Thr Phe Thr Ser Asp Tyr Ser Lys Tyr Leu Asp Ser
1               5                   10                  15

Cys Ala Ala His Asp Phe Val Glu Trp Leu Leu Ser Ala
            20                  25

<210> SEQ ID NO 60
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Cys is covalently attached to a lipophilic
      substituent

<400> SEQUENCE: 60

His Ser Gln Gly Thr Phe Thr Ser Asp Tyr Ser Lys Tyr Leu Asp Ser
1               5                   10                  15

Lys Ala Ala Cys Asp Phe Val Glu Trp Leu Leu Arg Ala
            20                  25

<210> SEQ ID NO 61
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Lys is covalently attached to a lipophilic
      substituent

<400> SEQUENCE: 61

His Ser Gln Gly Thr Phe Thr Ser Asp Tyr Ser Lys Tyr Leu Asp Lys
1               5                   10                  15

Ser Ala Ala His Asp Phe Val Glu Trp Leu Leu Arg Ala
            20                  25

<210> SEQ ID NO 62
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (19)..(19)
<223> OTHER INFORMATION: Lys is covalently attached to a lipophilic
      substituent

<400> SEQUENCE: 62

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
```

<210> SEQ ID NO 63
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (30)..(30)
<223> OTHER INFORMATION: Lys is covalently attached to a lipophilic
      substituent

<400> SEQUENCE: 63

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala Lys
            20                  25                  30

<210> SEQ ID NO 64
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 64

His Xaa Gln Gly Thr Phe Thr Ser Asp Tyr Ser Lys Tyr Leu Asp Ser
1               5                   10                  15

Lys Ala Ala Arg Asp Phe Val Ala Trp Leu Leu Arg Ala
            20                  25

<210> SEQ ID NO 65
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (20)..(20)
<223> OTHER INFORMATION: Lys is covalently attached to a lipophilic
      substituent

<400> SEQUENCE: 65

His Xaa Gln Gly Thr Phe Thr Ser Asp Tyr Ser Lys Tyr Leu Asp Ser
1               5                   10                  15

Lys Ala Ala Lys Asp Phe Val Ala Trp Leu Leu Arg Ala
            20                  25

<210> SEQ ID NO 66

```
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (28)..(28)
<223> OTHER INFORMATION: Lys is covalently attached to a lipophilic
      substituent

<400> SEQUENCE: 66

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 67
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 67

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 68
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 68

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 69
<211> LENGTH: 29
<212> TYPE: PRT
<213> ORGANISM: Artificial
<220> FEATURE:
```

<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (20)..(20)
<223> OTHER INFORMATION: Lys is covalently attached to a lipophilic
      substituent

<400> SEQUENCE: 69

His Xaa Gln Gly Thr Phe Thr Ser Asp Tyr Ser Lys Tyr Leu Asp Ser
1               5                   10                  15

Lys Ala Ala Lys Asp Phe Val Ala Trp Leu Leu Ser Ala
            20                  25

<210> SEQ ID NO 70
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (28)..(28)
<223> OTHER INFORMATION: Lys is covalently attached to a lipophilic
      substituent

<400> SEQUENCE: 70

His Xaa Gln Gly Thr Phe Thr Ser Asp Tyr Ser Lys Tyr Leu Asp Ser
1               5                   10                  15

Lys Ala Ala His Asp Phe Val Ala Trp Leu Leu Lys Ala
            20                  25

<210> SEQ ID NO 71
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (16)..(16)
<223> OTHER INFORMATION: Lys is covalently attached to a lipophilic
      substituent

<400> SEQUENCE: 71

His Xaa Gln Gly Thr Phe Thr Ser Asp Tyr Ser Lys Tyr Leu Asp Lys
1               5                   10                  15

Lys Ala Ala His Asp Phe Val Ala Trp Leu Leu Arg Ala
            20                  25

<210> SEQ ID NO 72
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)

```
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 72

His Xaa Gln Gly Thr Phe Thr Ser Asp Tyr Ser Arg Tyr Leu Asp Ser
1               5                   10                  15

Lys Ala Ala His Asp Phe Val Glu Trp Leu Leu Ser Ala
            20                  25

<210> SEQ ID NO 73
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (24)..(24)
<223> OTHER INFORMATION: Lys is covalently attached to a lipophilic
      substituent

<400> SEQUENCE: 73

His Xaa Gln Gly Thr Phe Thr Ser Asp Tyr Ser Lys Tyr Leu Asp Ser
1               5                   10                  15

Lys Ala Ala His Asp Phe Val Lys Trp Leu Leu Ser Ala
            20                  25

<210> SEQ ID NO 74
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 74

His Xaa Gln Gly Thr Phe Thr Ser Asp Tyr Ser Leu Tyr Leu Asp Ser
1               5                   10                  15

Lys Ala Ala His Asp Phe Val Glu Trp Leu Leu Ser Ala
            20                  25

<210> SEQ ID NO 75
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
```

<223> OTHER INFORMATION: Cys is covalently attached to a lipophilic
      substituent

<400> SEQUENCE: 75

His Xaa Gln Gly Thr Phe Thr Ser Asp Tyr Ser Lys Tyr Leu Asp Ser
1               5                   10                  15

Cys Ala Ala His Asp Phe Val Glu Trp Leu Leu Ser Ala
            20                  25

<210> SEQ ID NO 76
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (20)..(20)
<223> OTHER INFORMATION: Cys is covalently attached to a lipophilic
      substituent

<400> SEQUENCE: 76

His Xaa Gln Gly Thr Phe Thr Ser Asp Tyr Ser Lys Tyr Leu Asp Ser
1               5                   10                  15

Lys Ala Ala Cys Asp Phe Val Glu Trp Leu Leu Arg Ala
            20                  25

<210> SEQ ID NO 77
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (16)..(16)
<223> OTHER INFORMATION: Ser is covalently attached to a lipophilic
      substituent

<400> SEQUENCE: 77

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 78
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (16)..(16)
<223> OTHER INFORMATION: Lys is covalently attached to a lipophilic
      substituent

<400> SEQUENCE: 78

```
His Gln Gly Thr Phe Thr Ser Asp Tyr Ser Lys Tyr Leu Asp Lys Lys
1               5                   10                  15

Ala Ala Glu Asp Phe Val Glu Trp Leu Leu Arg Ala
            20                  25
```

<210> SEQ ID NO 79
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 79

```
His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25
```

<210> SEQ ID NO 80
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: Lys is covalently attached to a lipophilic
      substituent

<400> SEQUENCE: 80

```
His Xaa Gln Gly Thr Phe Thr Ser Asp Tyr Ser Lys Tyr Leu Asp Ser
1               5                   10                  15

Lys Ala Ala Lys Asp Phe Val Glu Trp Leu Leu Arg Ala
            20                  25
```

<210> SEQ ID NO 81
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (28)..(28)
<223> OTHER INFORMATION: Lys is covalently attached to a lipophilic
      substituent

<400> SEQUENCE: 81

```
His Xaa Gln Gly Thr Phe Thr Ser Asp Tyr Ser Lys Tyr Leu Asp Ser
1               5                   10                  15
```

Lys Ala Ala His Glu Phe Val Glu Trp Leu Leu Lys Ala
            20                  25

<210> SEQ ID NO 82
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (20)..(20)
<223> OTHER INFORMATION: Lys is covalently attached to a lipophilic
      substituent

<400> SEQUENCE: 82

His Xaa Gln Gly Thr Phe Thr Ser Asp Tyr Ser Lys Tyr Leu Asp Ser
1               5                   10                  15

Lys Ala Ala Lys Glu Phe Val Glu Trp Leu Leu Arg Ala
            20                  25

<210> SEQ ID NO 83
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: K(Hexadecanoyl-gamma-Glu)

<400> SEQUENCE: 83

His Ser Gln Gly Thr Phe Thr Ser Asp Tyr Ser Lys Tyr Leu Asp Lys
1               5                   10                  15

Lys Ala Ala His Asp Phe Val Glu Trp Leu Leu Arg Ala
            20                  25

<210> SEQ ID NO 84
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (27)..(27)
<223> OTHER INFORMATION: K(HEXADECANOYL-gamma-GLU)

<400> SEQUENCE: 84

His Ser Gln Gly Thr Phe Thr Ser Asp Tyr Ser Lys Tyr Leu Asp Ser
1               5                   10                  15

Lys Ala Ala His Asp Phe Val Glu Trp Leu Lys Arg Ala
            20                  25

<210> SEQ ID NO 85
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: K(HEXADECANOYL-gamma-GLU)

<400> SEQUENCE: 85

His Ser Gln Gly Thr Phe Thr Ser Asp Tyr Ser Lys Tyr Leu Asp Ser
1               5                   10                  15

Lys Ala Ala Lys Asp Phe Val Glu Trp Leu Leu Arg Ala
            20                  25

<210> SEQ ID NO 86
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (28)..(28)
<223> OTHER INFORMATION: K(HEXADECANOYL-gamma-GLU)

<400> SEQUENCE: 86

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 87
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-gamma-GLU)

<400> SEQUENCE: 87

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 88
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-gamma-GLU)

<400> SEQUENCE: 88

His Xaa Gln Gly Thr Phe Thr Ser Asp Tyr Ser Lys Tyr Leu Asp Ser
1               5                   10                  15

Lys Ala Ala Arg Asp Phe Val Ala Trp Leu Leu Arg Ala
            20                  25

<210> SEQ ID NO 89

```
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-gamma-GLU)

<400> SEQUENCE: 89

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 90
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (28)..(28)
<223> OTHER INFORMATION: K(HEXADECANOYL-gamma-GLU)

<400> SEQUENCE: 90

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 91
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-gamma-GLU)

<400> SEQUENCE: 91

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 92
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
```

```
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-gamma-GLU)

<400> SEQUENCE: 92

His Xaa Gln Gly Thr Phe Thr Ser Asp Tyr Ser Lys Tyr Leu Asp Ser
1               5                   10                  15
Lys Ala Ala His Asp Phe Val Glu Trp Leu Leu Lys Ala
            20                  25

<210> SEQ ID NO 93
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K(HEXADECANOYL-gamma-GLU)

<400> SEQUENCE: 93

His Ser Gln Gly Thr Phe Thr Ser Asp Tyr Ser Lys Tyr Leu Asp Ser
1               5                   10                  15
Lys Ala Ala His Asp Phe Val Glu Trp Leu Leu Arg Ala
            20                  25

<210> SEQ ID NO 94
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (20)..(20)
<223> OTHER INFORMATION: K(HEXADECANOYL-gamma-GLU)

<400> SEQUENCE: 94

His Xaa Gln Gly Thr Phe Thr Ser Asp Tyr Ser Lys Tyr Leu Asp Ser
1               5                   10                  15
Lys Ala Ala Lys Asp Phe Val Ala Trp Leu Leu Arg Ala
            20                  25

<210> SEQ ID NO 95
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(DODECANOYL-gamma-GLU)

<400> SEQUENCE: 95

His Xaa Gln Gly Thr Phe Thr Ser Asp Tyr Ser Lys Tyr Leu Asp Ser
1               5                   10                  15
```

Lys Ala Ala His Asp Phe Val Glu Trp Leu Leu Ser Ala
            20                  25

<210> SEQ ID NO 96
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-[3-AMINOPROPANOYL])

<400> SEQUENCE: 96

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 97
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-[8-AMINOOCTANOYL])

<400> SEQUENCE: 97

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 98
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-epsilon-LYS)

<400> SEQUENCE: 98

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 99
<211> LENGTH: 29

```
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K(HEXADECANOYL)

<400> SEQUENCE: 99

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 100
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K(OCTADECANOYL-gamma-GLU)

<400> SEQUENCE: 100

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 101
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K([2-BUTYLOCTANOYL]-gamma-GLU)

<400> SEQUENCE: 101

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 102
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K(HEXADECANOYL-[4-AMINOBUTANOYL])

<400> SEQUENCE: 102

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 103
```

<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K(OCTADECANOYL-gamma-GLU)

<400> SEQUENCE: 103

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 104
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: K(HEXADECANOYL-E)

<400> SEQUENCE: 104

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 105
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL)

<400> SEQUENCE: 105

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 106
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 Aib
<220> FEATURE:
<221> NAME/KEY: MISC_FEATURE
<222> LOCATION: (17)..(17)
<223> OTHER INFORMATION: K(OCTADECANOYL-gamma-GLU)

<400> SEQUENCE: 106

```
His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25
```

<210> SEQ ID NO 107
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K([2-BUTYLOCTANOYL]-gamma-GLU)

<400> SEQUENCE: 107

```
His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25
```

<210> SEQ ID NO 108
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-[4-AMINOBUTANOYL])

<400> SEQUENCE: 108

```
His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25
```

<210> SEQ ID NO 109
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(OCTADECANOYL-gamma-GLU)

<400> SEQUENCE: 109

```
His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25
```

<210> SEQ ID NO 110
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-E)

<400> SEQUENCE: 110

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 111
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (12)..(12)
<223> OTHER INFORMATION: K(HEXADECANOYL-ISOGLU)

<400> SEQUENCE: 111

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 112
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (16)..(16)
<223> OTHER INFORMATION: K(HEXADECANOYL-ISOGLU)

<400> SEQUENCE: 112

His Xaa Gln Gly Thr Phe Thr Ser Asp Tyr Ser Lys Tyr Leu Asp Lys
1               5                   10                  15

Lys Ala Ala His Asp Phe Val Glu Trp Leu Leu Ser Ala
            20                  25

<210> SEQ ID NO 113
<211> LENGTH: 29
<212> TYPE: PRT
<213> ORGANISM: Artificial
<220> FEATURE:
<223> OTHER INFORMATION: Synthetic Construct

```
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (20)..(20)
<223> OTHER INFORMATION: K(HEXADECANOYL-ISOGLU)

<400> SEQUENCE: 113

His Xaa Gln Gly Thr Phe Thr Ser Asp Tyr Ser Lys Tyr Leu Asp Ser
1               5                   10                  15

Lys Ala Ala Lys Asp Phe Val Glu Trp Leu Leu Ser Ala
            20                  25

<210> SEQ ID NO 114
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (24)..(24)
<223> OTHER INFORMATION: K(HEXADECANOYL-ISOGLU)

<400> SEQUENCE: 114

His Xaa Gln Gly Thr Phe Thr Ser Asp Tyr Ser Lys Tyr Leu Asp Ser
1               5                   10                  15

Lys Ala Ala His Asp Phe Val Lys Trp Leu Leu Ser Ala
            20                  25

<210> SEQ ID NO 115
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (16)..(16)
<223> OTHER INFORMATION: K(HEXADECANOYL-ISOLYS)

<400> SEQUENCE: 115

His Gln Gly Thr Phe Thr Ser Asp Tyr Ser Lys Tyr Leu Asp Ser Lys
1               5                   10                  15

Ala Ala Arg Asp Phe Val Ala Trp Leu Leu Arg Ala
            20                  25

<210> SEQ ID NO 116
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
```

<223> OTHER INFORMATION: K(HEXADECANOYL-ISOGLU)

<400> SEQUENCE: 116

His Xaa Gln Gly Thr Phe Thr Ser Asp Tyr Ser Lys Tyr Leu Asp Ser
1               5                   10                  15

Lys Ala Ala Lys Asp Phe Val Glu Trp Leu Leu Ser Ala
            20                  25

<210> SEQ ID NO 117
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 117

His Xaa Gln Gly Thr Phe Thr Ser Asp Tyr Ser Lys Tyr Leu Asp Glu
1               5                   10                  15

Lys Ala Ala His Asp Phe Val Glu Trp Leu Leu Ser Ala
            20                  25

<210> SEQ ID NO 118
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 118

His Xaa Gln Gly Thr Phe Thr Ser Asp Tyr Ser Lys Tyr Leu Asp Ser
1               5                   10                  15

Lys Ala Ala His Glu Phe Val Glu Trp Leu Leu Ser Ala
            20                  25

<210> SEQ ID NO 119
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 119

His Xaa Gln Gly Thr Phe Thr Ser Asp Tyr Ser Lys Tyr Leu Asp Ser
1               5                   10                  15

Lys Ala Ala Glu Asp Phe Val Glu Trp Leu Leu Ser Ala
            20                  25

<210> SEQ ID NO 120
<211> LENGTH: 29
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 120

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Glu Ala
            20                  25

<210> SEQ ID NO 121
<211> LENGTH: 28
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 121

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser
            20                  25

<210> SEQ ID NO 122
<211> LENGTH: 27
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 122

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu
            20                  25

<210> SEQ ID NO 123
<211> LENGTH: 29
<212> TYPE: PRT

<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 123

His Xaa Glu Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 124
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOGLU)

<400> SEQUENCE: 124

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 125
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K([2-BUTYLOCTANOYL]-ISOGLU)

<400> SEQUENCE: 125

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 126
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(OCTADECANOYL-ISOGLU)

<400> SEQUENCE: 126

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 127
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(DODECANOYL-ISOGLU)

<400> SEQUENCE: 127

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 128
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: K(HEXADECANOYL-ISOLYS)

<400> SEQUENCE: 128

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 129
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MOD_RES
<222> LOCATION: (17)..(17)
<223> OTHER INFORMATION: Orn
<220> FEATURE:
<221> NAME/KEY: MISC_FEATURE
<222> LOCATION: (17)..(17)

```
<223> OTHER INFORMATION: ORN(HEXADECANOYL-ISOGLU)

<400> SEQUENCE: 129

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Leu Ser Ala
            20                  25

<210> SEQ ID NO 130
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (28)..(28)
<223> OTHER INFORMATION: K(HEXADECANOYL-ISOGLU)

<400> SEQUENCE: 130

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Lys Ala
            20                  25

<210> SEQ ID NO 131
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: X2 is Aib
<220> FEATURE:
<221> NAME/KEY: MISC_FEATURE
<222> LOCATION: (17)..(17)
<223> OTHER INFORMATION: X17 is selected from Glu, Lys, or Cys,
      covalently attached to a lipophilic substituent

<400> SEQUENCE: 131

His Xaa Glu Gly Thr Phe Thr Ser Asp Tyr Ser Lys Tyr Leu Asp Ser
1               5                   10                  15

Xaa Ala Ala His Asp Phe Val Gly Trp Leu Leu Ser Ala
            20                  25
```

ACYLATED GLUCAGON ANALOGUES

FIELD OF THE INVENTION

The present invention relates to acylated glucagon analogues and their medical use, for example in the treatment of obesity and diabetes.

BACKGROUND OF THE INVENTION

Obesity and diabetes are globally increasing health problems and are associated with various diseases, particularly cardiovascular disease (CVD), obstructive sleep apnea, stroke, peripheral artery disease, microvascular complications and osteoarthritis.

There are 246 million people worldwide with diabetes, and by 2025 it is estimated that 380 million will have diabetes. Many have additional cardiovascular risk factors including high/aberrant LDL and triglycerides and low HDL.

Cardiovascular disease accounts for about 50% of the mortality in people with diabetes and the morbidity and mortality rates relating to obesity and diabetes underscore the medical need for efficacious treatment options.

Preproglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO:1). Oxyntomodulin (OXM) is a 37 amino acid peptide which includes the complete 29 amino acid sequence of glucagon with an octapeptide carboxyterminal extension (amino acids 82 to 89 of pre-proglucagon, having the sequence Lys-Arg-Asn-Arg-Asn-Asn-Ile-Ala (SEQ ID NO:2) and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala (SEQ ID NO:3). The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia. Additionally, glucagon has been demonstrated to increase lipolysis and decrease body weight.

GLP-1 decreases elevated blood glucose levels by improving glucose-stimulated insulin secretion and promotes weight loss chiefly through decreasing food intake.

Oxyntomodulin is released into the blood in response to food ingestion and in proportion to meal calorie content. The mechanism of action of oxyntomodulin is not well understood. In particular, it is not known whether the effects of the hormone are mediated exclusively through the glucagon receptor and the GLP-1 receptor, or through one or more as-yet unidentified receptors.

Other peptides have been shown to bind and activate both the glucagon and the GLP-1 receptor (Hjort et al, Journal of Biological Chemistry, 269, 30121-30124, 1994) and to suppress body weight gain and reduce food intake (WO 2006/134340; WO 2007/100535; WO 2008/101017, WO 2008/152403, WO 2009/155257 and WO 2009/155258).

Stabilization of peptides has been shown to provide a better pharmacokinetic profile for several drugs. In particular addition of one or more polyethylene glycol (PEG) or acyl group has been shown to prolong half-life of peptides such as GLP-1 and other peptides with short plasma stability In WO 00/55184A1 and WO 00/55119 are disclosed methods for acylation of a range of peptides, in particular GLP-1. Madsen et al (J. Med. Chem. 2007, 50, 6126-6132) describe GLP-1 acylated at position 20 (Liraglutide) and provide data on its stability.

Stabilization of OXM by PEGylation and C-terminal acylation has also been shown to improve the pharmacokinetic profile of selected analogues in WO2007/100535, WO08/071972 and in Endocrinology 2009, 150(4), 1712-1721 by Druce, M R et al.

It has recently been shown that PEGylation of glucagon analogues has a significant effect on the pharmacokinetic profile of the tested compounds (WO2008/101017) but also interferes with the potency of these compounds.

SUMMARY OF THE INVENTION

The invention provides a compound having the formula:

$$R^1\text{—}Z\text{—}R^2$$

wherein $R^1$ is H, $C_{1-4}$ alkyl, acetyl, formyl, benzoyl or trifluoroacetyl;

$R^2$ is OH or $NH_2$;

and Z is a peptide having the formula I (I)
(SEQ ID NO: 4)
His-X2-Gln-Gly-Thr-Phe-Thr-Ser-Asp-Tyr-Ser-X12-

Tyr-Leu-Asp-X16-X17-Ala-Ala-X20-X21-Phe-Val-X24-

Trp-Leu-X27-X28-Ala-X30;

wherein
X2 is selected from Aib or Ser;
X12 is selected from Lys, Arg and Leu;
X16 is selected from Arg and X;
X17 is selected from Arg and X;
X20 is selected from Arg, His and X;
X21 is selected from Asp and Glu;
X24 is selected from Ala and X;
X27 is selected from Leu and X;
X28 is selected from Arg and X;
X30 is X or is absent;
wherein at least one of X16, X17, X20, X24, X27, X28, and X30 is X;
and wherein each residue X is independently selected from the group consisting of Glu, Lys, Ser, Cys, Dbu, Dpr and Orn;

wherein the side chain of at least one residue X is conjugated to a lipophilic substituent having the formula:

$$Z^1, \quad (i)$$

wherein $Z^1$ is a lipophilic moiety conjugated directly to the side chain of X; or $$Z^1 Z^2, \quad (ii)$$

wherein $Z^1$ is a lipophilic moiety, $Z^2$ is a spacer, and $Z^1$ is conjugated to the side chain of X via $Z^2$;
with the proviso that Z is not HSQGTFTSDYSKYLDS-K(Hexadecanoyl-γ-Glu)-AAHDFVEWLLRA (SEQ ID NO:5).

X30 may be present or absent. In those embodiments when X30 is present, it may be desirable for it to be Lys.

In certain embodiments, any residue X, and especially any residue X which is conjugated to a lipophilic substituent, is independently selected from Lys, Glu or Cys.

In certain embodiments,
X16 is selected from Glu, Lys and Ser;
X17 is selected from Lys and Cys;
X20 is selected from His, Lys, Arg and Cys;
X24 is selected from Lys, Glu and Ala;
X27 is selected from Leu and Lys; and/or
X28 is selected from Ser, Arg and Lys.

Specific combinations of residues which may be present in the peptide of formula I include the following:
X2 is Aib and X17 is Lys;
X2 is Aib and X17 is Cys;
X2 is Aib and X20 is Cys;
X2 is Aib and X28 is Lys;
X12 is Arg and X17 is Lys;
X12 is Leu and X17 is Lys;
X12 is Lys and X20 is Lys;
X12 is Lys and X17 is Lys;
X16 is Lys and X17 is Lys;
X16 is Ser and X17 is Lys;
X17 is Lys and X20 is Lys;
X17 is Lys and X21 is Asp;
X17 is Lys and X24 is Glu;
X17 is Lys and X27 is Leu;
X17 is Lys and X27 is Lys;
X17 is Lys and X28 is Ser;
X17 is Lys and X28 is Arg;
X20 is Lys and X27 is Leu;
X21 is Asp and X27 is Leu;
X2 is Aib, X12 is Lys and X16 is Ser;
X12 is Lys, X17 is Lys and X16 is Ser;
X12 is Arg, X17 is Lys and X16 is Glu;
X16 is Glu, X17 is Lys and X20 is Lys;
X16 is Ser, X21 is Asp and X24 is Glu;
X17 is Lys, X24 is Glu and X28 is Arg;
X17 is Lys, X24 is Glu and X28 is Lys;
X17 is Lys, X27 is Leu and X28 is Ser;
X17 is Lys, X27 is Leu and X28 is Arg;
X20 is Lys, X24 is Glu and X27 is Leu;
X20 is Lys, X27 is Leu and X28 is Ser;
X20 is Lys, X27 is Leu and X28 is Arg;
X16 is Ser, X20 is His, X24 is Glu and X27 is Leu;
X17 is Lys, X20 is His, X24 is Glu and X28 is Ser;
X17 is Lys, X20 is Lys, X24 is Glu and X27 is Leu; or
X17 is Cys, X20 is Lys, X24 is Glu and X27 is Leu.

It may be desirable that the peptide of formula I contains only one amino acid of the type which is to be derivatised by addition of the lipophilic substituent. For example, the peptide may contain only one Lys residue, only one Cys residue or only one Glu residue for the lipophilic substituent to be conjugated to that residue.

The compounds of the invention may carry one or more intramolecular bridge within the peptide sequence of formula I. Each such bridge is formed between the side chains of two amino acid residues of formula I which are typically separated by three amino acids in the linear amino acid sequence (i.e. between amino acid A and amino acid A+4).

More particularly, the bridge may be formed between the side chains of residue pairs 16 and 20, 17 and 21, 20 and 24, or 24 and 28. The two side chains can be linked to one another through ionic interactions, or by covalent bonds. Thus these pairs of residues may comprise oppositely charged side chains in order to form a salt bridge by ionic interactions. For example, one of the residues may be Glu or Asp, while the other may be Lys or Arg. The pairings of Lys and Glu and Lys and Asp, may also be capable of reacting to form a lactam ring.

Examples of suitable pairs of residues at positions 16 and 20 include:
X16 is Glu and X20 is Lys;
X16 is Glu and X20 is Arg;
X16 is Lys and X20 is Glu; and
X16 is Arg and X20 is Glu.

Examples of suitable pairs of residues at positions 17 and 21 include:
X17 is Arg and X21 is Glu;
X17 is Lys and X21 is Glu;
X17 is Arg and X21 is Asp; and
X17 is Lys and X21 is Asp.

Examples of suitable pairs of residues at positions 20 and 24 include:
X20 is Glu and X24 is Lys;
X20 is Glu and X24 is Arg;
X20 is Lys and X24 is Glu; and
X20 is Arg and X24 is Glu.

Examples of suitable pairs of residues at positions 24 and 28 include:
X24 is Glu and X28 is Lys;
X24 is Glu and X28 is Arg;
X24 is Lys and X28 is Glu; and
X24 is Arg and X28 is Glu.

The pairing of Lys and Glu, e.g. to form a lactam ring, may be particularly desirable, especially between positions 24 and 28.

It will be apparent that a residue involved in an intramolecular bridge cannot also be derivatised with a lipophilic substituent. Thus, when a residue X is involved in an intramolecular bridge, at least one of the other residues X is conjugated to a lipophilic substituent or substituents.

Without wishing to be bound by any particular theory, it is believed that such intramolecular bridges stabilise the alpha helical structure of the molecule and so increase potency and/or selectivity at the GLP-1 receptor and possibly also the glucagon receptor.

The compound may have the formula:

$$R^1 - Z - R^2$$

wherein $R^1$ is H, $C_{1-4}$ alkyl, acetyl, formyl, benzoyl or trifluoroacetyl;

$R^2$ is OH or $NH_2$;
and Z is a peptide having the formula IIa (IIa)
(SEQ ID NO: 6)
His-Aib-Gln-Gly-Thr-Phe-Thr-Ser-Asp-Tyr-Ser-X12-

Tyr-Leu-Asp-X16-X17-Ala-Ala-X20-X21-Phe-Val-X24-

Trp-Leu-Leu-X28-Ala;

wherein
X12 is selected from Lys, Arg and Leu;
X16 is selected from Ser and X;
X17 is X;
X20 is selected from His and X;
X21 is selected from Asp and Glu;
X24 is selected from Ala and Glu;
X28 is selected from Ser, Lys and Arg;
and wherein each residue X is independently selected from the group consisting of Glu, Lys, and Cys;
wherein the side chain of at least one residue X is conjugated to a lipophilic substituent having the formula:

$Z^1$, (i)

wherein $Z^1$ is a lipophilic moiety conjugated directly to the side chain of X; or $Z^1Z^2$, (ii)

wherein $Z^1$ is a lipophilic moiety, $Z^2$ is a spacer, and $Z^1$ is conjugated to the side chain of X via $Z^2$.

Alternatively, the compound may have the formula:

$R^1$—Z—$R^2$ wherein $R^1$ is H, $C_{1-4}$ alkyl, acetyl, formyl, benzoyl or trifluoroacetyl;
$R^2$ is OH or $NH_2$;
and Z is a peptide having the formula IIb (IIb)
(SEQ ID NO: 7)
His-Ser-Gln-Gly-Thr-Phe-Thr-Ser-Asp-Tyr-Ser-X12-

Tyr-Leu-Asp-X16-X17-Ala-Ala-X20-X21-Phe-Val-X24-

Trp-Leu-Leu-X28-Ala;

wherein
X12 is selected from Lys, Arg and Leu;
X16 is selected from Ser and X;
X17 is X;
X20 is selected from His and X;
X21 is selected from Asp and Glu;
X24 is selected from Ala and Glu;
X28 is selected from Ser, Lys and Arg;
and wherein each residue X is independently selected from the group consisting of Glu, Lys, and Cys;
wherein the side chain of at least one residue X is conjugated to a lipophilic substituent having the formula:

$Z^1$, (i)

wherein $Z^1$ is a lipophilic moiety conjugated directly to the side chain of X; or $Z^1Z^2$, (ii)

wherein $Z^1$ is a lipophilic moiety, $Z^2$ is a spacer, and $Z^1$ is conjugated to the side chain of X via $Z^2$;

with the proviso that Z is not HSQGTFTSDYSKYLDS-K(Hexadecanoyl-γ-Glu))-AAHDFVEWLLRA (SEQ ID NO:5).

The compound may have the formula:

$R^1$—Z—$R^2$ wherein $R^1$ is H, $C_{1-4}$ alkyl, acetyl, formyl, benzoyl or trifluoroacetyl;
$R^2$ is OH or $NH_2$;
and Z is a peptide having the formula IIIa (IIIa)
(SEQ ID NO: 8)
His-Aib-Gln-Gly-Thr-Phe-Thr-Ser-Asp-Tyr-Ser-X12-

Tyr-Leu-Asp-Ser-X17-Ala-Ala-X20-X21-Phe-

Val-X24-Trp-Leu-Leu-X28-Ala;

wherein
X12 is selected from Lys and Arg;
X17 is X;
X20 is selected from His and X;
X21 is selected from Asp and Glu;
X24 is selected from Ala and Glu;
X28 is selected from Ser, Lys and Arg;
and wherein each residue X is independently selected from Glu, Lys, and Cys;
wherein the side chain of at least one residue X is conjugated to a lipophilic substituent having the formula:

$Z^1$, (i)

wherein $Z^1$ is a lipophilic moiety conjugated directly to the side chain of X; or $Z^1Z^2$, (ii)

wherein $Z^1$ is a lipophilic moiety, $Z^2$ is a spacer, and $Z^1$ is conjugated to the side chain of X via $Z^2$.

Alternatively the compound may have the formula:

$R^1$—Z—$R^2$ wherein $R^1$ is H, $C_{1-4}$ alkyl, acetyl, formyl, benzoyl or trifluoroacetyl;
$R^2$ is OH or $NH_2$;
and Z is a peptide having the formula IIIb (IIIb)
(SEQ ID NO: 9)
His-Ser-Gln-Gly-Thr-Phe-Thr-Ser-Asp-Tyr-Ser-X12-

Tyr-Leu-Asp-Ser-X17-Ala-Ala-X20-X21-Phe-

Val-X24-Trp-Leu-Leu-X28-Ala;

wherein
X12 is selected from Lys or Arg;
X17 is X;
X20 is selected from His and X;
X21 is selected from Asp and Glu;
X24 is selected from Ala and Glu;
X28 is selected from Ser, Lys and Arg;
and wherein each residue X is independently selected from Glu, Lys, and Cys;
wherein the side chain of at least one residue X is conjugated to a lipophilic substituent having the formula:

$Z^1$, (i)

wherein $Z^1$ is a lipophilic moiety conjugated directly to the side chain of X; or $$Z^1Z^2, \quad (ii)$$

wherein $Z^1$ is a lipophilic moiety, $Z^2$ is a spacer, and $Z^1$ is conjugated to the side chain of X via $Z^2$;
with the proviso that Z is not HSQGTFTSDYSKYLDS-K (Hexadecanoyl-γ-Glu))-AAHDFVEWLLRA (SEQ ID NO:5).

The compound may have the formula:

$$R^1\text{---}Z\text{---}R^2$$

wherein $R^1$ is H, $C_{1-4}$ alkyl, acetyl, formyl, benzoyl or trifluoroacetyl;
$R^2$ is OH or $NH_2$;
and Z is a peptide having the formula IVa His-Aib-Gln-Gly-Thr-Phe-Thr-Ser-Asp-Tyr-Ser-X12-
Tyr-Leu-Asp-Ser-X17-Ala-Ala-His-X21-Phe-
Val-X24-Trp-Leu-Leu-X28-Ala; (SEQ ID
NO:10)     (IVa)

wherein
X12 is selected from Lys and Arg;
X17 is X;
X21 is selected from Asp and Glu;
X24 is selected from Ala and Glu;
X28 is selected from Ser, Lys and Arg;
wherein X is selected from the group consisting of Glu, Lys, and Cys;
and wherein the side chain of X is conjugated to a lipophilic substituent having the formula:

$$Z^1, \quad (i)$$

wherein $Z^1$ is a lipophilic moiety conjugated directly to the side chain of X; or $$Z^1Z^2, \quad (ii)$$

wherein $Z^1$ is a lipophilic moiety, $Z^2$ is a spacer, and $Z^1$ is conjugated to the side chain of X via $Z^2$.

Alternatively the compound may have the formula:

$$R^1\text{---}Z\text{---}R^2$$

wherein $R^1$ is H, $C_{1-4}$ alkyl, acetyl, formyl, benzoyl or trifluoroacetyl;
$R^2$ is OH or $NH_2$;
and Z is a peptide having the formula IVb (IVb)
    (SEQ ID NO: 11)
His-Ser-Gln-Gly-Thr-Phe-Thr-Ser-Asp-Tyr-Ser-X12-

Tyr-Leu-Asp-Ser-X17-Ala-Ala-His-X21-Phe-Val-

X24-Trp-Leu-Leu-X28-Ala;

wherein
X12 is selected from Lys and Arg;
X17 is X;
X21 is selected from Asp and Glu;
X24 is selected from Ala and Glu
X28 is selected from Ser, Lys and Arg;
wherein X is selected from the group consisting of Glu, Lys, and Cys;
and wherein the side chain of X is conjugated to a lipophilic substituent having the formula:

$$Z^1, \quad (i)$$

wherein $Z^1$ is a lipophilic moiety conjugated directly to the side chain of X; or $$Z^1Z^2, \quad (ii)$$

wherein $Z^1$ is a lipophilic moiety, $Z^2$ is a spacer, and $Z^1$ is conjugated to the side chain of X via $Z^2$;
with the proviso that Z is not HSQGTFTSDYSKYLDS-K (Hexadecanoyl-γ-Glu))-AAHDFVEWLLRA (SEQ ID NO:5).

Alternatively the compound may have the formula:

$$R^1\text{---}Z\text{---}R^2$$

wherein $R^1$ is H, $C_{1-4}$ alkyl, acetyl, formyl, benzoyl or trifluoroacetyl;
$R^2$ is OH or $NH_2$;
and Z is a peptide having the formula V (V)
    (SEQ ID NO: 12)
His-Aib-Gln-Gly-Thr-Phe-Thr-Ser-Asp-Tyr-Ser-Lys- Tyr-Leu-Asp-Ser-Lys-Ala-Ala-His-Asp-Phe-Val- Glu-Trp-Leu-Leu-X28;

wherein
X28 is Ser or absent;
X17 is X
wherein X is selected from the group consisting of Glu, Lys, and Cys;
and wherein the side chain of X is conjugated to a lipophilic substituent having the formula:

$$Z^1, \quad (i)$$

wherein $Z^1$ is a lipophilic moiety conjugated directly to the side chain of X; or $$Z^1Z^2, \quad (ii)$$

wherein $Z^1$ is a lipophilic moiety, $Z^2$ is a spacer, and $Z^1$ is conjugated to the side chain of X via $Z^2$;

In certain embodiments of the invention, the peptide of formula I may have the sequence:

```
                                   (SEQ ID NO: 13)
HSQGTFTSDYSKYLDSKAAHDFVEWLLRA;

(SEQ ID NO: 14)
HSQGTFTSDYSKYLDKKAAHDFVEWLLRA;

(SEQ ID NO: 15)
HSQGTFTSDYSKYLDSKAAKDFVEWLLRA;

(SEQ ID NO: 16)
HSQGTFTSDYSKYLDSKAAHDFVEWLKRA;

(SEQ ID NO: 17)
HSQGTFTSDYSKYLDSKAAHDFVEWLLKA;

(SEQ ID NO: 18)
HSQGTFTSDYSRYLDSKAAHDFVEWLLRA;

(SEQ ID NO: 19)
HSQGTFTSDYSLYLDSKAAHDFVEWLLRA;

(SEQ ID NO: 20)
HSQGTFTSDYSKYLDSKAAHDFVEWLLSAK;

(SEQ ID NO: 21)
HSQGTFTSDYSKYLDSKAAHDFVEWLLSAK;

(SEQ ID NO: 22)
HSQGTFTSDYSKYLDSKAAHDFVEWLKSA;
```

```
                                      (SEQ ID NO: 23)
HSQGTFTSDYSKYLDSKAAHDFVKWLLRA;

(SEQ ID NO: 24)
HSQGTFTSDYSKYLDSCAAHDFVEWLLRA;

(SEQ ID NO: 25)
HSQGTFTSDYSKYLDSCAAHDFVEWLLSA;

(SEQ ID NO: 26)
HSQGTFTSDYSKYLDSKAACDFVEWLLRA;

(SEQ ID NO: 27)
HSQGTFTSDYSKYLDKSAAHDFVEWLLRA;

(SEQ ID NO: 28)
H-Aib-QGTFTSDYSKYLDSKAAHDFVEWLLSA;

(SEQ ID NO: 29)
H-Aib-QGTFTSDYSKYLDSKAAHDFVEWLLSAK;

(SEQ ID NO: 30)
H-Aib-QGTFTSDYSKYLDSKAARDFVAWLLRA;

(SEQ ID NO: 31)
H-Aib-QGTFTSDYSKYLDSKAAKDFVAWLLRA;

(SEQ ID NO: 32)
H-Aib-QGTFTSDYSKYLDSKAAHDFVEWLLRA;

(SEQ ID NO: 33)
H-Aib-QGTFTSDYSKYLDSKAAHDFVEWLLKA;

(SEQ ID NO: 34)
H-Aib-QGTFTSDYSKYLDSKAAKDFVAWLLSA;

(SEQ ID NO: 35)
H-Aib-QGTFTSDYSKYLDSKAAHDFVAWLLKA;

(SEQ ID NO: 36)
H-Aib-QGTFTSDYSKYLDKKAAHDFVAWLLRA;

(SEQ ID NO: 37)
H-Aib-QGTFTSDYSRYLDSKAAHDFVEWLLSA;

(SEQ ID NO: 38)
H-Aib-QGTFTSDYSKYLDSKAAHDFVKWLLSA;

(SEQ ID NO: 39)
H-Aib-QGTFTSDYSLYLDSKAAHDFVEWLLSA;

(SEQ ID NO: 40)
H-Aib-QGTFTSDYSKYLDSCAAHDFVEWLLSA;

(SEQ ID NO: 41)
H-Aib-QGTFTSDYSKYLDSKAACDFVEWLLRA;

(SEQ ID NO: 42)
H-Aib-QGTFTSDYSKYLDK( )KAAE( )DFVEWLLRA;

(SEQ ID NO: 43)
H-Aib-QGTFTSDYSKYLDSKAAHDFVE( )WLLK( )A;

(SEQ ID NO: 44)
H-Aib-QGTFTSDYSKYLDSKAAK( )DFVE( )WLLRA;

(SEQ ID NO: 45)
H-Aib-QGTFTSDYSKYLDSK( )AAHE( )FVEWLLKA;
or (SEQ ID NO: 46)
H-Aib-QGTFTSDYSKYLDSK( )AAKE( )FVEWLLRA.
```

In certain embodiments these peptides may carry a lipohilic substituent at the position marked "*" as follows:

```
                                      (SEQ ID NO: 47)
HSQGTFTSDYSKYLDS-K*-AAHDFVEWLLRA;

(SEQ ID NO: 48)
HSQGTFTSDYSKYLD-K*-KAAHDFVEWLLRA;

(SEQ ID NO: 49)
HSQGTFTSDYSKYLDSKAA-K*-DFVEWLLRA;

(SEQ ID NO: 50)
HSQGTFTSDYSKYLDSKAAHDFVEWL-K*-RA;

(SEQ ID NO: 51)
HSQGTFTSDYSKYLDSKAAHDFVEWLL-K*-A;

(SEQ ID NO: 52)
HSQGTFTSDYSRYLDS-K*-AAHDFVEWLLRA;

(SEQ ID NO: 53)
HSQGTFTSDYSLYLDS-K*-AAHDFVEWLLRA;

(SEQ ID NO: 54)
HSQGTFTSDYSKYLDSKAAHDFVEWLLRA-K*;

(SEQ ID NO: 55)
HSQGTFTSDYSKYLDSKAAHDFVEWLLSA-K*;

(SEQ ID NO: 56)
HSQGTFTSDYSKYLDSKAAHDFVEWL-K*-SA;

(SEQ ID NO: 57)
HSQGTFTSDYSKYLDSKAAHDFV-K*-WLLRA;

(SEQ ID NO: 58)
HSQGTFTSDYSKYLDS-C*-AAHDFVEWLLRA;

(SEQ ID NO: 59)
HSQGTFTSDYSKYLDS-C*-AAHDFVEWLLSA;

(SEQ ID NO: 60)
HSQGTFTSDYSKYLDSKAA-C*-DFVEWLLRA;

(SEQ ID NO: 61)
HSQGTFTSDYSKYLD-K*-SAAHDFVEWLLRA;

(SEQ ID NO: 62)
H-Aib-QGTFTSDYSKYLDS-K*-AAHDFVEWLLSA;

(SEQ ID NO: 63)
H-Aib-QGTFTSDYSKYLDSKAAHDFVEWLLSA-K*;

(SEQ ID NO: 64)
H-Aib-QGTFTSDYSKYLDS-K*-AARDFVAWLLRA;

(SEQ ID NO: 65)
H-Aib-QGTFTSDYSKYLDSKAA-K*-DFVAWLLRA;

(SEQ ID NO: 66)
H-Aib-QGTFTSDYSKYLDSKAAHDFVEWLL-K*-A;

(SEQ ID NO: 67)
H-Aib-QGTFTSDYSKYLDS-K*-AAHDFVEWLLKA;

(SEQ ID NO: 68)
H-Aib-QGTFTSDYSKYLDS-K*-AAHDFVEWLLRA;

(SEQ ID NO: 69)
H-Aib-QGTFTSDYSKYLDSKAA-K*-DFVAWLLSA;

(SEQ ID NO: 70)
H-Aib-QGTFTSDYSKYLDSKAAHDFVAWLL-K*-A;

(SEQ ID NO: 71)
H-Aib-QGTFTSDYSKYLD-K*-KAAHDFVAWLLRA;

(SEQ ID NO: 72)
H-Aib-QGTFTSDYSRYLDS-K*-AAHDFVEWLLSA;
```

-continued

```
                                          (SEQ ID NO: 73)
H-Aib-QGTFTSDYSKYLDSKAAHDFV-K*-WLLSA;

(SEQ ID NO: 74)
H-Aib-QGTFTSDYSLYLDS-K*-AAHDFVEWLLSA;

(SEQ ID NO: 75)
H-Aib-QGTFTSDYSKYLDS-C*-AAHDFVEWLLSA;

(SEQ ID NO: 76)
H-Aib-QGTFTSDYSKYLDSKAA-C*-DFVEWLLRA;

(SEQ ID NO: 77)
H-Aib-QGTFTSDYSKYLD-S*-KAAHDFVEWLLSA;

(SEQ ID NO: 78)
H-Aib-QGTFTSDYSKYLDK( )K*AAE( )DFVEWLLRA;

SEQ ID NO: 79)
H-Aib-QGTFTSDYSKYLDSK*AAHDFVE( )WLLK( )A;

(SEQ ID NO: 80)
H-Aib-QGTFTSDYSKYLDSK*AAK( )DFVE( )WLLRA;

(SEQ ID NO: 81)
H-Aib-QGTFTSDYSKYLDSK( )AAHE( )FVEWLLK*A;
or;

(SEQ ID NO: 82)
H-Aib-QGTFTSDYSKYLDSK( )AAK*E( )FVEWLLRA.
```

Residues marked "( )" participate in an intramolecular bond, such as a lactam ring.

The side chain(s) of one or more of the residues X are conjugated to a lipophilic substituent. For example, one side chain of a residue X may be conjugated to a lipophilic substituent. Alternatively, two, or even more than two, side chains of residues X may be conjugated to a lipophilic substituent.

For example, at least one of X16, X17, X20 and X28 may be conjugated to a lipophilic substituent. In such cases, X30 may be absent. When X30 is present, it is typically conjugated to a lipophilic substituent.

Thus the compound may have just one lipophilic substituent, at position 16, 17, 20, 24, 27, 28 or 30, preferably at position 16, 17 or 20, particularly at position 17.

Alternatively, the compound may have precisely two lipophilic substituents, each at one of positions 16, 17, 20, 24, 27, 28 or 30. Preferably one or both lipophilic substituents are present at one of positions 16, 17 or 20.

Thus, the compound may have lipophilic substituents at positions 16 and 17, 16 and 20, 16 and 24, 16 and 27, 16 and 28 or 16 and 30; at 17 and 20, 17 and 24, 17 and 27, 17 and 28 or 17 and 30; at 20 and 24, 20 and 27, 20 and 28 or 20 and 30; at 24 and 27, 24 and 28 or 24 and 30; at 27 and 28 or 27 and 30; or at 28 and 30.

In yet further embodiments, the compound may have one or more further lipophilic substituents (giving three or more in total) at further positions selected from positions 16, 17, 20, 24, 27, 28 or 30. However it may be desirable that a maximum of two positions are derivatised in this way.

$Z^1$ may comprise a hydrocarbon chain having 10 to 24 C atoms, e.g. 10 to 22 C atoms, e.g. 10 to 20 C atoms. It may have at least 11 C atoms, and/or 18 C atoms or fewer. For example, the hydrocarbon chain may contain 12, 13, 14, 15, 16, 17 or 18 carbon atoms. Thus $Z^1$ may be a dodecanoyl, 2-butyloctanoyl, tetradecanoyl, hexadecanoyl, heptadecanoyl, octadecanoyl or eicosanoyl moiety.

Independently, where present, $Z^2$ may be or comprise one or more amino acid residues. For example, $Z^2$ may be a γ-Glu, Glu, β-Ala or ε-Lys residue, or a 4-aminobutanoyl, 8-aminooctanoyl or 8-amino-3,6-dioxaoctanoyl moiety.

Certain combinations of $Z^1$ and $Z^2$ are dodecanoyl-γ-Glu, hexadecanoly-γ-Glu, hexadecanoyl-Glu, hexadecanoyl-[3-aminopropanoyl], hexadecanoyl-[8-aminooctanoyl], hexadecanoyl-ε-Lys, 2-butyloctanoyl-γ-Glu, octadecanoyl-γ-Glu and hexadecanoyl-[4-aminobutanoyl].

In particular embodiments, Z has the formula:

```
                                          (SEQ ID NO: 83)
HSQGTFTSDYSKYLD-K(Hexadecanoyl-γ-Glu)-KAAHDFVEWL

LRA;

(SEQ ID NO: 84)
HSQGTFTSDYSKYLDSKAAHDFVEWL-K(Hexadecanoyl-γ-Glu)-

RA;

(SEQ ID NO: 85)
HSQGTFTSDYSKYLDSKAA-K(Hexadecanoyl-γ-Glu)-DFVEWLL

RA;

(SEQ ID NO: 86)
HSQGTFTSDYSKYLDSKAAHDFVEWLL-K(Hexadecanoyl-γ-

Glu)-A;

(SEQ ID NO: 87)
H-Aib-QGTFTSDYSKYLDS-K(Hexadecanoyl-γ-Glu)-AAHDFVE

WLLRA;

(SEQ ID NO: 88)
H-Aib-QGTFTSDYSKYLDS-K(Hexadecanoyl-γ-Glu)-AARDFVA

WLLRA;

(SEQ ID NO: 89)
H-Aib-QGTFTSDYSKYLDS-K(Hexadecanoyl-γ-Glu)-AAHDFVE

WLLSA;

(SEQ ID NO: 90)
H-Aib-QGTFTSDYSKYLDSKAAHDFVEWLL-K(Hexadecanoyl-γ-

Glu)-A;

(SEQ ID NO: 91)
H-Aib-QGTFTSDYSKYLDS-K(Hexadecanoyl-γ-Glu)-

AAHDFVE( )WLLK( )A;

(SEQ ID NO: 92)
H-Aib-QGTFTSDYSKYLDS-K(Hexadecanoyl-γ-Glu)-

AAHDFVEWLLKA;

(SEQ ID NO: 93)
HSQGTFTSDYSKYLDS-K(Hexadecanoyl-γ-Glu)-

AAHDFVEWLLRA;

(SEQ ID NO: 94)
H-Aib-QGTFTSDYSKYLDSKAA-K(Hexadecanoyl-γ-Glu)-

DFVAWLLRA;

(SEQ ID NO: 95)
H-Aib-QGTFTSDYSKYLDS-K(Dodecanoyl-γ-Glu)-AAHDFVE

WLLSA;
```

-continued (SEQ ID NO: 96)
H-Aib-QGTFTSDYSKYLDS-K(Hexadecanoyl-[3-aminopropanoyl])-AAHDFVEWLLSA;

(SEQ ID NO: 97)
H-Aib-QGTFTSDYSKYLDS-K(Hexadecanoyl-[8-aminooctanoyl])-AAHDFVEWLLSA;

(SEQ ID NO: 98)
H-Aib-QGTFTSDYSKYLDS-K(Hexadecanoyl-ε-Lys)-AAHDFVEWLLSA;

(SEQ ID NO: 99)
HSQGTFTSDYSKYLDS-K(Hexadecanoyl)-AAHDFVEWLLSA;

(SEQ ID NO: 100)
HSQGTFTSDYSKYLDS-K(Octadecanoyl-γ-Glu)-AAHDFVEWLLSA;

(SEQ ID NO: 101)
HSQGTFTSDYSKYLDS-K([2-Butyloctanoyl]-γ-Glu)-AAHDFVEWLLSA;

(SEQ ID NO: 102)
HSQGTFTSDYSKYLDS-K(Hexadecanoyl-[4-Aminobutanoyl])-AAHDFVEWLLSA;

(SEQ ID NO: 103)
HSQGTFTSDYSKYLDS-K(Octadecanoyl-γ-Glu)-AAHDFVEWLLSA;

(SEQ ID NO: 104)
HSQGTFTSDYSKYLDS-K(Hexadecanoyl-E)-AAHDFVEWLLSA;

(SEQ ID NO: 105)
H-Aib-QGTFTSDYSKYLDS-K(Hexadecanoyl)-AAHDFVEWLLSA;

(SEQ ID NO: 106)
H-Aib-QGTFTSDYSKYLDS-K(Octadecanoyl-γ-Glu)-AAHDFVEWLLSA;

(SEQ ID NO: 107)
H-Aib-QGTFTSDYSKYLDS-K([2-Butyloctanoyl]-γ-Glu)-AAHDFVEWLLSA;

(SEQ ID NO: 108)
H-Aib-QGTFTSDYSKYLDS-K(Hexadecanoyl-[4-Aminobutanoyl])-AAHDFVEWLLSA;

(SEQ ID NO: 109)
H-Aib-QGTFTSDYSKYLDS-K(Octadecanoyl-γ-Glu)-AAHDFVEWLLSA;
or (SEQ ID NO: 110)
H-Aib-QGTFTSDYSKYLDS-K(Hexadecanoyl-E)-AAHDFVEWLLSA.

Residues marked "( )" participate in an intramolecular bond, such as a lactam ring.

In a further embodiment, Z has the formula:

(SEQ ID NO: 111)
H-Aib-QGTFTSDYS-K(Hexadecanoyl-isoGlu)-YLDSKAAHDFVEWLLSA;

(SEQ ID NO: 112)
H-Aib-QGTFTSDYSKYLD-K(Hexadecanoyl-isoGlu)-KAAHDFVEWLLSA;

(SEQ ID NO: 113)
H-Aib-QGTFTSDYSKYLDSKAA-K(Hexadecanoyl-isoGlu)-DFVEWLLSA;

(SEQ ID NO: 114)
H-Aib-QGTFTSDYSKYLDSKAAHDFV-K(Hexadecanoyl-isoGlu)-WLLSA;

(SEQ ID NO: 115)
H-Aib-QGTFTSDYSKYLDS-K(Hexadecanoyl-isoLys)-AARDFVAWLLRA;

(SEQ ID NO: 116)
H-Aib-QGTFTSDYSKYLDS-K(Hexadecanoyl-isoGlu)-AAKDFVEWLLSA;

(SEQ ID NO: 117)
H-Aib-QGTFTSDYSKYLDE-K(Hexadecanoyl-isoGlu)-AAHDFVEWLLSA;

(SEQ ID NO: 118)
H-Aib-QGTFTSDYSKYLDS-K(Hexadecanoyl-isoGlu)-AAHEFVEWLLSA;

(SEQ ID NO: 119)
H-Aib-QGTFTSDYSKYLDS-K(Hexadecanoyl-isoGlu)-AAEDFVEWLLSA;

(SEQ ID NO: 120)
H-Aib-QGTFTSDYSKYLDS-K(Hexadecanoyl-isoGlu)-AAHDFVEWLLEA.

In a further aspect, Z has the formula:

(SEQ ID NO: 121)
H-Aib-QGTFTSDYSKYLDS-K(Hexadecanoyl-isoGlu)-AAHDFVEWLLS;

(SEQ ID NO: 122)
H-Aib-QGTFTSDYSKYLDS-K(Hexadecanoyl-isoGlu)-AAHDFVEWLL;

In still a further aspect, Z has the formula:

(SEQ ID NO: 123)
H-Aib-EGTFTSDYSKYLDS-K(Hexadecanoyl-isoGlu)-AAHDFVEWLLSA;

The invention provides a compound having the formula:

R¹—Z—R² wherein R¹ is H, C$_{1-4}$ alkyl, acetyl, formyl, benzoyl or trifluoroacetyl;
R² is OH or NH$_2$;
and Z is a peptide having the formula I

```
                                           (SEQ ID NO: 4)
His-X2-Gln-Gly-Thr-Phe-Thr-Ser-Asp-Tyr-Ser-X12-

Tyr-Leu-Asp-X16-X17-Ala-Ala-X20-X21-Phe-

Val-X24-Trp-Leu-X27-X28-Ala-X30;
``` wherein
X2 is Aib or Ser;
X12 is selected from Lys, Arg or Leu;
X16 is Arg or X;
X17 is Arg or X;
X20 is Arg, His or X;
X21 is Asp or Glu;
X24 is Ala or X;
X27 is Leu or X;
X28 is Arg or X;
X30 is X or is absent;
and wherein each residue X is independently selected from the group consisting of Glu, Lys, Ser, Cys, Dbu, Dpr and Orn;
wherein the side chain of at least one residue X is conjugated to a lipophilic substituent having the formula:

Z¹, (i)

wherein Z¹ is a lipophilic moiety conjugated directly to the side chain of X; or Z¹Z², (ii)

wherein Z¹ is a lipophilic moiety, Z² is a spacer, and Z¹ is conjugated to the side chain of X via Z²;
with the proviso that Z is not HSQGTFTSDYSKYLDS-K(Hexadecanoyl-γ-Glu)-AAHDFVEWLLRA (SEQ ID NO:5).

X30 may be present or absent. In those embodiments when X30 is present, it may be desirable for it to be Lys.

In certain embodiments, any residue X, and especially any residue X which is conjugated to a lipophilic substituent, is independently selected from Lys, Glu or Cys.

The compound may have the formula:

R¹—Z—R² wherein R¹ is H, C$_{1-4}$ alkyl, acetyl, formyl, benzoyl or trifluoroacetyl;
R² is OH or NH$_2$;
and Z is a peptide having the formula IIa

```
                                           (SEQ ID NO: 6)
His-Aib-Gln-Gly-Thr-Phe-Thr-Ser-Asp-Tyr-Ser-X12-

Tyr-Leu-Asp-X16-X17-Ala-Ala-X20-X21-Phe-

Val-X24-Trp-Leu-Leu-X28-Ala;
``` wherein
X12 is selected from Lys, Arg or Leu;
X16 is Ser or X;
X17 is X;
X20 is His or X;
X21 is Asp or Glu;
X24 is Ala or Glu;
X28 is Ser, Lys or Arg;
and wherein each residue X is independently selected from the group consisting of Glu, Lys, or Cys;
wherein the side chain of at least one residue X is conjugated to a lipophilic substituent having the formula:

Z¹, (i)

wherein Z¹ is a lipophilic moiety conjugated directly to the side chain of X; or Z¹Z², (ii)

wherein Z¹ is a lipophilic moiety, Z² is a spacer, and Z¹ is conjugated to the side chain of X via Z².

Alternatively, the compound may have the formula:

R¹—Z—R² wherein R¹ is H, C$_{1-4}$ alkyl, acetyl, formyl, benzoyl or trifluoroacetyl;
R² is OH or NH$_2$;
and Z is a peptide having the formula IIb

```
                                           (SEQ ID NO: 7)
His-Ser-Gln-Gly-Thr-Phe-Thr-Ser-Asp-Tyr-Ser-X12-

Tyr-Leu-Asp-X16-X17-Ala-Ala-X20-X21-Phe-

Val-X24-Trp-Leu-Leu-X28-Ala;
``` wherein
X12 is selected from Lys, Arg or Leu;
X16 is Ser or X;
X17 is X;
X20 is His or X;
X21 is Asp or Glu;
X24 is Ala or Glu;
X28 is Ser, Lys or Arg;
and wherein each residue X is independently selected from the group consisting of Glu, Lys, or Cys;
wherein the side chain of at least one residue X is conjugated to a lipophilic substituent having the formula:

Z¹, (i)

wherein Z¹ is a lipophilic moiety conjugated directly to the side chain of X; or Z¹Z², (ii)

wherein Z¹ is a lipophilic moiety, Z² is a spacer, and Z¹ is conjugated to the side chain of X via Z²;
with the proviso that Z is not HSQGTFTSDYSKYLDS-K(Hexadecanoyl-γ-Glu))-AAHDFVEWLLRA (SEQ ID NO:5).

The compound may have the formula:

R¹—Z—R² wherein R¹ is H, C$_{1-4}$ alkyl, acetyl, formyl, benzoyl or trifluoroacetyl;
R² is OH or NH$_2$;
and Z is a peptide having the formula IIIa

```
                                           (SEQ ID NO: 8)
His-Aib-Gln-Gly-Thr-Phe-Thr-Ser-Asp-Tyr-Ser-X12-

Tyr-Leu-Asp-Ser-X17-Ala-Ala-X20-X21-Phe-

Val-X24-Trp-Leu-Leu-X28-Ala;
``` wherein
X12 is selected from Lys or Arg;
X17 is X;
X20 is His or X;
X21 is Asp or Glu;
X24 is Ala or Glu;
X28 is Ser, Lys or Arg;
and wherein each residue X is independently selected from Glu, Lys, or Cys;
wherein the side chain of at least one residue X is conjugated to a lipophilic substituent having the formula:

$$Z^1, \qquad (i)$$

wherein $Z^1$ is a lipophilic moiety conjugated directly to the side chain of X; or $$Z^1 Z^2, \qquad (ii)$$

wherein $Z^1$ is a lipophilic moiety, $Z^2$ is a spacer, and $Z^1$ is conjugated to the side chain of X via $Z^2$.

Alternatively the compound may have the formula:

$$R^1\text{—}Z\text{—}R^2$$

wherein $R^1$ is H, $C_{1-4}$ alkyl, acetyl, formyl, benzoyl or trifluoroacetyl;
$R^2$ is OH or $NH_2$;
and Z is a peptide having the formula IIIb

```
                                        (SEQ ID NO: 9)
His-Ser-Gln-Gly-Thr-Phe-Thr-Ser-Asp-Tyr-Ser-X12-

Tyr-Leu-Asp-Ser-X17-Ala-Ala-X20-X21-Phe-Val-X24-

Trp-Leu-Leu-X28-Ala;
``` wherein
X12 is selected from Lys or Arg;
X17 is X;
X20 is His or X;
X21 is Asp or Glu;
X24 is Ala or Glu;
X28 is Ser, Lys or Arg;
and wherein each residue X is independently selected from Glu, Lys, or Cys;
wherein the side chain of at least one residue X is conjugated to a lipophilic substituent having the formula:

$$Z^1, \qquad (i)$$

wherein $Z^1$ is a lipophilic moiety conjugated directly to the side chain of X; or $$Z^1 Z^2, \qquad (ii)$$

wherein $Z^1$ is a lipophilic moiety, $Z^2$ is a spacer, and $Z^1$ is conjugated to the side chain of X via $Z^2$;
with the proviso that Z is not HSQGTFTSDYSKYLDS-K(Hexadecanoyl-γ-Glu))-AAHDFVEWLLRA (SEQ ID NO:5).

The compound may have the formula:

$$R^1\text{—}Z\text{—}R^2$$

wherein $R^1$ is H, $C_{1-4}$ alkyl, acetyl, formyl, benzoyl or trifluoroacetyl;
$R^2$ is OH or $NH_2$;
and Z is a peptide having the formula IVa

```
                                       (SEQ ID NO: 10)
His-Aib-Gln-Gly-Thr-Phe-Thr-Ser-Asp-Tyr-Ser-X12-

Tyr-Leu-Asp-Ser-X17-Ala-Ala-His-X21-Phe-Val-

X24-Trp-Leu-Leu-X28-Ala;
``` wherein
X12 is selected from Lys or Arg;
X17 is X;
X21 is Asp or Glu;
X24 is Ala or Glu;
X28 is Ser, Lys or Arg;
wherein X is selected from the group consisting of Glu, Lys, or Cys;
and wherein the side chain of X is conjugated to a lipophilic substituent having the formula:

$$Z^1, \qquad (i)$$

wherein $Z^1$ is a lipophilic moiety conjugated directly to the side chain of X; or $$Z^1 Z^2, \qquad (ii)$$

wherein $Z^1$ is a lipophilic moiety, $Z^2$ is a spacer, and $Z^1$ is conjugated to the side chain of X via $Z^2$.

Alternatively the compound may have the formula:

$$R^1\text{—}Z\text{—}R^2$$

wherein $R^1$ is H, $C_{1-4}$ alkyl, acetyl, formyl, benzoyl or trifluoroacetyl;
$R^2$ is OH or $NH_2$;
and Z is a peptide having the formula IVb

```
                                       (SEQ ID NO: 11)
His-Ser-Gln-Gly-Thr-Phe-Thr-Ser-Asp-Tyr-Ser-X12-

Tyr-Leu-Asp-Ser-X17-Ala-Ala-His-X21-Phe-Val-X24-

Trp-Leu-Leu-X28-Ala;
``` wherein
X12 is selected from Lys or Arg;
X17 is X;
X21 is Asp or Glu;
X24 is Ala or Glu
X28 is Ser, Lys or Arg;
wherein X is selected from the group consisting of Glu, Lys, or Cys;
and wherein the side chain of X is conjugated to a lipophilic substituent having the formula:

$$Z^1, \qquad (i)$$

wherein $Z^1$ is a lipophilic moiety conjugated directly to the side chain of X; or $$Z^1 Z^2, \qquad (ii)$$

wherein $Z^1$ is a lipophilic moiety, $Z^2$ is a spacer, and $Z^1$ is conjugated to the side chain of X via $Z^2$;
with the proviso that Z is not HSQGTFTSDYSKYLDS-K(Hexadecanoyl-γ-Glu))-AAHDFVEWLLRA (SEQ ID NO:5).

In a further aspect, the present invention provides a composition comprising a compound as defined herein, or a salt or derivative thereof, in admixture with a carrier. In preferred embodiments, the composition is a pharmaceutically acceptable composition and the carrier is a pharmaceutically acceptable carrier. The salt may be a pharmaceutically acceptable acid addition salt of the compound, e.g. an acetate or chloride salt.

The compounds described find use in preventing weight gain or promoting weight loss. By "preventing" is meant inhibiting or reducing weight gain when compared to the absence of treatment, and is not necessarily meant to imply complete cessation of weight gain. The peptides may cause a decrease in food intake and/or increased energy expenditure, resulting in the observed effect on body weight. Independently of their effect on body weight, the compounds of the invention may have a beneficial effect on circulating glucose levels, glucose tolerance, and/or on circulating cholesterol levels, being capable of lowering circulating LDL levels and increasing HDL/LDL ratio. Thus the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for the treatment of pre-diabetes, insulin resistance, glucose intolerance, type 2 diabetes, type I diabetes, hypertension or atherogenic dyslipidaemia (or a combination of two or more of these metabolic risk factors), atherosclerosis, arteriosclerosis, coronary heart disease, peripheral artery disease, stroke and microvascular disease. Their effects in these conditions may be as a result of or associated with their effect on body weight, or may be independent thereof.

Thus the invention provides use of a compound of the invention in the treatment of a condition as described above, in an individual in need thereof.

The invention also provides a compound of the invention for use in a method of medical treatment, particularly for use in a method of treatment of a condition as described above.

The invention also provides the use of a compound of the invention in the preparation of a medicament for the treatment of a condition as described above.

The compound of the invention may be administered as part of a combination therapy with an agent for treatment of diabetes, obesity, dyslipidaemia or hypertension.

In such cases, the two active agents may be given together or separately, and as part of the same pharmaceutical formulation or as separate formulations.

Thus the compound of the invention (or the salt thereof) can be used in combination with an anti-diabetic agent including but not limited to metformin, a sulfonylurea, a glinide, a DPP-IV inhibitor, a glitazone, or insulin. In a preferred embodiment the compound or salt thereof is used in combination with insulin, DPP-IV inhibitor, sulfonylurea or metformin, particularly sulfonylurea or metformin, for achieving adequate glycemic control. In an even more preferred embodiment the compound or salt thereof is used in combination with a metformin, a sulfonylurea, insulin or an insulin analogue for achieving adequate glycemic control. Examples of insulin analogues include but are not limited to Lantus, Novorapid, Humalog, Novomix, Actraphane HM, Levemir and Apidra.

The compound or salt thereof can further be used in combination with an anti-obesity agent including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

The compound or salt thereof can further be used in combination with an anti-hypertension agent including but not limited to an angiotensin-converting enzyme inhibitor, angiotensin II receptor blocker, diuretic, beta-blocker, or calcium channel blocker.

The compound or salt thereof can be used in combination with an anti-dyslipidemia agent including but not limited to a statin, a fibrate, a niacin or a cholesterol absorbtion inhibitor.

DETAILED DESCRIPTION OF THE INVENTION

Figure 1:
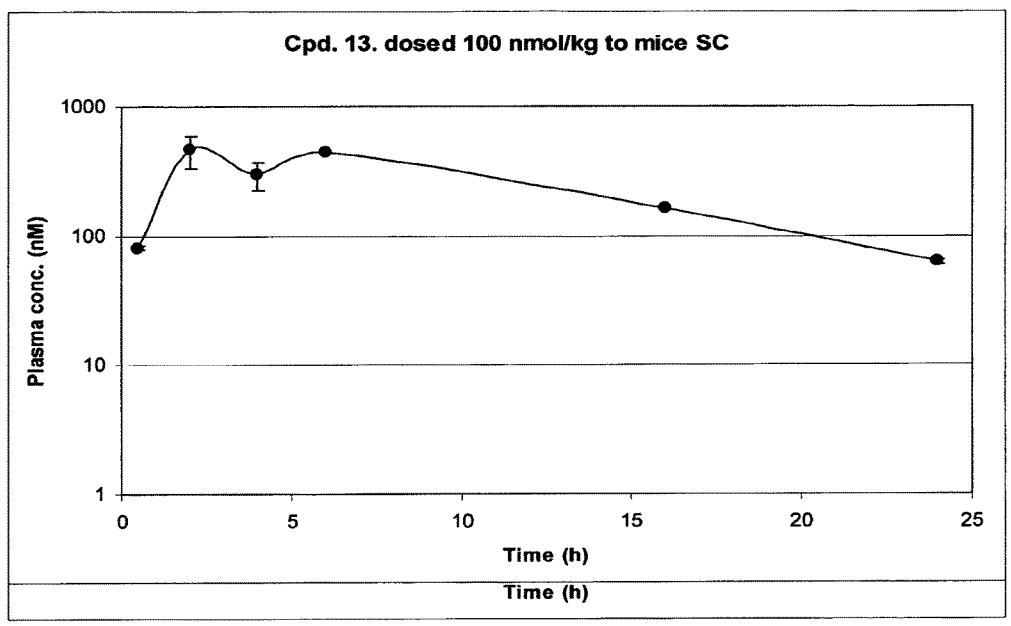
FIG. 1. Pharmacokinetic profile of compound 13 after subcutaneous (s.c.) administration to mice at a dose of 100 nmol/kg.
Figure 2:
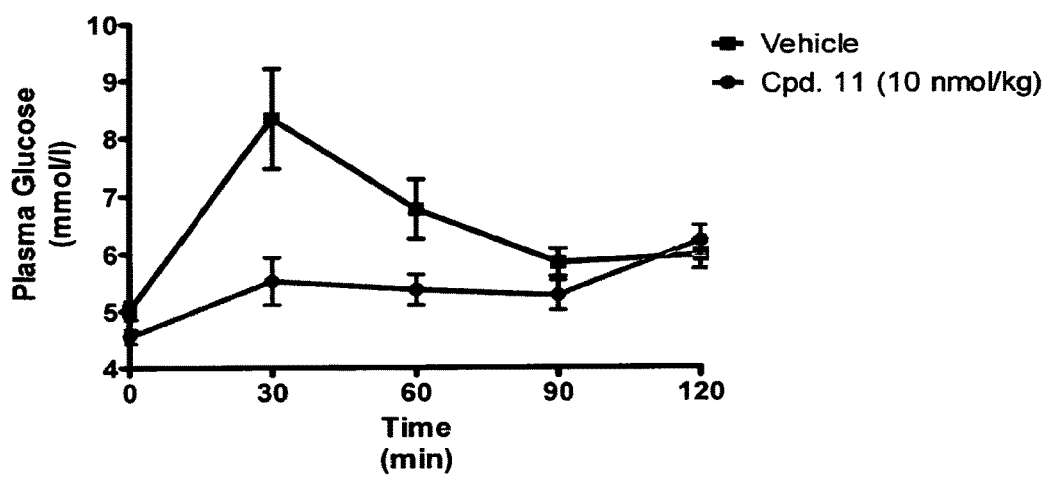
FIG. 2. Effect of 21 days s.c. administration of compound 11 (10 nmol/kg) on oral glucose tolerance in long term high fat fed C57BL/6J mice. Data are shown as mean±SEM.

Throughout this specification, the conventional one letter and three letter codes for naturally occurring amino acids are used, as well as generally accepted three letter codes for other amino acids, including Aib (α-aminoisobutyric acid), Orn (ornithine), Dbu (2,4 diaminobutyric acid) and Dpr (2,3-diaminopropanoic acid).

The term "native glucagon" refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO:1).

The peptide sequence of the compound of the invention differs from that of native glucagon at least at positions 18, 20, 24, 27, 28 and 29. In addition, it may differ from that of native glucagon at one or more of positions 12, 16 and 17.

Native glucagon has Arg at position 18. The compound of the invention has the small hydrophobic residue Ala at position 18 which is believed to increase potency at both glucagon and GLP-1 receptors but particularly the GLP-1 receptor.

The residues at positions 27, 28 and 29 of native glucagon appear to provide significant selectivity for the glucagon receptor. The substitutions at these positions with respect to the native glucagon sequence, particularly the Ala at position 29, may increase potency at and/or selectivity for the GLP-1 receptor, potentially without significant reduction of potency at the glucagon receptor. Further examples which may be included in the compounds of the invention include Leu at position 27 and Arg at position 28. Furthermore, Arg at position 28 may be particularly preferred when there is a Glu at position 24 with which it can form an intramolecular bridge, since this may increase its effect on potency at the GLP-1 receptor.

Substitution of the naturally-occurring Met residue at position 27 (e.g. with Leu, Lys or Glu) also reduces the potential for oxidation, thereby increasing the chemical stability of the compounds.

Substitution of the naturally-occurring Asn residue at position 28 (e.g. by Arg or Ser) also reduces the potential for deamidation in acidic solution, thereby increasing the chemical stability of the compounds.

Potency and/or selectivity at the GLP-1 receptor, potentially without significant loss of potency at the glucagon receptor, may also be increased by introducing residues that are likely to stabilise an alpha-helical structure in the C-terminal portion of the peptide. It may be desirable, but is not believed essential, for this helical portion of the molecule to have an amphipathic character. Introduction of residues such as Leu at position 12 and/or Ala at position 24 may assist. Additionally or alternatively charged residues may be introduced at one or more of positions 16, 20, 24, and 28. Thus the residues of positions 24 and 28 may all be charged, the residues at positions 20, 24, and 28 may all be charged, or the residues at positions 16, 20, 24, and 28 may all be charged. For example, the residue at position 20 may be His or Arg, particularly His. The residue at position 24 may be Glu, Lys or Arg, particularly Glu. The residue at position 28 may be Arg. Introduction of an intramolecular bridge in this portion of the molecule, as discussed above, may also contribute to stabilising the helical character, e.g. between positions 24 and 28.

Substitution of one or both of the naturally-occurring Gln residues at positions 20 and 24 also reduces the potential for deamidation in acidic solution, so increasing the chemical stability of the compounds.

A substitution relative to the native glucagon sequence at position 12 (i.e. of Arg or Leu) may increase potency at both receptors and/or selectivity at the GLP-1 receptor.

C-terminal truncation of the peptide does not reduce potency of both receptors and/or selectivity of the GLP-1 receptor. In particular, truncation of position 29 or truncation of both position 28 and 29 does not reduce the receptor potency to any of the two receptors.

The side chain of one or more of the residues designated X (i.e. positions 16, 17, 20, 24, 27 and 28, and/or 30 if present) is conjugated to a lipophilic substituent. It will be appreciated that conjugation of the lipophilic substituent to a particular side chain may affect (e.g. reduce) certain of the benefits which the unconjugated side chain may provide at that position. The inventors have found that compounds of the invention provide a balance between the benefits of acylation and the benefits of particular substitutions relative to the native glucagon sequence.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Other groups have attempted to prolong the half life of GluGLP-1 dual agonist compounds by derivatisation with PEG (WO2008/101017). However such derivatisation appears to be most effective when applied to the C-terminus of the molecule rather than in the central core of the peptide backbone, and potency of these compounds is still decreased compared to the corresponding unmodified peptide.

By contrast, the compounds of the present invention retain high potency at both the glucagon and GLP-1 receptors while having significantly protracted pharmacokinetic profiles compared to the corresponding unmodified peptides.

Native glucagon has Ser at position 16. Substitution with Ala, Gly or Thr has been shown to reduce adenylate cyclase activation at the glucagon receptor significantly (Unson et al. Proc. Natl. Acad. Sci. 1994, 91, 454-458). Hence, derivatisation with a lipophilic substituent at position 16 would not have been expected to yield compounds retaining potency at the glucagon receptor, as is surprisingly shown by the compounds described in this specification. In WO2008/101017 a negatively charged residue was found to be desirable at position 16 to minimise loss of potency.

The presence of basic amino acids at positions 17 and 18 is generally believed to be necessary for full glucagon receptor activation (Unson et al. J. Biol. Chem. 1998, 273, 10308-10312). The present inventors have found that, when position 18 is alanine, substitution with a hydrophobic amino acid in position 17 can still yield a highly potent compound. Even compounds in which the amino acid in position 17 is derivatised with a lipophilic substituent retain almost full potency at both glucagon and GLP-1 receptors, as well as displaying a significantly protracted pharmacokinetic profile. This is so even when a lysine at position 17 is derivatised, converting the basic amine side chain into a neutral amide group.

The present inventors have also found that compounds with acylation at position 20 are still highly active dual agonists, despite indications from other studies that substitution in position 20 should be a basic amino acid having a side chain of 4-6 atoms in length to enhance GLP-1 receptor activity compared to glucagon (WO2008/101017). The compounds described herein retain both GLP-1 and glucagon receptor activity when position 20 is substituted with lysine and acylated.

Peptide Synthesis

The peptide component of the compounds of the invention may be manufactured by standard synthetic methods, recombinant expression systems, or any other suitable method. Thus the peptides may be synthesized in a number of ways including for example, a method which comprises:
(a) synthesizing the peptide by means of solid phase or liquid phase methodology either stepwise or by fragment assembling and isolation and purification of the final peptide product;
(b) expressing a nucleic acid construct that encodes the peptide in a host cell and recovering the expression product from the host cell culture; or
(c) effecting cell-free in vitro expression of a nucleic acid construct that encodes the peptide and recovering the expression product;
or any combination of methods of (a), (b), and (c) to obtain fragments of the peptide, subsequently ligating the fragments to obtain the peptide, and recovering the peptide.

It may be preferred to synthesize the analogues of the invention by means of solid phase or liquid phase peptide synthesis. In this context, reference is given to WO 98/11125 and, amongst many others, Fields, G B et al., 2002, "Principles and practice of solid-phase peptide synthesis". In: Synthetic Peptides (2nd Edition) and the examples herein.

Lipophilic Substituent

One or more of the amino acid side chains in the compound of the invention is conjugated to a lipophilic substituent $Z^1$. Without wishing to be bound by theory, it is thought that the lipophilic substituent binds albumin in the blood stream, thus shielding the compounds of the invention from enzymatic degradation which can enhance the half-life of the compounds. It may also modulate the potency of the compound, e.g. with respect to the glucagon receptor and/or the GLP-1 receptor.

In certain embodiments, only one amino acid side chain is conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different.

The lipophilic substituent $Z^1$ may be covalently bonded to an atom in the amino acid side chain, or alternatively may be conjugated to the amino acid side chain by a spacer $Z^2$.

The term "conjugated" is used here to describe the physical attachment of one identifiable chemical moiety to another, and the structural relationship between such moieties. It should not be taken to imply any particular method of synthesis.

The spacer $Z^2$, when present, is used to provide a spacing between the compound and the lipophilic moiety.

The lipophilic substituent may be attached to the amino acid side chain or to the spacer via an ester, a sulphonyl ester, a thioester, an amide or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic substituent may include a hydrocarbon chain having 10 to 24 C atoms, e.g. 10 to 22 C atoms, e.g. 10 to 20 C atoms. Preferably it has at least 11 C atoms, and preferably it has 18 C atoms or fewer. For example, the hydrocarbon chain may contain 12, 13, 14, 15, 16, 17 or 18 carbon atoms. The hydrocarbon chain may be linear or branched and may be saturated or unsaturated. From the discussion above it will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with acyl, and accordingly the hydrocarbon chain may be part of an alkanoyl group, for example a dodecanoyl, 2-butyloctanoyl, tetradecanoyl, hexadecanoyl, heptadecanoyl, octadecanoyl or eicosanoyl group.

As mentioned above, the lipophilic substituent $Z^1$ may be conjugated to the amino acid side chain by a spacer $Z^2$. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may consist of a linear $C_{1-10}$ hydrocarbon chain or more preferably a linear $C_{1-5}$ hydrocarbon chain. Furthermore the spacer can be substituted with one or more substituents selected from $C_{1-6}$ alkyl, $C_{1-6}$ alkyl amine, $C_{1-6}$ alkyl hydroxy and $C_{1-6}$ alkyl carboxy.

The spacer may be, for example, a residue of any naturally occurring or unnatural amino acid. For example, the spacer may be a residue of Gly, Pro, Ala, Val, Leu, Ile, Met, Cys, Phe, Tyr, Trp, His, Lys, Arg, Gln, Asn, α-Glu, γ-Glu, ε-Lys, Asp, Ser, Thr, Gaba, Aib, β-Ala (i.e. 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8-amino-3,6-dioxaoctanoyl. In certain embodiments, the spacer is a residue of Glu, γ-Glu, ε-Lys, β-Ala (i.e. 3-aminopropanoyl), 4-aminobutanoyl, 8-aminooctanoyl or 8-amino-3,6-dioxaoctanoyl. In the present invention, γ-Glu and isoGlu are used interchangeably.

The amino acid side chain to which the lipophilic substituent is conjugated is a side chain of a Glu, Lys, Ser, Cys, Dbu, Dpr or Orn residue. For example it may be a side chain of a Lys, Glu or Cys residue. Where two or more side chains carry a lipophilic substituent, they may be independently selected from these residues. Thus the amino acid side chain includes an carboxy, hydroxyl, thiol, amide or amine group, for forming an ester, a sulphonyl ester, a thioester, an amide or a sulphonamide with the spacer or lipophilic substituent.

An example of a lipophilic substituent comprising a lipophilic moiety $Z^1$ and spacer $Z^2$ is shown in the formula below:

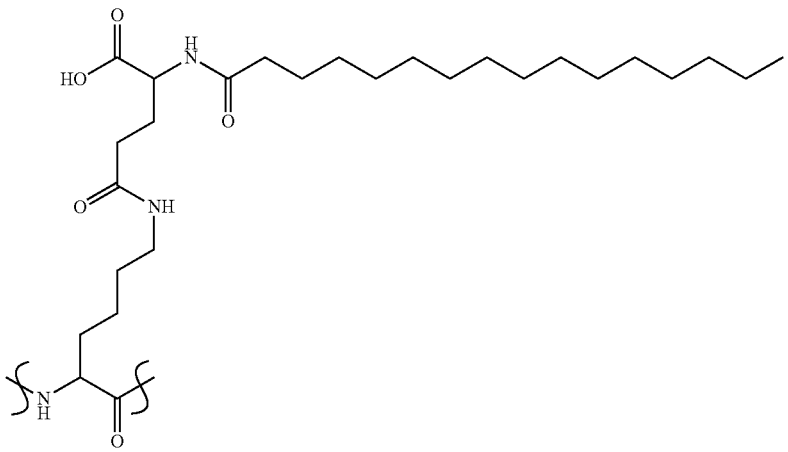 [SMILES: CCCCCCCCCCCCCCCC(=O)NC(CCC(=O)NCCCCC(NC)C(C)=O)C(=O)O]

Here, the side chain of a Lys residue from the peptide of formula I is covalently attached to an γ-Glu spacer ($Z^2$) via an amide linkage. A hexadecanoyl group ($Z^1$) is covalently attached to the γ-Glu spacer via an amide linkage. This combination of lipophilic moiety and spacer, conjugated to a Lys residue, may be referred to by the short-hand notation K(Hexadecanoyl-γ-Glu), e.g. when shown in formulae of specific compounds. γ-Glu can also be referred to as isoGlu, and a hexadecanoyl group as a palmitoyl group. Thus it will be apparent that the notation (Hexadecanoyl-γ-Glu) is equivalent to the notations (isoGlu(Palm)) or (isoGlu(Palmitoyl)) as used for example in PCT/GB2008/004121.

The skilled person will be well aware of suitable techniques for preparing the compounds of the invention. For examples of suitable chemistry, see WO98/08871, WO00/55184, WO00/55119, Madsen et al (J. Med. Chem. 2007, 50, 6126-32), and Knudsen et al. 2000 (J. Med Chem. 43, 1664-1669).

PEGylated and/or acylation have a short half-life (T½), which gives rise to burst increases of GluGLP-1 agonist concentrations. The glucagon receptor is thus being subjected to burst exposure to the glucagon agonism once (or twice) daily throughout the treatment period.

Without being bound to any theory repeated burst exposure of GluR to glucagon agonism seems to bring havoc to the lipid and free fatty acid trafficking between the liver and adipose tissue with the result that fat accumulates in the liver.

Constant exposure of GluR to glucagon agonism blocks accumulation of fat in the liver It has thus been found, that repeated treatment with glucagon or short acting dual GluGLP-1 agonists give rise to enlarged liver due to fat and glycogen accumulation (Chan et al., 1984. Exp. Mol. Path. 40, 320-327).

Repeated treatment with long-acting acylated dual GluGLP-1 agonists do not give rise to change in liver size (enlarged or shrunken) in normal weight subjects, but normalize liver lipid content (Day et al., 2009; Nat. Chem. Biol. 5, 749-57).

Efficacy

Binding of the relevant compounds to GLP-1 or glucagon (Glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may make use the human glucagon receptor (Glucagon-R) having primary accession number GI: 4503947 (NP_000151.1) and/or the human glucagon-like peptide 1 receptor (GLP-1R) having primary accession number GI:166795283 (NP_002053.3). (Where sequences of precursor proteins are referred to, it should of course be understood that assays may make use of the mature protein, lacking the signal sequence).

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$ [GLP-1R] lower than the $EC_{50}$ [GLP-1R] of native glucagon in a particular assay may be considered to have higher potency at the GLP-1R than glucagon.

The compounds described in this specification are typically Glu-GLP-1 dual agonists, i.e. they are capable of stimulating cAMP formation at both the glucagon receptor and the GLP-1R. The stimulation of each receptor can be measured in independent assays and afterwards compared to each other.

By comparing the $EC_{50}$ value for the glucagon receptor ($EC_{50}$ [Glucagon-R]) with the $EC_{50}$ value for the GLP-1 receptor ($EC_{50}$ [GLP-1R]) for a given compound the relative glucagon selectivity (%) of that compound can be found:

Relative Glucagon-R selectivity[Compound]=(1/$EC_{50}$ [Glucagon-R])×100%/(1/$EC_{50}$[Glucagon-R]+1/ $EC_{50}$[GLP-1R])

The relative GLP-1R selectivity can likewise be found:

Relative GLP-1R selectivity[Compound]=(1/$EC_{50}$ [GLP-1R])×100%/(1/$EC_{50}$[Glucagon-R]+1/$EC_{50}$ [GLP-1R])

A compound's relative selectivity allows its effect on the GLP-1 or glucagon receptor to be compared directly to its effect on the other receptor. For example, the higher a compound's relative GLP-1 selectivity is, the more effective that compound is on the GLP-1 receptor as compared to the glucagon receptor.

Using the assays described below, we have found the relative GLP-1 selectivity for human glucagon to be approximately 5%.

The compounds of the invention have a higher relative GLP-1R selectivity than human glucagon. Thus, for a particular level of glucagon-R agonist activity, the compound will display a higher level of GLP-1R agonist activity (i.e. greater potency at the GLP-1 receptor) than glucagon. It will be understood that the absolute potency of a particular compound at the glucagon and GLP-1 receptors may be higher, lower or approximately equal to that of native human glucagon, as long as the appropriate relative GLP-1R selectivity is achieved.

Nevertheless, the compounds of this invention may have a lower $EC_{50}$ [GLP-1R] than human glucagon. The compounds may have a lower $EC_{50}$ [GLP-1R] than glucagon while maintaining an $EC_{50}$ [Glucagon-R] that is less than 10-fold higher than that of human glucagon, less than 5-fold higher than that of human glucagon, or less than 2-fold higher than that of human glucagon.

It may be desirable that $EC_{50}$ of any given compound for both the Glucagon-R and GLP-1R should be less than 1 nM.

The compounds of the invention may have an $EC_{50}$ [Glucagon-R] that is less than two-fold that of human glucagon. The compounds may have an $EC_{50}$ [Glucagon-R] that is less than two-fold that of human glucagon and have an $EC_{50}$ [GLP-1R] that is less than half that of human glucagon, less than a fifth of that of human glucagon, or less than a tenth of that of human glucagon.

The relative GLP-1 selectivity of the compounds may be greater than 5% and less than 95%. For example, the compounds may have a relative selectivity of 5-20%, 10-30%, 20-50%, 30-70%, or 50-80%, or of 30-50%, 40-60%, 50-70% or 75-95%.

Therapeutic Uses

The compounds of the invention may provide an attractive treatment option for metabolic diseases including obesity and diabetes mellitus (diabetes).

Diabetes comprises a group of metabolic diseases characterized by hyperglycemia resulting from defects in insulin secretion, insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with long-term damage, dysfunction, and failure of various organs, notably the eyes, kidneys, nerves, heart and blood vessels. Diabetes is classified into type 1 diabetes, type 2 diabetes and gestational diabetes on the basis on pathogenetic characteristics.

Type 1 diabetes accounts for 5-10% of all diabetes cases and is caused by auto-immune destruction of insulin-secreting pancreatic β-cells.

Type 2 diabetes accounts for 90-95% of diabetes cases and is a result of a complex set of metabolic disorders. Type 2 diabetes is the consequence of endogenous insulin production becoming insufficient to maintain plasma glucose levels below the diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor-1 in the blood), and proinflammatory state (e.g., elevated C-reactive protein in the blood).

Conversely, obesity confers an increased risk of developing pre-diabetes, type 2 diabetes as well as e.g. certain types of cancer, obstructive sleep apnea and gall-bladder disease.

Dyslipidaemia is associated with increased risk of cardiovascular disease. High Density Lipoprotein (HDL) is of clinical importance since an inverse correlation exists between plasma HDL concentrations and risk of atherosclerotic disease. The majority of cholesterol stored in atherosclerotic plaques originates from LDL and hence elevated concentrations Low Density Lipoproteins (LDL) is closely associated with atherosclerosis. The HDL/LDL ratio is a clinical risk indictor for atherosclerosis and coronary atherosclerosis in particular.

Without wishing to be bound by any particular theory, it is believed that the compounds of the invention act as GluGLP-1 dual agonists. The dual agonist may combine the effect of glucagon e.g. on fat metabolism with the effect of GLP-1 e.g. on blood glucose levels and food intake. They might therefore act to accelerate elimination of excessive adipose tissue, induce sustainable weight loss, and improve glycaemic control. Dual GluGLP-1 agonists might also act to reduce cardiovascular risk factors such as high cholesterol and LDL-cholesterol.

The compounds of the present invention can therefore be used as pharmaceutical agents for preventing weight gain, promoting weight loss, reducing excess body weight or treating obesity (e.g. by control of appetite, feeding, food intake, calorie intake, and/or energy expenditure), including morbid obesity, as well as associated diseases and health conditions including but not limited to obesity linked inflammation, obesity linked gallbladder disease and obesity induced sleep apnea. The compounds of the invention may also be used for treatment of insulin resistance, glucose intolerance, pre-diabetes, increased fasting glucose, type 2 diabetes, hypertension, dyslipidemia (or a combination of these metabolic risk factors), atheroscleroris, arteriosclerosis, coronary heart disease, peripheral artery disease and stroke.

These are all conditions which can be associated with obesity. However, the effects of the compounds of the invention on these conditions may be mediated in whole or in part via an effect on body weight, or may be independent thereof.

Pharmaceutical Compositions

The compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. By treatment is meant inhibiting or reducing an increase in pathology or symptoms (e.g. weight gain, hyperglycaemia) when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy.

Subcutaneous or transdermal modes of administration may be particularly suitable for the compounds described herein.

Combination Therapy

The compound of the invention may be administered as part of a combination therapy with an agent for treatment of diabetes, obesity, dyslipidaemia or hypertension.

In such cases, the two active agents may be given together or separately, and as part of the same pharmaceutical formulation or as separate formulations.

Thus the compound of the invention (or the salt thereof) can be used in combination with an anti-diabetic agent including but not limited to metformin, a sulfonylurea, a glinide, a DPP-IV inhibitor, a glitazone, or insulin. In a preferred embodiment the compound or salt thereof is used in combination with insulin, DPP-IV inhibitor, sulfonylurea or metformin, particularly sulfonylurea or metformin, for achieving adequate glycemic control. In an even more preferred embodiment the compound or salt thereof is used in combination with insulin or an insulin analogue for achieving adequate glycemic control. Examples of insulin analogues include but are not limited to Lantus, Novorapid, Humalog, Novomix, Actraphane HM, Levemir and Apidra.

The compound or salt thereof can further be used in combination with an anti-obesity agent including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

The compound or salt thereof can be used in combination with an anti-hypertension agent including but not limited to an angiotensin-converting enzyme inhibitor, angiotensin II receptor blocker, diuretics, beta-blocker, or calcium channel blocker.

The compound or salt thereof can be used in combination with an anti-dyslipidaemia agent including but not limited to a statin, a fibrate, a niacin and/or a cholesterol absorbtion inhibitor.

Methods

General Synthesis of Acylated Glucagon Analogues

Solid phase peptide synthesis was performed on a CEM Liberty Peptide Synthesizer using standard Fmoc chemistry. TentaGel S Ram resin (1 g; 0.25 mmol/g) was swelled in NMP (10 ml) prior to use and transferred between tube and reaction vessel using DCM and NMP.

Coupling:

An Fmoc-amino acid in NMP/DMF/DCM (1:1:1; 0.2 M; 5 ml) was added to the resin in a CEM Discover microwave unit together with HATU/NMP (0.5 M; 2 ml) and DIPEA/NMP (2.0 M; 1 ml). The coupling mixture was heated to 75° C. for 5 min while nitrogen was bubbled through the mixture. The resin was then washed with NMP (4×10 ml).

Deprotection:

Piperidine/NMP (20%; 10 ml) was added to the resin for initial deprotection and the mixture was heated by microwaves (30 sec.; 40° C.). The reaction vessel was drained and a second portion of piperidine/NMP (20%; 10 ml) was added and heated (75° C.; 3 min.) again. The resin was then washed with NMP (6×10 ml).

Side Chain Acylation:

Fmoc-Lys(ivDde)-OH or alternatively another amino acid with an orthogonal side chain protective group was introduced at the position of the acylation. The N-terminal of the peptide backbone was then Boc-protected using Boc$_2$O or alternatively by using a Boc-protected amino acid in the last coupling. While the peptide was still attached to the resin, the orthogonal side chain protective group was selectively cleaved using freshly prepared hydrazine hydrate (2-4%) in NMP for 2×15 min. The unprotected lysine side chain was first coupled with Fmoc-Glu-OtBu or another spacer amino acid, which was deprotected with piperidine and acylated with a lipophilic moiety using the peptide coupling methodology as described above.

Abbreviations employed are as follows:
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane Cleavage:

The resin was washed with EtOH (3×10 ml) and Et$_2$O (3×10 ml) and dried to constant weight at room temperature (r.t.). The crude peptide was cleaved from the resin by treatment with TFA/TIS/water (95/2.5/2.5; 40 ml, 2 h; r.t.).

Most of the TFA was removed at reduced pressure and the crude peptide was precipitated and washed three times with diethylether and dried to constant weight at room temperature.

HPLC Purification of the Crude Peptide:

The crude peptide was purified to greater than 90% by preparative reverse phase HPLC using a PerSeptive Biosystems VISION Workstation equipped with a C-18 column (5 cm; 10 μm) and a fraction collortor and run at 35 ml/min with a gradient of buffer A (0.1% TFA, aq.) and buffer B (0.1% TFA, 90% MeCN, aq.). Fractions were analysed by analytical HPLC and MS and relevant fractions were pooled and lyophilised. The final product was characterised by HPLC and MS.

Generation of Cell Lines Expressing Human Glucagon- and GLP-1 Receptors

The cDNA encoding either the human glucagon receptor (Glucagon-R) (primary accession number P47871) or the human glucagon-like peptide 1 receptor (GLP-1R) (primary accession number P43220) were cloned from the cDNA clones BC104854 (MGC:132514/IMAGE:8143857) or BC112126 (MGC:138331/IMAGE:8327594), respectively. The DNA encoding the Glucagon-R or the GLP-1R was amplified by PCR using primers encoding terminal restriction sites for subcloning. The 5'-end primers additionally encoded a near Kozak consensus sequence to ensure efficient translation. The fidelity of the DNA encoding the Glucagon-R and the GLP-1R was confirmed by DNA sequencing. The PCR products encoding the Glucagon-R or the GLP-1R were subcloned into a mammalian expression vector containing a neomycin (G418) resistance marker.

The mammalian expression vectors encoding the Glucagon-R or the GLP-1R were transfected into HEK293 cells by a standard calcium phosphate transfection method. 48 hr after transfection cells were seeded for limited dilution cloning and selected with 1 mg/ml G418 in the culture medium. Three weeks later 12 surviving colonies of Glucagon-R and GLP-1R expressing cells were picked, propagated and tested in the Glucagon-R and GLP-1R efficacy assays as described below. One Glucagon-R expressing clone and one GLP-1R expressing clone were chosen for compound profiling.

Glucagon Receptor and GLP-1 Receptor Efficacy Assays

HEK293 cells expressing the human Glucagon-R, or human GLP-1R were seeded at 40,000 cells per well in 96-well microtiter plates coated with 0.01% poly-L-lysine and grown for 1 day in culture in 100 μl growth medium. On the day of analysis, growth medium was removed and the cells washed once with 200 μl Tyrode buffer. Cells were incubated in 100 μl Tyrode buffer containing increasing concentrations of test peptides, 100 μM IBMX, and 6 mM glucose for 15 min at 37° C. The reaction was stopped by addition of 25 μl 0.5 M HCl and incubated on ice for 60 min. The cAMP content was estimated using the FlashPlate® cAMP kit from Perkin-Elmer. $EC_{50}$ and relative efficacies compared to reference compounds (glucagon and GLP-1) were estimated by computer aided curve fitting.

Bioanalytical Screening-Method for Quantification of Peptide Glu-GLP1 Agonists in Mouse Plasma after Subcutaneous Administration Mice were dosed 100 nmol/kg subcutaneously (s.c.). The mice were sacrificed and the blood collected at the following time points; 0.5, 2, 4, 6, 16 and 24 h. Plasma samples were analyzed using protein precipitation, followed by solid phase extraction (SPE) and liquid chromatography mass spectrometry (LC-MS).

Oral Glucose Tolerance Test (OGTT), Blood Lipids and Body Weight in High Fat Fed C57Bl/6J Normal Mice and HbA1c in Db/Db Mice Male mice (Long term high fat fed C57Bl/6J, short term high fat fed C57Bl/6J and db/db) were acclimatized with free access to food and water. They were housed in groups of 5-6 in a light-, temperature-, and humidity-controlled room (12-hour light:12-hour dark cycle, lights On/Off at 2000/0800 hour; 24° C.; 50% relative humidity).

The animals were injected s.c. with 100 µl vehicle (once a day) for a period of three days to acclimatize the animals to handling and injections. Blood samples were taken from the eye or from the tip of the tail. The animals were randomized before treatment.

Mice were treated twice daily s.c. with GluGLP-1 agonist or vehicle (injection volume=2.5 ml/kg). Throughout the study, body weights were recorded daily and used to administer the body weight-corrected doses of peptide. Peptide solutions were prepared fresh immediately before dosing.

Oral glucose tolerance tests (OGTT) were performed after subjecting the animals to a short fast. To prevent confounding food intake, the animals were kept fasted during the OGTTs. After peptide dosing an initial blood sample was taken. Thereafter an oral dose of glucose (1 g/kg), dissolved in phosphate buffer (pH=7.4) was given (5 ml/kg), and the animals were returned to their home cages (t=0). The whole blood glucose (BG) was measured at t=15 min, t=30 min, t=60 min, t=90 min and t=120 min.

The BG concentration was analyzed by the immobilized glucose oxidase method using a drop of blood (<5 µl; Elite Autoanalyser, Bayer, Denmark) following the manufacturer's instructions.

HbA1c Determination

It is possible to assess the long term effect of a compound on a subject's glucose level by determining the level of haemoglobin A1C (HbA1c). HbA1c is a glycated form of haemoglobin whose level in a cell reflects the average level of glucose to which the cell has been exposed during its lifetime. In mice, HbA1c is a relevant biomarker for the average blood glucose level during the preceding 4 weeks, because conversion to HbA1c is limited by the erythrocyte's life span of approximately 47 days (Abbrecht & Littell, 1972; J. Appl. Physiol. 32, 443-445).

The HbA1c determination is based on Turbidimetric INhibition ImmunoAssay (TINIA) in which HbA1c in the sample reacts with anti-HbA1c to form soluble antigen-antibody complexes. Additions of polyhaptens react with excess anti-HbA1c antibodies to form an insoluble antibody-polyhapten complex, which can be measured turbidimetrically. Liberated hemoglobin in the hemolyzed sample is converted to a derivative having a characteristic absorption spectrum, which is measured bichromatically during the preincubation phases. The final result is expressed as percent HbA1c of total hemoglobin (Cobas® Application note A1C-2).

Cholesterol Level Determination

The assay is an enzymatic colorimetric method. In the presence of magnesium ions, dextran sulfate selectively forms water-soluble complexes with LDL, VLDLA and chylomicrons, which are resistant to PEG-modified enzymes. The HDL cholesterol is determined enzymatically by cholesterol esterase and cholesterol oxidase coupled with PEG to the amino groups. Cholesterol esters are broken down quantitatively to free cholesterol and fatty acids. HDL cholesterol is enzymatically oxidized to choles-4-en-3-one and $H_2O_2$, and the formed $H_2O_2$ is measured colorimetrically (Cobas®; Application note HDLC3).

The direct determination of LDL takes advantage of the selective micellary solubilization of LDL by a nonionic detergent and the interaction of a sugar compound and lipoproteins (VLDL and chylomicrons). The combination of a sugar compound with detergent enables the selective determination of LDL in plasma. The test principle is the same as that of cholesterol and HDL, but due to the sugar and detergent only LDL-cholesterol esters are broken down to free cholesterol and fatty acids. Free cholesterol is then oxidized and the formed $H_2O_2$ is measured colorimetrically (Application note LDL_C, Cobas®).

Body Weight Gain in High Fat Fed C57BL/6J Mice.

C57Bl/6J male mice, 6 weeks old, were acclimatized in their new environment for 4 weeks with free access to high fat diet (HFD) (D12492, Research Diet Inc., New Brunswick, USA) and water. The animals were injected s.c. with 100 µl vehicle for a period of three days to acclimatize the animals to handling and injections, prior to initiation of peptide treatment. The mice were treated twice daily s.c. with exendin-4, Compound 3, Compound 6, Compound 7, Compound 8, Compound 11 and Compound 12 or vehicle. Throughout the study, body weights were recorded daily and used to administer the body weight-corrected doses of peptide. All animals were sacrificed on the same day by cervical dislocation.

Oral Glucose Tolerance 2, 4, 6, 8, 10 and 12 h after Dosing in High Fat Fed C57BL/6J Mice C57Bl/6J male mice, 6 weeks old, were acclimatized to their new environment with free access to a high fat diet (D12492, Research Diet Inc., New Brunswick, USA) and water. The animals were injected s.c. with vehicle for a period of three days to acclimatize the animals to handling and injections. Blood samples were taken from the tip of the tail and blood glucose measured. The blood glucose (mM) concentration was analyzed by the immobilized glucose oxidase method using a drop of blood (<5 µl; Contour Autoanalyser, Bayer, Denmark) following the manufacturer's manual. After 4 weeks on the high fat diet the animals were weighed and the body weight was used to administer a body weight-corrected dose of peptide. An oral glucose tolerance test (OGTT) was performed after subjecting the animals to 4 hours of fasting. At 2, 4, 6, 8, 10 and 12 hours after single peptide or vehicle dosing an initial blood sample were taken (t=−0 min). Immediately thereafter, an oral dose of glucose (1 g/kg) was given and the animals were returned to their home cages (t=0). BG levels were measured at t=15 min, t=30 min, t=60 min and t=90 min. Immediately following blood sampling, all animals were sacrificed by $CO_2$ anesthesia followed by cervical dislocation.

Food Intake in Young Lean and Old Obese C57BL/6J Mice.

C57BL/6J mice were on a high fat diet for 11 days and C57BL/6J mice were on a high fat diet for 52 weeks.

3 days before study, the mice were transferred to individual cages and weighed. 4 days before study, they were acclimatized to handling and treatment by daily s.c. injections. On the day before the experiment food was removed at 20:00. On the day of the experiment, the mice were weighed and treated with s.c. injections of Exendin-4, Compound 7 or Vehicle at t=0 h (8:00) and t=12 h (20:00). Immediately after treatment (t=0), pre-weighed food were introduced to the mice and the cumulative food intake was measured by weighing the remaining food after t=1, 2, 4, 8, 12 and 24 hours. After weighing the food and the animals at t=24 h, the mice were sacrificed by cervical dislocation.

Hepatocyt cAMP Formation

Experimental Procedure

Primary human hepatocyts provided by Lonza Walkersvill, Inc. were carefully washed in TB buffer and incubated at 37° C. with peptides dissolved in TB buffer supplemented with 100 μM IBMX and 0.1% casein for 15 minutes. Prior to addition to the cells, the peptide dilutions were pre-warmed to 37° C. The reaction was stopped by addition of 25 μl of ice cold 0.5 M HCl, and the cells were incubated on ice for 60 min. The cAMP content in the wells was determined by adding 25 μl of the acid extracts from the wells to 75 μl sodium acetate buffer, pH 6.2, in 96-well microtiter "FlashPlates" coated with scintillant and anti-cAMP antibodies. Following addition of 100 μl of 10 μCi [$^{125}$I]cAMP solution to each well, the plates were incubated overnight at 4° C., emptied, and the amount of [$^{125}$I]cAMP bound to the FlashPlates was counted using the program "[$^{125}$I]cAMP flashplate 10 min" on the TopCount NXT.

Peptides were tested at a concentration range of 0.1-1000 nM.

Data Analysis and Statistics

The amount of cAMP produced by the cells was calculated by extrapolation to a cAMP standard curve.

$EC_{50}$ values were estimated by fitting the cAMP data to the below formula using Sigma Plot:

$$cAMP\ response = \frac{(cAMP_{max} - cAMP_{min}) \times c}{c + EC_{50}} + cAMP_{min},$$

The invention is further illustrated by the following examples.

Liver Weight/Body Weight of C57BL/6J Mice.

Mice were treated twice daily s.c. with Cpd. 1 and Cpd. 11 (at two doses: 0.5 and 5 nmol/kg) or vehicle for 2 weeks. Throughout the study, body weights were recorded daily and used to administer the body weight-corrected doses of peptide. On the day of sacrifice, the liver was exposed, and weighed.

EXAMPLES

Example 1: Synthesis of Compounds and Peptide Properties

Synthesis Example

Compound 9 was synthesized on a CEM Liberty Peptide Synthesizer using TentaGel S Ram resin (1.17 g; 0.23 mmol/g) and Fmoc-chemistry as described above. Fmoc-Lys(ivDde)-OH was used in position 17 and pseudoprolines Fmoc-Phe-Thr(.Psi. Me, Me pro)-OH and Fmoc-Asp (OtBu)-Ser(.Psi., Me, Me pro)-OH were used in the peptide backbone. After completion of the peptide backbone on the resin the N-terminal Fmoc-group was cleaved manually followed by Boc-protection using Boc$_2$O (226 mg) and DIEA (54 μl) in DCM. The ivDde-group was then cleaved with freshly prepared hydrazine hydrate/NMP (4%; 2×15 min.). Back on the CEM Liberty Peptide Synthesizer the remaining two building blocks, Fmoc-Glu-OtBu and hexadecanoic acid, were added to the unprotected lysine side chain.

The peptide was cleaved from the resin as described above, and the purification was performed on a Gemini-NX column (5 cm, 10 μm, C18) with a 35 ml/min flow of a mixture of buffer A (0.1% TFA, aq.) and buffer B (0.1% TFA, 90% MeCN, aq.). The product was eluted with a linear gradient from 25% to 65% buffer B over 47 min., and fractions (9 ml) were collected by a fraction collector. Relevant fractions were analysed by analytical HPLC and MS and fractions with purities above 95% were pooled and lyophilised to a white powder. The 72 mg yield had a purity of 97% determined by analytical HPLC and the mass was 3697.05 Da as determined by MS (Calc. 3696.97 Da).

Example 2: Efficacy on GLP-1 and Glucagon Receptors

Efficacy of the GluGLP-1 agonists were estimated by exposing cells expressing hGlucagonR and hGLP-1R to the listed acylated compounds at increasing concentrations and measuring the formed cAMP as described in Methods.

Results are shown in Table 1:

TABLE 1

| Sequence | Compound | $EC_{50}$ (nM) GLP-1R | $EC_{50}$ (nM) GluR |
|---|---|---|---|
| H-HSQGTFTSDYSKYLDSKAAHDFVEWLLRA-NH2 (SEQ ID NO: 13) | Compound 1 | 0.06 | 0.06 |
| H-HSQGTFTSDYSKYLD-K(Hexadecanoyl-γ-Glu)-KAAHDFVEWLLRA-NH2 (SEQ ID NO: 83) | Compound 2 | 0.20 | 0.13 |
| H-HSQGTFTSDYSKYLD-S-K(Hexadecanoyl-γ-Glu)-AAHDFVEWLLRA-NH2 (SEQ ID NO: 93) | Compound 3 | 0.11 | 0.12 |
| H-HSQGTFTSDYSKYLDSKAA-K(Hexadecanoyl-γ-Glu)-DFVEWLLRA-NH2 (SEQ ID NO: 85) | Compound 4 | 0.10 | 0.04 |
| H-HSQGTFTSDYSKYLDSKAAHDFVEWL-K(Hexadecanoyl-γ-Glu)-RA-NH2 (SEQ ID NO: 84) | Compound 5 | 0.57 | 0.22 |
| H-HSQGTFTSDYSKYLDSKAAHDFVEWLL-K(Hexadecanoyl-γ-Glu)-A-NH2 (SEQ ID NO: 86) | Compound 6 | 0.09 | 0.10 |

TABLE 1-continued

EC$_{50}$ values of acylated compounds at GLP-1 and Glucagon receptors

| Sequence | Compound | EC$_{50}$ (nM) GLP-1R | EC$_{50}$ (nM) GluR |
| --- | --- | --- | --- |
| H-H-Aib-QGTFTSDYSKYLDS-K(Hexadecanoyl-γ-Glu)-AAHDFVEWLLSA-NH2 (SEQ ID NO: 89) | Compound 7 | 0.11 | 0.16 |
| H-H-Aib-QGTFTSDYSKYLDS-K(Hexadecanoyl-γ-Glu)-AARDFVAWLLRA-NH2 (SEQ ID NO: 88) | Compound 9 | 0.12 | 0.17 |
| H-H-Aib-QGTFTSDYSKYLDSKAA-K(Hexadecanoyl-γ-Glu)-DFVAWLLRA-NH2 (SEQ ID NO: 94) | Compound 10 | 0.15 | 0.63 |
| H-H-Aib-QGTFTSDYSKYLDS-K(Hexadecanoyl-γ-Glu)-AAHDFVEWLLRA-NH2 (SEQ ID NO: 87) | Compound 11 | 0.09 | 0.16 |
| H-H-Aib-QGTFTSDYSKYLDSKAAHDFVEWLL-K(Hexadecanoyl-γ-Glu)-A-NH2 (SEQ ID NO: 90) | Compound 12 | 0.27 | 0.27 |
| H-H-Aib-QGTFTSDYSKYLDS-K(Hexadecanoyl-γ-Glu)-AAHDFVE( )WLLK( )A-NH2 (SEQ ID NO: 91) | Compound 13 | 0.08 | 0.26 |
| H-H-Aib-QGTFTSDYSKYLDS-K(Dodecanoyl-γ-Glu)-AAHDFVEWLLSA-NH2 (SEQ ID NO: 95) | Compound 14 | 0.14 | 0.78 |
| H-H-Aib-QGTFTSDYSKYLDS-K(Hexadecanoyl-[3-Aminopropanoyl])-AAHDFVEWLLSA-NH2 (SEQ ID NO: 96) | Compound 15 | 0.23 | 1.87 |
| H-H-Aib-QGTFTSDYSKYLDS-K(Hexadecanoyl-[8-Aminooctanoyl])-AAHDFVEWLLSA-NH2 (SEQ ID NO: 97) | Compound 16 | 0.24 | 0.46 |
| H-H-Aib-QGTFTSDYSKYLDS-K(Hexadecanoyl-ε-Lys)-AAHDFVEWLLSA-NH2 (SEQ ID NO: 98) | Compound 17 | 0.09 | 0.39 |

The residues marked ( ) form an intramolecular lactam ring.

TABLE 1a

EC$_{50}$ values of additional acylated compounds according to the invention

| Sequence | Compound | EC$_{50}$ (nM) GLP-1R | EC$_{50}$ (nM) GluR |
| --- | --- | --- | --- |
| H-H-Aib-QGTFTSDYSKYLDS-K(Hexadecanoyl-isoGlu)-AAHDFVEWLLS-OH (SEQ ID NO: 121) | Compound 18 | 0.066 | 0.091 |
| H-H-Aib-QGTFTSDYSKYLDS-K(Hexadecanoyl-isoGlu)-AAHDFVEWLL-OH (SEQ ID NO: 122) | Compound 19 | 0.048 | 0.483 |
| H-H-Aib-EGTFTSDYSKYLDS-K(Hexadecanoyl-isoGlu)-AAHDFVEWLLSA-OH (SEQ ID NO: 123) | Compound 20 | 0.057 | 13.266 |
| H-H-Aib-QGTFTSDYSKYLDS-K(Hexadecanoyl-isoGlu)-AAHDFVEWLLSA-OH (SEQ ID NO: 124) | Compound 21 | 0.077 | 0.150 |
| H-H-Aib-EGTFTSDYSKYLDS-K(Hexadecanoyl-isoGlu)-AAHDFVEWLLSA-NH2 (SEQ ID NO: 123) | Compound 22 | 0.014 | 26.370 |
| H-H-Aib-QGTFTSDYSKYLDS-K(Hexadecanoyl)-AAHDFVEWLLSA-NH2 (SEQ ID NO: 105) | Compound 23 | 0.140 | 0.124 |
| H-H-Aib-QGTFTSDYSKYLDS-K([2-Butyloctanoyl]-isoGlu)-AAHDFVEWLLSA-NH2 (SEQ ID NO: 125) | Compound 24 | 0.161 | 0.133 |
| H-H-Aib-QGTFTSDYSKYLDS-K(Octadecanoyl-isoGlu)-AAHDFVEWLLSA-NH2 (SEQ ID NO: 126) | Compound 25 | 0.069 | 0.103 |
| H-H-Aib-QGTFTSDYSKYLDS-K(Dodecanoyl-isoGlu)-AAHDFVEWLLSA-NH2 (SEQ ID NO: 127) | Compound 26 | 0.097 | 0.116 |

TABLE 1a-continued

EC$_{50}$ values of additional acylated compounds according to the invention

| Sequence | Compound | EC$_{50}$ (nM) GLP-1R | EC$_{50}$ (nM) GluR |
|---|---|---|---|
| H-H-Aib-QGTFTSDYSKYLDS-K(Hexadecanoyl-[4-Aminobutanoyl])-AAHDFVEWLLSA-NH2 (SEQ ID NO: 108) | Compound 27 | 0.152 | 0.147 |
| H-H-Aib-QGTFTSDYSKYLDS-K(Hexadecanoyl-E)-AAHDFVEWLLSA-NH2 (SEQ ID NO: 110) | Compound 28 | 0.149 | 0.108 |
| H-H-Aib-QGTFTSDYSKYLDS-K(Hexadecanoyl-[8-Aminooctanoyl])-AAHDFVEWLLSA-NH2 (SEQ ID NO: 97) | Compound 29 | 0.199 | 0.123 |
| H-H-Aib-QGTFTSDYSKYLDS-K(Hexadecanoyl-isoLys)-AAHDFVEWLLSA-NH2 (SEQ ID NO: 128) | Compound 30 | 0.132 | 0.110 |
| H-H-Aib-QGTFTSDYSKYLDS-K(Hexadecanoyl-[3-Aminopropanoyl])-AAHDFVEWLLSA-NH2 (SEQ ID NO: 96) | Compound 31 | 0.103 | 0.151 |
| H-H-Aib-QGTFTSDYSKYLDS-Orn(Hexadecanoyl-isoGlu)-AAHDFVEWLLSA-NH2 (SEQ ID NO: 129) | Compound 32 | 0.195 | 0.193 |
| H-H-Aib-QGTFTSDYS-K(Hexadecanoyl-isoGlu)-YLDSKAAHDFVEWLLSA-NH2 (SEQ ID NO: 111) | Compound 33 | 0.131 | 0.389 |
| H-H-Aib-QGTFTSDYSKYLD-K(Hexadecanoyl-isoGlu)-KAAHDFVEWLLSA-NH2 (SEQ ID NO: 112) | Compound 34 | 0.109 | 0.053 |
| H-H-Aib-QGTFTSDYSKYLDSKAA-K(Hexadecanoyl-isoGlu)-DFVEWLLSA-NH2 (SEQ ID NO: 113) | Compound 35 | 0.202 | 0.180 |
| H-H-Aib-QGTFTSDYSKYLDSKAAHDFV-K(Hexadecanoyl-isoGlu)-WLLSA-NH2 (SEQ ID NO: 114) | Compound 36 | 0.191 | 0.213 |
| H-H-Aib-QGTFTSDYSKYLDSKAAHDFVEWLL-K(Hexadecanoyl-isoGlu)-A-NH2 (SEQ ID NO: 130) | Compound 37 | 0.207 | 0.147 |
| H-H-Aib-QGTFTSDYSKYLDS-K(Hexadecanoyl-isoLys)-AARDFVAWLLRA-NH2 (SEQ ID NO: 115) | Compound 38 | 0.132 | 0.183 |
| H-H-Aib-QGTFTSDYSKYLDS-K(Hexadecanoyl-isoGlu)-AAKDFVEWLLSA-NH2 (SEQ ID NO: 116) | Compound 39 | 0.16 | 0.24 |
| H-H-Aib-QGTFTSDYSKYLDE-K(Hexadecanoyl-isoGlu)-AAHDFVEWLLSA-NH2 (SEQ ID NO: 117) | Compound 40 | 0.20 | 0.18 |
| H-H-Aib-QGTFTSDYSKYLDS-K(Hexadecanoyl-isoGlu)-AAHEFVEWLLSA-NH2 (SEQ ID NO: 118) | Compound 41 | 0.13 | 0.08 |
| H-H-Aib-QGTFTSDYSKYLDS-K(Hexadecanoyl-isoGlu)-AAEDFVEWLLSA-NH2 (SEQ ID NO: 119) | Compound 42 | 0.03 | 0.27 |
| H-H-Aib-QGTFTSDYSKYLDS-K(Hexadecanoyl-isoGlu)-AAHDFVEWLLEA-NH2 (SEQ ID NO: 120) | Compound 43 | 0.082 | 0.12 |

For compound 28 H—H-Aib-QGTFTSDYSKYLDS-K(Hexadecanoyl-E)-AAHDFVEWLLSA-NH2 (SEQ ID NO:110) could also be written as H—H-Aib-QGTFTSDYSKYLDS-K(Hexadecanoyl-αGlu)-AAHDFVEWLLSA-NH2.

Example 3: Pharmacokinetic Screening

Pharmacokinetic profiles were determined for various acylated compounds. Calculated T$_{1/2}$ values are shown in Table 2, compared to (non-acylated) compound 1.

TABLE 2

| Compound | T$_{1/2}$ (h) |
|---|---|
| 1 | 0.23 |
| 2 | 5.8 |
| 5 | 5.3 |
| 4 | 2.0* |
| 6 | 4.8 |
| 7 | 3.4 |
| 9 | 2.4* |
| 11 | 4.9 |
| 12 | 6.0 |
| 13 | 6.4 |

*Only two time points were used for calculation of T½.

All of the acylated compounds have improved T½ compared to compound 1.

A sample pharmacokinetic profile, for compound 13, is shown in FIG. 1.

Example 4: Oral Glucose Tolerance Test in DIO Mice

Effect of 21 days s.c. administration of compound 11 (10 nmol/kg) on oral glucose tolerance in long term high fat-fed C57BL/6J mice. High fat-fed mice were fasted and an initial blood sample taken to determine fasting blood glucose level (t=0). An oral dose of glucose (1 g/kg in 5 ml/kg) was then given and blood glucose levels were measured at t=30 min, t=60 min, t=90 min and t=120 min. Compound 11 significantly improved glucose tolerance (two way ANOVA). Data are shown as mean±SEM.

Example 5: HbA1c in Db/Db Mice after 28 Days

Figure 3:
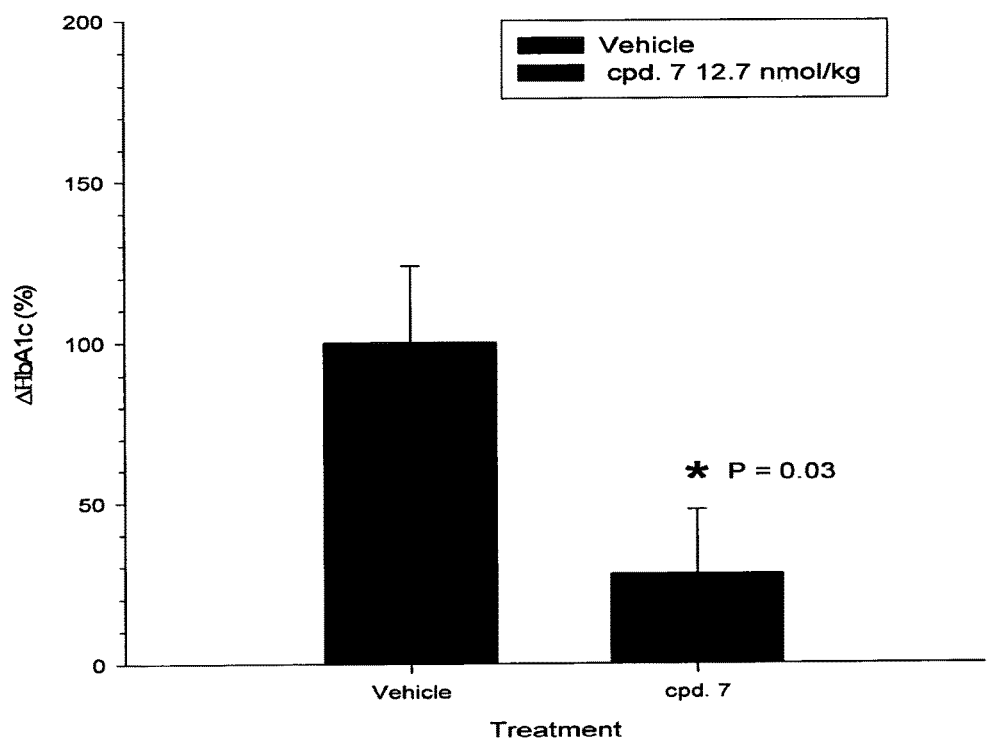
FIG. 3. Diabetic (db/db) mice were treated with vehicle or compound 7 (12.7 nmol/kg) for 4 weeks and HbA1c was determined (Cobas® application note: A1C-2) in whole blood samples (20 µl) collected from the treated mice. The ΔHbA1c (%) was calculated for each mouse by subtracting its HbA1c (%) at start of treatment from HbA1c (%) at 4 weeks. ΔHbA1c (%) of db/db mice treated for 4 weeks with vehicle=100%. * ($P=0.03$, Students t-test).

Diabetic (db/db) mice were treated with vehicle or compound 7 for 4 weeks, and HbA1c was determined (Cobas® application note: A1C-2) in whole blood samples (20 µl) collected from the treated mice. Results are shown in FIG. 3. The ΔHbA1c (%) was calculated for each mice by subtracting its HbA1c (%) at start of treatment from HbA1c (%) at 4 weeks. Treatment with compound 7 decreased ΔHbA1c (%) significantly. (P=0.03; Students t-test) compared to vehicle.

Example 6: Reduced Body Weight

Figure 4:
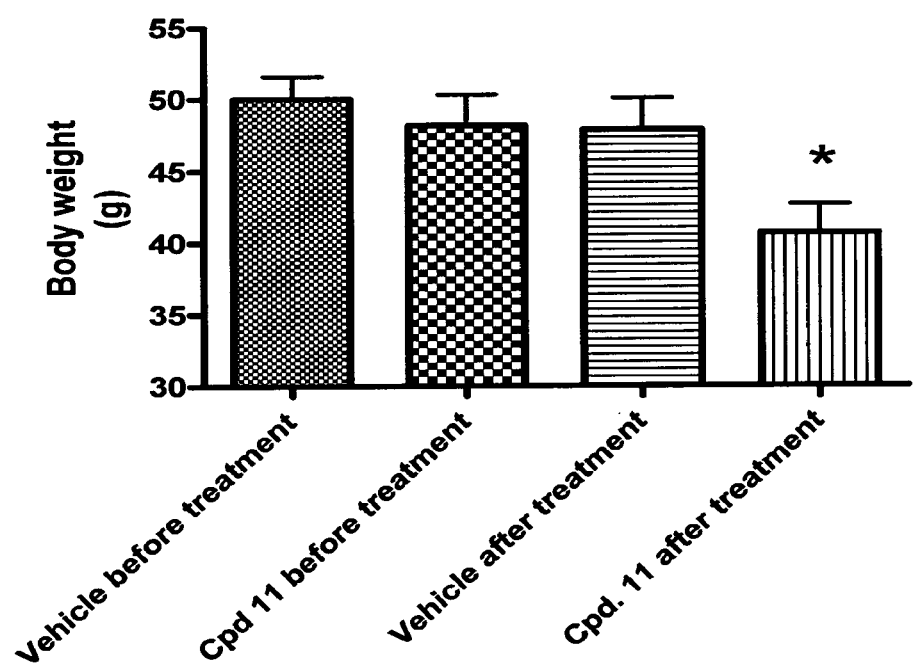
FIG. 4. Effect of 21 days s.c. administration of compound 11 on body weight in long term high fat fed C57BL/6J mice. Data are shown as mean+SEM.

Effect of 21 days s.c. administration of compound 11 on body weight was determined in long term high fat-fed C57BL/6J mice. C57Bl/6J male mice on high fat diet (HFD) were treated (b.i.d.; s.c.) with compound 11 (10 nmol/kg) or vehicle. Body weights were recorded daily and used to administer the body weight-corrected doses of peptide throughout the study. Data are shown as mean±SEM in FIG. 4. Compound 11 significantly decreased body weight ($p<0.05$).

Example 7: Total Cholesterol and HDL/LDL Ratio

Figure 5:
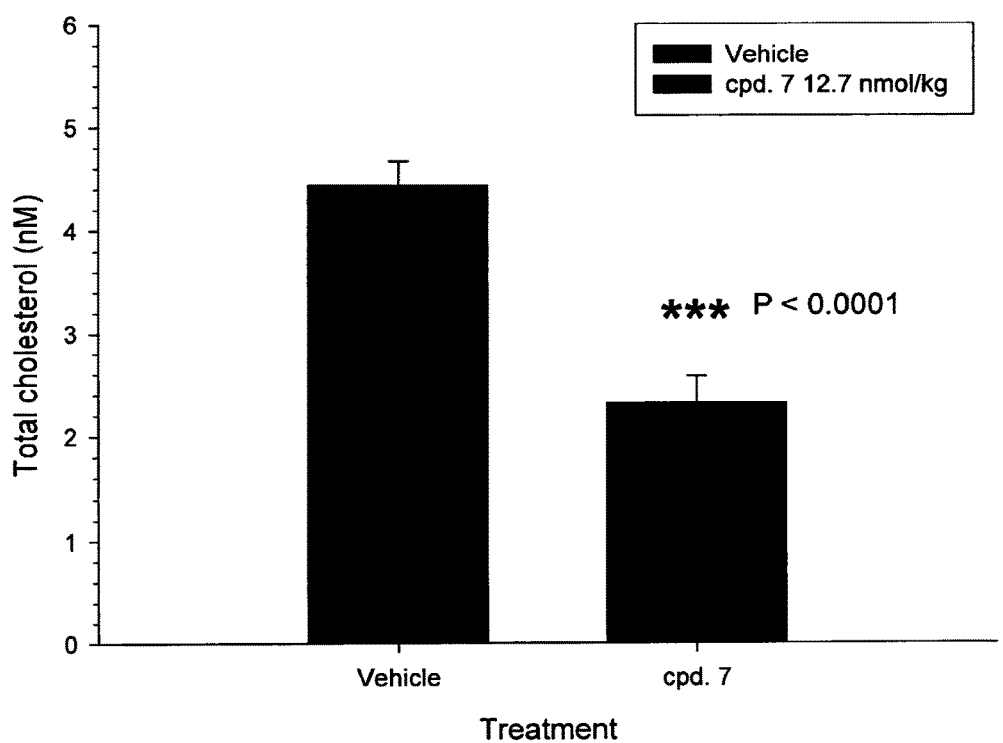
FIG. 5. Diet Induced Obese (DIO) mice were treated with vehicle or compound 7 (12.7 nmol/kg) for 4 weeks and plasma prepared from the collected blood samples. Total cholesterol was determined in each plasma sample (Cobas®; application note CHOL2). *** ($P<0.0001$, Students t-test). Data are shown as mean+SEM.
Figure 6:
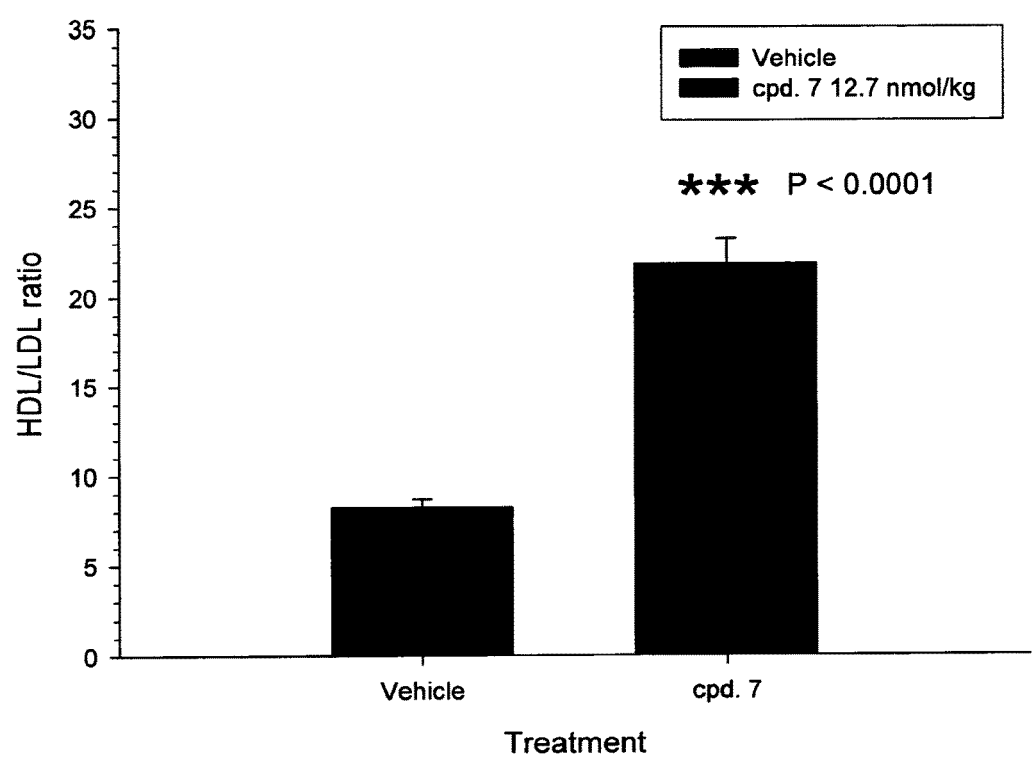
FIG. 6. Diet Induced Obese (DIO) mice were treated with vehicle or compound 7 (12.7 nmol/kg) and plasma prepared from the collected blood samples. LDL and HDL cholesterol were determined in each plasma sample (Cobas®; application notes HDLC3 and LDL_C). *** ($P<0.0001$, Students t-test). Data are shown as mean+SEM.

Diet Induced Obese (DIO) mice were treated with vehicle or compound 7 for 4 weeks and plasma prepared from the collected blood samples. The total cholesterol, LDL and HDL were determined in each plasma sample (Cobas® application notes: CHOL2, HDLC3 and LDL_C) and results are shown in FIGS. 5 and 6. Treatment with compound 7 significantly (P<0.0001, Students t-test) decreased total cholesterol concentrations (FIG. 5) and significantly (P<0.0001, Students t-test) increased the HDL/LDL-ratio (FIG. 6).

Example 8: Body Weight Gain in High Fat Fed C57BL/6J Mice

Effect of 10 days s.c. administration of Exendin-4, Compound 8, Compound 3, Compound 7, Compound 11, Compound 12 and Compound 6 short term high fat-fed C57BL/6J mice. C57Bl/6J male mice on high fat diet (HFD) were treated (b.i.d.; s.c.) (0.5 and 5 nmol/kg) or vehicle. Body weights were recorded daily and used to administer the body weight-corrected doses of peptide throughout the study. Data are shown as mean±SEM in FIG. 7.

Figure 7:
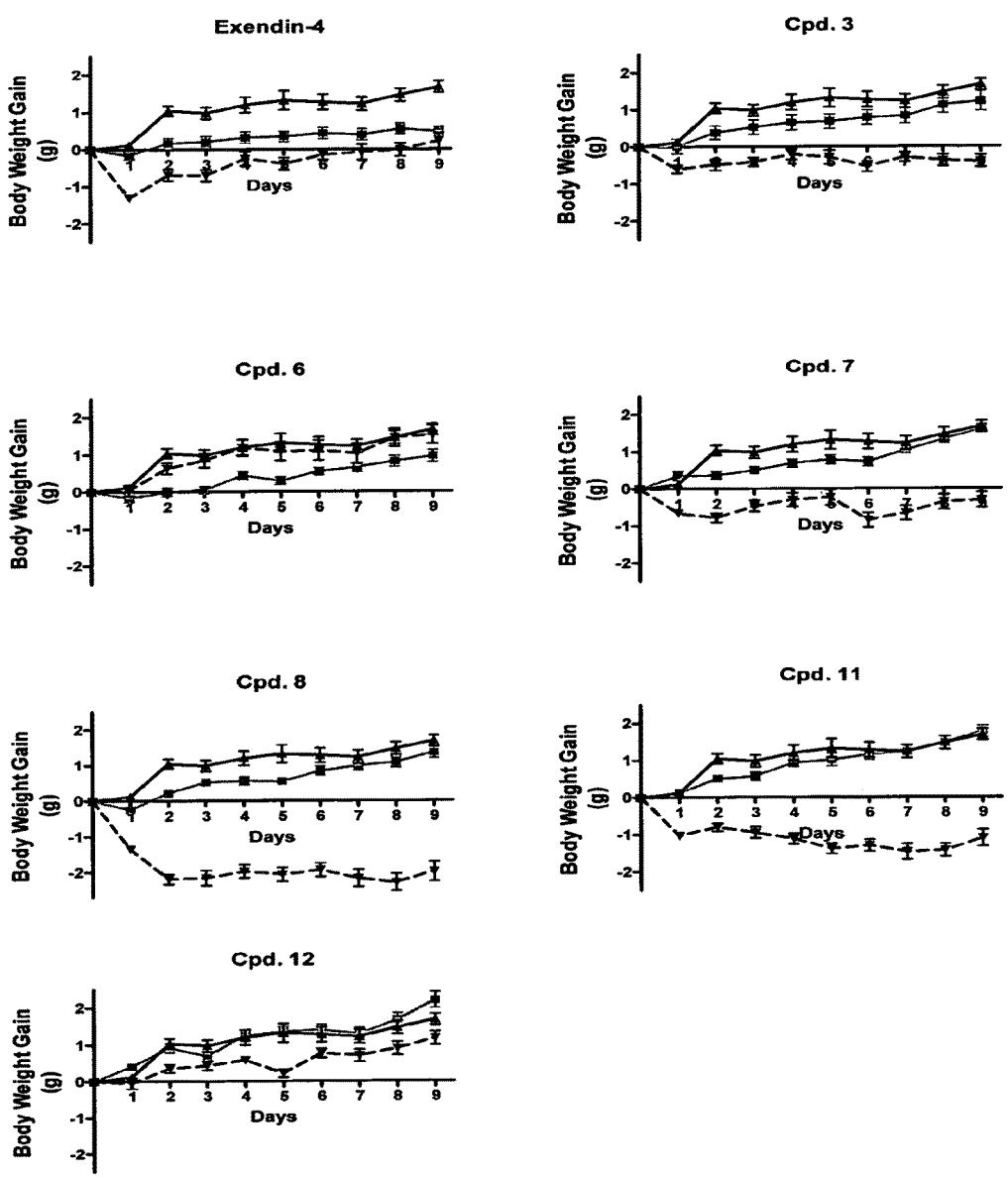
FIG. 7. Effect of s.c. administration of GluGLP-1 agonists on body weight gain in high fat fed C57BL/6J mice. Data are mean±SEM. Black line: Vehicle (PBS), Grey line: Low dose (0.5 nmol/kg), Broken line: High dose (5 nmol/kg).
Figure 8:
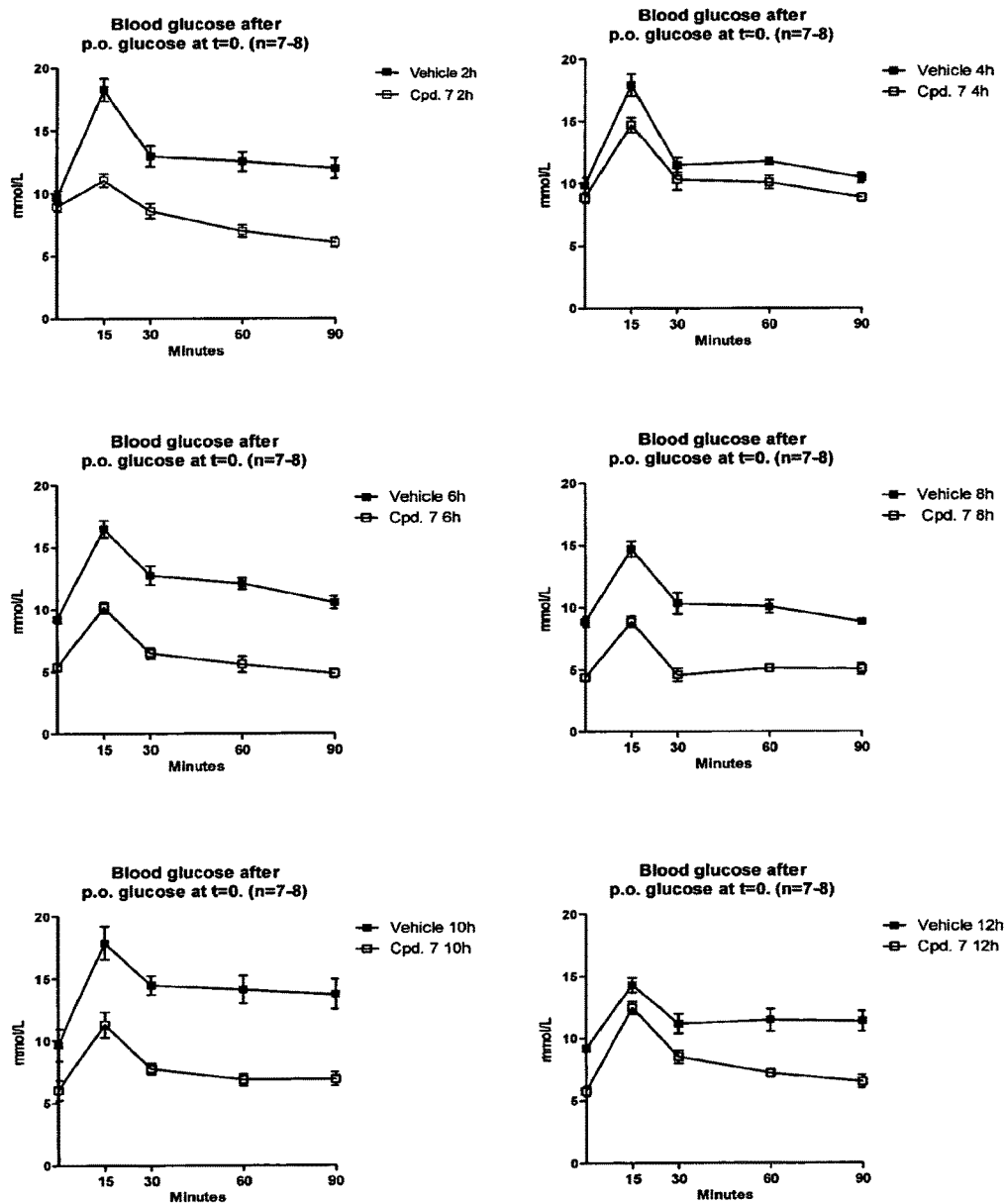
FIG. 8. Effect of acute s.c. administration of Compound 7 on oral glucose tolerance 2, 4, 6, 8, 10 and 12 h after dosing in high fat fed C57BL/6J mice. Data are expressed as mean+SEM.
Figure 9:
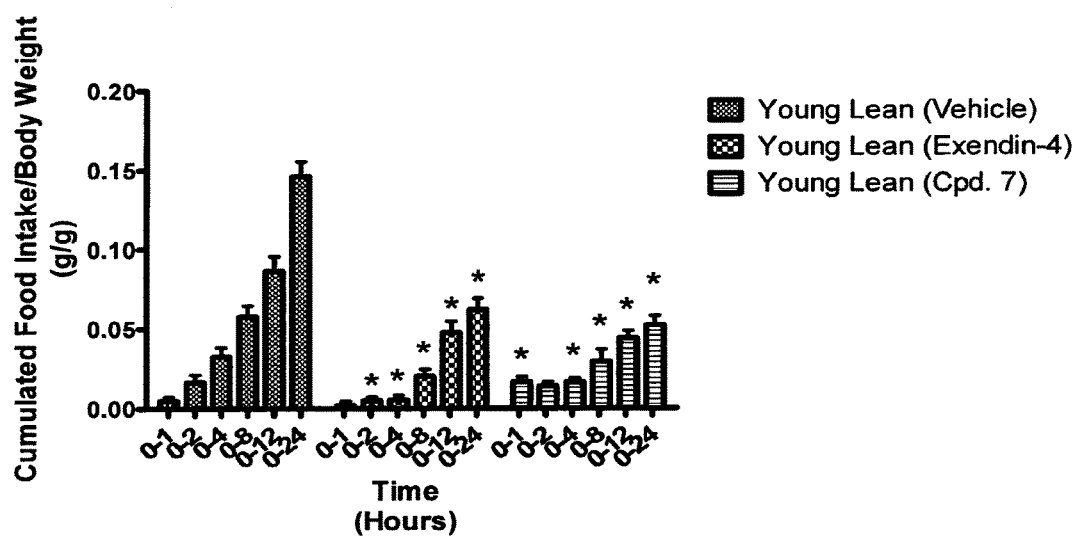
FIG. 9. Effect of s.c. administration of Compound 7 and exendin-4 on food intake/body weight in young lean C57BL/6J mice. Data are mean+SEM. *=$p<0.05$ versus young lean vehicle. Data are expressed as mean+SEM.
Figure 10:
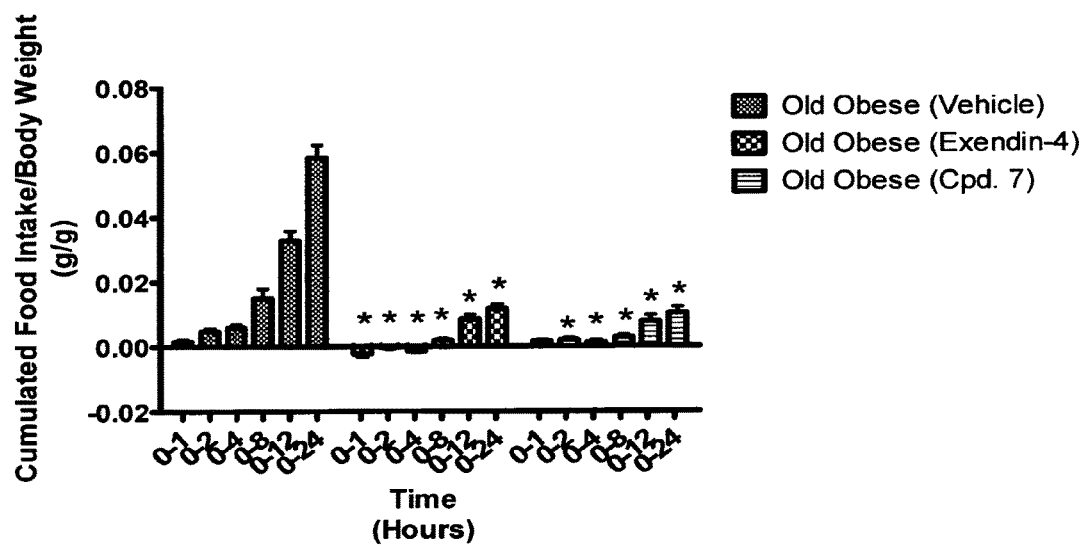
FIG. 10. Effect of s.c. administration of Compound 7 and exendin-4 on cumulative food intake/body weight in old obese C57BL/6J mice. Data are mean+SEM. *=$p<0.05$ versus old obese vehicle. Data are expressed as mean+SEM.

The control peptide (exendin-4) as well as Compound 8, significantly decreased body weight gain at both doses (0.5 and 5 nmol/kg). Compound 3, Compound 7, Compound 11 and Compound 12 significantly decreased body weight gain at the high dose (5 nmol/kg) but not at the low dose (0.5 nmol/kg) (FIG. 7). Compound 6 significantly decreased body weight gain only at the low dose (0.5 nmol/kg).

Example 9: Oral Glucose Tolerance 2, 4, 6, 8, 10 and 12 h after Dosing in High Fat Fed C57BL/6J An oral glucose tolerance test (OGTT) was performed after subjecting the animals to 4 hours of fasting. At 2, 4, 6, 8, 10 and 12 hours after Compound 7 or vehicle dosing an initial blood sample were taken (t=−0 min). Immediately thereafter, an oral dose of glucose (1 g/kg) was given. BG levels were measured at t=15 min, t=30 min, t=60 min and t=90 min. Immediately following blood sampling, all animals were sacrificed by $CO_2$ anesthesia followed by cervical dislocation.

The study shows that subcutaneous administration with Compound 7 (10 nmol/kg) significantly improves glucose tolerance (measured as decreased AUC during an oral glucose tolerance test) 2, 4, 6, 8, 10 and 12 hours after dosing in high fat fed C57BL/6J mice.

Example 10: Food Intake in Young Lean and Old Obese C57BL/6J Mice

C57BL/6J mice were on a high fat diet for 11 days and C57BL/6J mice were on a high fat diet for 52 weeks.

On the day of the experiment, the mice were weighed and treated with s.c. injections of Exendin-4, Compound 7 or Vehicle at t=0 h (8:00) and t=12 h (20:00). Immediately after treatment (t=0), pre-weighed food were introduced to the mice and the cumulative food intake was measured by weighing the remaining food after t=1, 2, 4, 8, 12 and 24 hours.

In the young lean mice, Compound 7 statistically significantly ($p<0.05$) reduced food intake during the 0-4, 0-8, 0-12 and 0-24 time periods. Exendin-4 statistically significantly ($p<0.05$) reduced food intake during the 0-2, 0-4, 0-8, 0-12 and 0-24 time periods.

In the old obese mice, Compound 7 statistically significantly ($p<0.05$) reduced food intake during the 0-2, 0-4, 0-8, 0-12 and 0-24 time periods. Exendin-4 statistically significantly ($p<0.05$) reduced food intake in all time periods.

Figure 11:
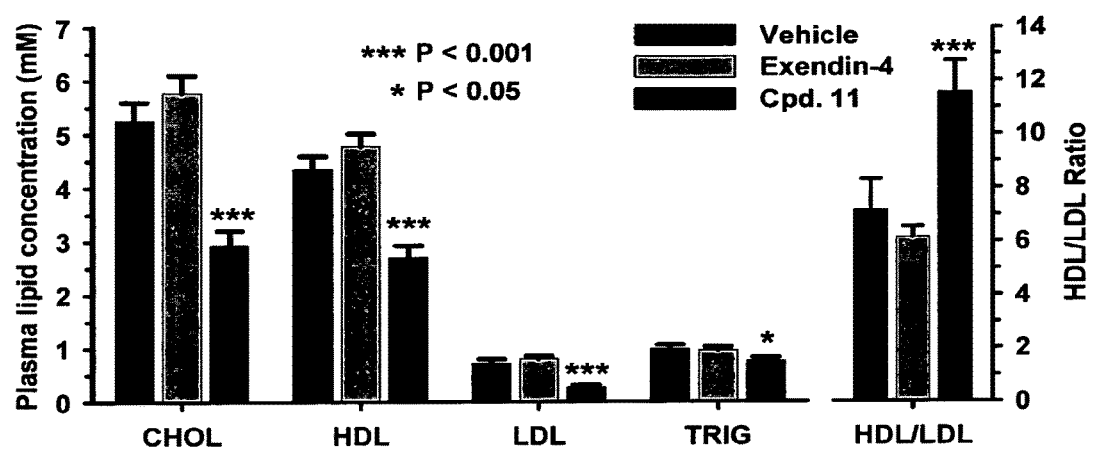
FIG. 11. Effect of s.c. administration of Vehicle, exendin-4 (10 nmol/kg) and Compound 11 (10 nmol/kg) on plasma lipid concentration in old obese C57BL/6J mice. Data are mean+SEM.

Example 11: Effect of 3 Weeks Subcutaneous Administration of GluGLP-1 Agonist Compound 11 on Lipids in 30 Weeks High Fat Diet Feeded Mice Effect of 3 weeks treatment of mice that have been on 30 weeks High Fat Diet for 30 weeks prior treatment (s.c.) with vehicle (PBS), 10 nmol/kg exendin-4 or 10 nmol/kg Compound 11 twice daily for 3 weeks on lipids (FIG. 11). The effect was measured on LDL, HDL and triglycerids (CHO: Total Cholesterol; HDL: High Density Cholesterol; LDL: Low Density Cholesterol; TRIG: Triglycerides; HDL/LDL: Ratio between HDL and LDL).

Compound 11 significantly decreased cholesterol, HDL, LDL (P<0.001) and triglycerides (P<0.05) significantly, while the ratio HDL/LDL was increased significantly (p<0.001) (FIG. 11). The HDL/LDL ratio is considered a risk indicator for heart disease. The the higher the ratio, the lower the risk of heart attack or other cardiovascular problems.

Example 12: Effect of Compound 11 on Hepatocyt cAMP Formation

All tested peptides behaved as full agonist with respect to GluR stimulated cAMP formation except of the pure GLP-1 agonists exendin-4 and liraglutide. From the table it can observed that the rank order of potency is: Compound 1>glucagon>Compound 11>oxyntomodulin>>>exendin-4 and liraglutide (Table 9).

Finally, no down regulation was observed of the $E_{MAX}$ cAMP response at the high concentrations, which is in contrast to what is observed in the hGluR HEK293 cells.

TABLE 9

Glucagon agonist effect on cAMP formation in human primary cultures.

| Peptide | Compound No | GluR $EC_{50}$ (nM) | | |
|---|---|---|---|---|
| | | (1) | (2) | (log avg) |
| Exendin-4 | | ∞ | ∞ | ∞ |
| Glucagon | | 2.1 | 7.7 | 4.0 |
| Oxyntomodulin | | 194.5 | 222.7 | 208.1 |
| | 1 | 1.4 | 2.2 | 1.8 |
| | 11 | 32.9 | 25.5 | 28.9 |
| Liraglutide | | ∞ | ∞ | ∞ |

Example 13: Liver Weight of C57 Healthy Control Mice Treated for 2 Weeks

Figure 12:
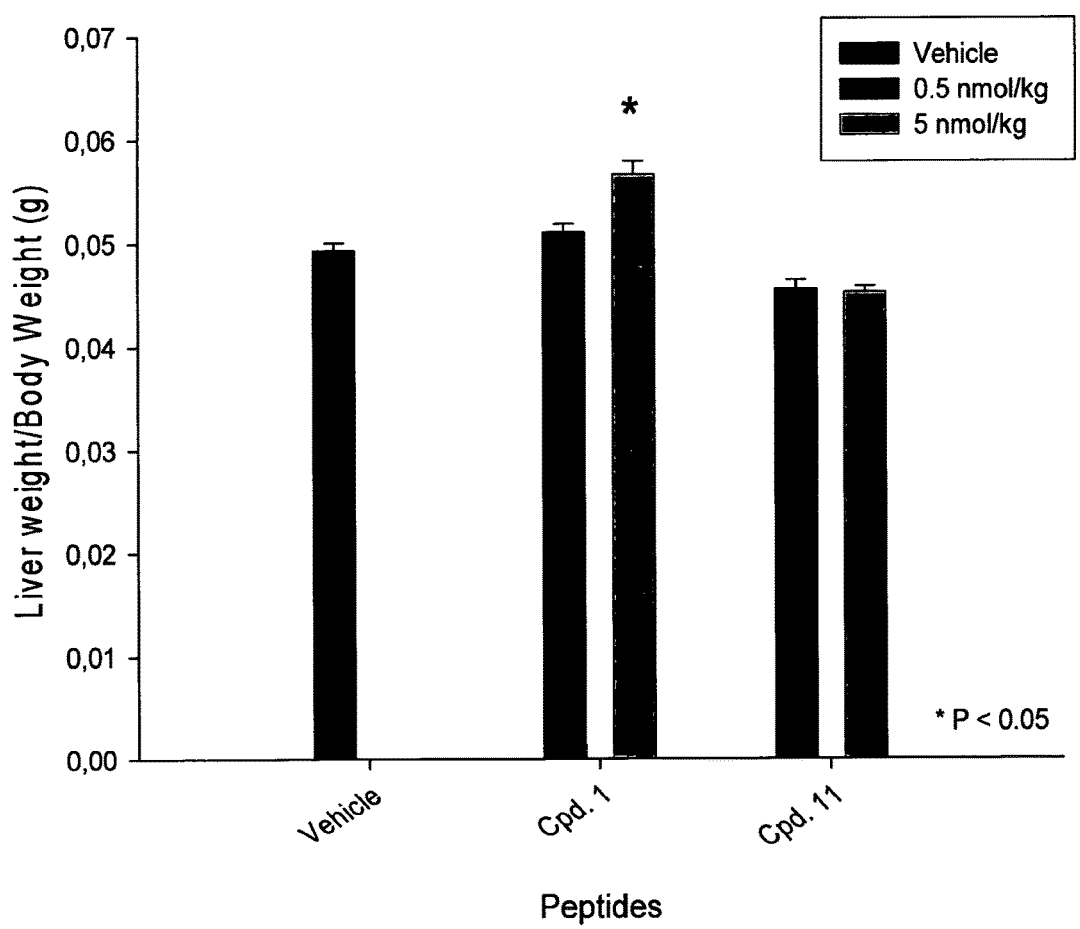
FIG. 12. Mice were treated twice daily s.c. with Compound. 1 and Compound. 11 (at two doses: 0.5 and 5 nmol/kg) or vehicle for 2 weeks. On the day of sacrifice, the liver was exposed, and weighed. Compound 1 significantly increased "liver weight/body weight ratio" at the high dose. Compound. 11 did not affect "liver weight/body weight ratio" at the two doses (0.5 and 5 nmol/kg). Compound 1 is a non-acylated dual GluGLP-1 agonists and Compound. 11 is a long-acting acylated dual GluGLP-1 agonists (FIG. 12).

Repeated treatment with long-acting acylated dual GluGLP-1 agonists such as Compound 11 do not give rise to change in liver size (enlarged or shrunken) compared with the non-acylated dual GluGLP-1 agonists compound 1 (FIG. 12).

Example 14: HbA1c in Db/Db Mice after 28 Days

Figure 13:
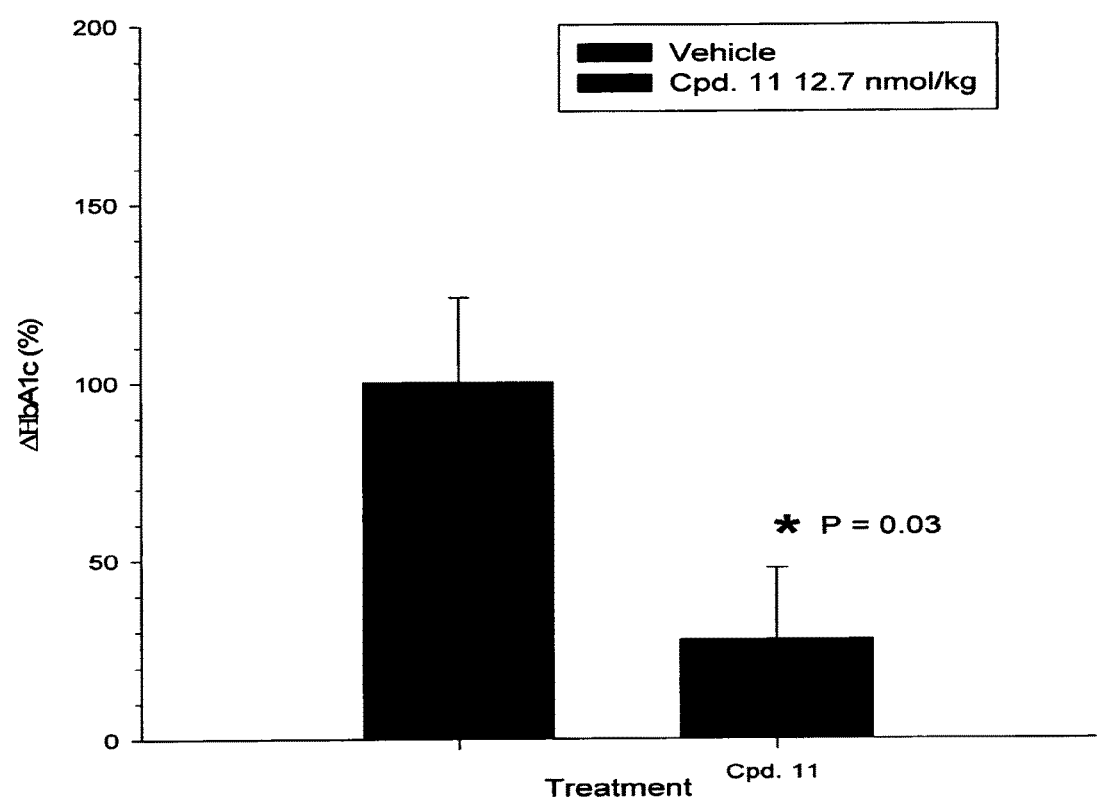
FIG. 13. Diabetic (db/db) mice were treated with vehicle or compound 11 (12.7 nmol/kg) for 4 weeks and HbA1c was determined (Cobas® application note: A1C-2) in whole blood samples (20 µl) collected from the treated mice. The ΔHbA1c (%) was calculated for each mouse by subtracting its HbA1c (%) at start of treatment from HbA1c (%) at 4 weeks. ΔHbA1c (%) of db/db mice treated for 4 weeks with vehicle=100%. * (P=0.03, Students t-test).

Diabetic (db/db) mice were treated with vehicle or compound 11 for 4 weeks, and HbA1c was determined (Cobas® application note: A1C-2) in whole blood samples (20 µl) collected from the treated mice. Results are shown in FIG. 13. The ΔHbA1c (%) was calculated for each mice by subtracting its HbA1c (%) at start of treatment from HbA1c (%) at 4 weeks. Treatment with compound 11 decreased ΔHbA1c (%) significantly. (P=0.03; Students t-test) compared to vehicle.

The invention claimed is:

1. A compound selected from:

(SEQ ID NO: 83)
H-HSQGTFTSDYSKYLD-K(Hexadecanoyl-γ-Glu)-KAAHDFVEWLLRA-NH2;

(SEQ ID NO: 85)
H-HSQGTFTSDYSKYLDSKAA-K(Hexadecanoyl-γ-Glu)-DFVEWLLRA-NH2;

(SEQ ID NO: 84)
H-HSQGTFTSDYSKYLDSKAAHDFVEWL-K(Hexadecanoyl-γ-Glu)-RA-NH2;

(SEQ ID NO: 86)
H-HSQGTFTSDYSKYLDSKAAHDFVEWLL-K(Hexadecanoyl-γ-Glu)-A-NH2;

(SEQ ID NO: 88)
H-H-Aib-QGTFTSDYSKYLDS-K(Hexadecanoyl-γ-Glu)-AARDFVAWLLRA-NH2;

(SEQ ID NO: 94)
H-H-Aib-QGTFTSDYSKYLDSKAA-K(Hexadecanoyl-γ-Glu)-DFVAWLLRA-NH2;

(SEQ ID NO: 87)
H-H-Aib-QGTFTSDYSKYLDS-K(Hexadecanoyl-γ-Glu)-AAHDFVEWLLRA-NH2;

(SEQ ID NO: 90)
H-H-Aib-QGTFTSDYSKYLDSKAAHDFVEWLL-K(Hexadecanoyl-γ-Glu)-A-NH2;

(SEQ ID NO: 91)
H-H-Aib-QGTFTSDYSKYLDS-K(Hexadecanoyl-γ-Glu)-AAHDFVE( )WLLK( )A-NH2;

(SEQ ID NO: 95)
H-H-Aib-QGTFTSDYSKYLDS-K(Dodecanoyl-γ-Glu)-AAHDFVEWLLSA-NH2;

(SEQ ID NO: 96)
H-H-Aib-QGTFTSDYSKYLDS-K(Hexadecanoyl-[3-Aminopropanoyl])-AAHDFVEWLLSA-NH2;

(SEQ ID NO: 97)
H-H-Aib-QGTFTSDYSKYLDS-K(Hexadecanoyl-[8-Aminooctanoyl])-AAHDFVEWLLSA-NH2;

(SEQ ID NO: 98)
H-H-Aib-QGTFTSDYSKYLDS-K(Hexadecanoyl-ε-Lys)-AAHDFVEWLLSA-NH2;

(SEQ ID NO: 121)
H-H-Aib-QGTFTSDYSKYLDS-K(Hexadecanoyl-isoGlu)-AAHDFVEWLLS-OH;

(SEQ ID NO: 122)
H-H-Aib-QGTFTSDYSKYLDS-K(Hexadecanoyl-isoGlu)-AAHDFVEWLL-OH;

(SEQ ID NO: 123)
H-H-Aib-EGTFTSDYSKYLDS-K(Hexadecanoyl-isoGlu)-AAHDFVEWLLSA-OH;

(SEQ ID NO: 124)
H-H-Aib-QGTFTSDYSKYLDS-K(Hexadecanoyl-isoGlu)-AAHDFVEWLLSA-OH;

(SEQ ID NO: 123)
H-H-Aib-EGTFTSDYSKYLDS-K(Hexadecanoyl-isoGlu)-AAHDFVEWLLSA-NH2;

(SEQ ID NO: 105)
H-H-Aib-QGTFTSDYSKYLDS-K(Hexadecanoyl)-AAHDFVEWLLSA-NH2;

(SEQ ID NO: 125)
H-H-Aib-QGTFTSDYSKYLDS-K([2-Butyloctanoyl]-isoGlu)-AAHDFVEWLLSA-NH2;

(SEQ ID NO: 126)
H-H-Aib-QGTFTSDYSKYLDS-K(Octadecanoyl-isoGlu)-AAHDFVEWLLSA-NH2;

(SEQ ID NO: 127)
H-H-Aib-QGTFTSDYSKYLDS-K(Dodecanoyl-isoGlu)-AAHDFVEWLLSA-NH2;

(SEQ ID NO: 108)
H-H-Aib-QGTFTSDYSKYLDS-K(Hexadecanoyl-[4-Aminobutanoyl])-AAHDFVEWLLSA-NH2;

(SEQ ID NO: 110)
H-H-Aib-QGTFTSDYSKYLDS-K(Hexadecanoyl-E)-AAHDFVEWLLSA-NH2;

(SEQ ID NO: 97)
H-H-Aib-QGTFTSDYSKYLDS-K(Hexadecanoyl-[8-Aminooctanoyl])-AAHDFVEWLLSA-NH2;

(SEQ ID NO: 30)
H-H-Aib-QGTFTSDYSKYLDS-K(Hexadecanoyl-isoLys)-AAHDFVEWLLSA-NH2;

(SEQ ID NO: 96)
H-H-Aib-QGTFTSDYSKYLDS-K(Hexadecanoyl-[3-Aminopropanoyl])-AAHDFVEWLLSA-NH2;

(SEQ ID NO: 129)
H-H-Aib-QGTFTSDYSKYLDS-Orn(Hexadecanoyl-isoGlu)-AAHDFVEWLLSA-NH2;

(SEQ ID NO: 111)
H-H-Aib-QGTFTSDYS-K(Hexadecanoyl-isoGlu)-YLDSKAAHDFVEWLLSA-NH2;

(SEQ ID NO: 112)
H-H-Aib-QGTFTSDYSKYLD-K(Hexadecanoyl-isoGlu)-KAAHDFVEWLLSA-NH2;

H-H-Aib-QGTFTSDYSKYLDSKAA-K(Hexadecanoyl-isoGlu)-
DFVEWLLSA-NH2; (SEQ ID NO: 113)

H-H-Aib-QGTFTSDYSKYLDSKAAHDFV-K(Hexadecanoyl-
isoGlu)-WLLSA-NH2; (SEQ ID NO: 114)

H-H-Aib-QGTFTSDYSKYLDSKAAHDFVEWLL-K(Hexadecanoyl-
isoGlu)-A-NH2; (SEQ ID NO: 130)

H-H-Aib-QGTFTSDYSKYLDS-K(Hexadecanoyl-isoLys)-
AARDFVAWLLRA-NH2; (SEQ ID NO: 115)

H-H-Aib-QGTFTSDYSKYLDS-K(Hexadecanoyl-isoGlu)-
AAKDFVEWLLSA-NH2; (SEQ ID NO: 116)

H-H-Aib-QGTFTSDYSKYLDE-K(Hexadecanoyl-isoGlu)-
AAHDFVEWLLSA-NH2; (SEQ ID NO: 117)

H-H-Aib-QGTFTSDYSKYLDS-K(Hexadecanoyl-isoGlu)-
AAHEFVEWLLSA-NH2; (SEQ ID NO: 118)

H-H-Aib-QGTFTSDYSKYLDS-K(Hexadecanoyl-isoGlu)-
AAEDFVEWLLSA-NH2;
or (SEQ ID NO: 119)

H-H-Aib-QGTFTSDYSKYLDS-K(Hexadecanoyl-isoGlu)-
AAHDFVEWLLEA-NH2, (SEQ ID NO: 120)

or a pharmaceutically acceptable salt thereof,
wherein residues marked "( )" participate in an intramolecular bond.

2. A pharmaceutically acceptable composition comprising a compound of claim 1, or a salt thereof, in a mixture with a pharmaceutically acceptable carrier.

* * * * *